United States Patent
Gieffers et al.

(10) Patent No.: US 10,870,688 B2
(45) Date of Patent: Dec. 22, 2020

(54) SINGLE-CHAIN CD137-RECEPTOR AGONIST PROTEINS

(71) Applicant: Apogenix AG, Heidelberg (DE)

(72) Inventors: Christian Gieffers, Dossenheim (DE);
Oliver Hill, Neckarsteinach (DE);
Meinolf Thiemann, Schriesheim (DE);
Tim Schnyder, Igersheim (DE)

(73) Assignee: Apogenix AG, Heidelberg (DE)

( * ) Notice: Subject to any disclaimer, the term of this patent is extended or adjusted under 35 U.S.C. 154(b) by 133 days.

(21) Appl. No.: 15/955,086

(22) Filed: Apr. 17, 2018

(65) Prior Publication Data

US 2018/0237495 A1  Aug. 23, 2018

Related U.S. Application Data

(63) Continuation of application No. PCT/EP2016/075543, filed on Oct. 24, 2016.

(60) Provisional application No. 62/245,838, filed on Oct. 23, 2015.

(51) Int. Cl.
| | | |
|---|---|---|
| C07K 14/705 | (2006.01) | |
| A61K 38/17 | (2006.01) | |
| A61K 38/19 | (2006.01) | |
| C07K 19/00 | (2006.01) | |

(52) U.S. Cl.
CPC .... *C07K 14/70578* (2013.01); *A61K 38/1774* (2013.01); *A61K 38/191* (2013.01); *C07K 14/70575* (2013.01); *C07K 19/00* (2013.01); *C07K 2319/034* (2013.01); *C07K 2319/30* (2013.01); *C07K 2319/32* (2013.01); *C07K 2319/50* (2013.01); *C07K 2319/74* (2013.01)

(58) Field of Classification Search
CPC .............. C07K 14/70575; C07K 19/00; C07K 2319/74; C07K 2319/30; A61K 38/1774; A61K 38/191
See application file for complete search history.

(56) References Cited

U.S. PATENT DOCUMENTS

2003/0223989 A1  12/2003  Pluenneke

FOREIGN PATENT DOCUMENTS

| WO | 2010/010051 | 1/2010 |
| WO | 2012/130471 | 10/2012 |
| WO | 2013/092983 | 6/2013 |

OTHER PUBLICATIONS

Eun-Young Won et al, "The Structure of the Trimer of Human 4-1BB Ligand Is Unique among Members of the Tumor Necrosis Factor Superfamily (includes Supplementary information)", Journal of Biological Chemistry, Mar. 19, 2010, pp. 9202-9210+5pp, vol. 285, No. 12.
Catherine Rabu et al, "Production of recombinant human trimeric CD137L (4-1BBL)—Cross-linking is essential to its T cell costimulation activity", Journal of Biological Chemistry, Dec. 16, 2005, pp. 41472-41481, vol. 280, No. 50, US.
International Search Report dated Feb. 8, 2017 issued in PCT/EP2016/075543.

*Primary Examiner* — Ruixiang Li
(74) *Attorney, Agent, or Firm* — Perkins Coie LLP; Viola Kung

(57) ABSTRACT

Provided herein are specific CD137 receptor agonist proteins, nucleic acids encoding the same, and methods of treating a subject having a CD137L-associated disease or disorder. The CD137 receptor agonist proteins provided herein comprise three soluble CD137L domains and an Fc fragment. The CD137 receptor agonist proteins are substantially non-aggregating and suitable for therapeuctic, diagnostic and/or research applications.

15 Claims, 7 Drawing Sheets

Specification includes a Sequence Listing.

US 10,870,688 B2

SINGLE-CHAIN CD137-RECEPTOR AGONIST PROTEINS

This application is a continuation of PCT/EP2016/075543, filed Oct. 24, 2016; which claims priority to U.S. Provisional Application No. 62/245,838, filed Oct. 23, 2015. The contents of the above applications are incorporated herein by reference in their entirety.

Reference to Sequence Listing, Table or Computer Program

The Sequence Listing is concurrently submitted herewith with the specification as an ASCII formatted text file via EFS-Web with a file name of Sequence_Listing.txt with a creation date of Apr. 11, 2018, and a size of 109 kilobytes. The Sequence Listing filed via EFS-Web is part of the specification and is hereby incorporated in its entirety by reference herein.

FIELD OF THE INVENTION

The present invention provides specific CD137 receptor agonist proteins comprising three soluble CD137L domains and an Fc fragment, nucleic acid molecules encoding the CD137 receptor agonist proteins, and uses thereof. The CD137 receptor agonist proteins are substantially non-aggregating and suitable for therapeutic, diagnostic and/or research applications.

BACKGROUND OF THE INVENTION

It is known that trimerization of TNF superfamily (TNFSF) cytokines is required for efficient receptor binding and activation. Trimeric complexes of TNF superfamily cytokines, however, are difficult to prepare from recombinant monomeric units. WO 01/49866 and WO 02/09055 disclose recombinant fusion proteins comprising a TNF cytokine and a multimerization component, particularly a protein from the C1q protein family or a collectin. A disadvantage of these fusion proteins is, however, that the trimerization domain usually has a large molecular weight and/or that the trimerization is rather inefficient.

Schneider et al. (J Exp Med 187 (1989), 1205-1213) describe that trimers of TNF cytokines are stabilized by N-terminally positioned stabilization motifs. In CD95L, the stabilization of the receptor binding domain trimer is presumably caused by N-terminal amino acid domains which are located near the cytoplasmic membrane.

Shiraishi et al. (Biochem Biophys Res Commun 322 (2004), 197-202) describe that the receptor binding domain of CD95L may be stabilized by N-terminally positioned artificial α-helical coiled-coil (leucine zipper) motifs. It was found, however, that the orientation of the polypeptide chains to each other, e.g. parallel or antiparallel orientation, can hardly be predicted. Further, the optimal number of heptad-repeats in the coiled-coil zipper motif are difficult to determine. In addition, coiled-coil structures have the tendency to form macromolecular aggregates after alteration of pH and/or ionic strength.

WO 01/25277 relates to single-chain oligomeric polypeptides which bind to an extracellular ligand binding domain of a cellular receptor, wherein the polypeptide comprises at least three receptor binding sites of which at least one is capable of binding to a ligand binding domain of the cellular receptor and at least one is incapable of effectively binding to a ligand binding domain of the cellular receptor, whereby the single-chain oligomeric polypeptides are capable of binding to the receptor, but incapable of activating the receptor. For example, the monomers are derived from cytokine ligands of the TNF family, particularly from TNF-α.

WO 2005/103077 discloses single-chain fusion polypeptides comprising at least three monomers of a TNF family ligand member and at least two peptide linkers that link the monomers of the TNF ligand family members to one another. Recent experiments, however, have shown that these singlechain fusion polypeptides show undesired aggregation.

WO 2010/010051 discloses single-chain fusion polypeptides comprising three soluble TNF family cytokine domains and at least two peptide linkers. The described fusion polypeptides are substantially non-aggregating.

Recent studies have shown that the in vivo anti tumor activity of an anti-CD137-mAb is dependent on Fc-gamma-R driven mechanisms and does not rely on agonistic activity only.

There is a need in the art for novel CD137 receptor agonists that exhibit high biological activity independent of Fc-gamma-R based crosslinking in vivo, high stability, and allow for efficient recombinant manufacturing.

SUMMARY OF THE INVENTION

The present invention provides specific CD137 receptor agonist proteins that mimic the CD137:CD137L interaction in vivo, exhibit low proteolytic degradation and a shorter in vivo half-life as compared to agonistic monoclonal antibodies.

The CD137 receptor agonist proteins of the instant invention generally comprise: (i) a first soluble CD137L cytokine domain; (ii) a first peptide linker; (iii) a second soluble CD137L domain; (iv) a second peptide linker; (v) a third soluble CD137L domain; (vi) a third peptide linker (e.g., a hinge-linker) and (vii) an antibody Fc fragment.

In one embodiment, the antibody Fc fragment (vii) is located N terminal to the first CD137L domain (i) and/or C-terminal to the third CD137L domain (v). In another embodiment the antibody Fc fragment is located C-terminally to the third CD137L domain (v). In one embodiment, the polypeptide is substantially non-aggregating. In another embodiment, the second and/or third soluble CD137L domain is an N-terminally shortened domain which optionally comprises amino acid sequence mutations. In another embodiment, the soluble CD137L domains (i), (ii) and (iii) are an C-terminally shortened domain which optionally comprises amino acid sequence mutations.

In one embodiment, at least one of the soluble CD137L domains, particularly at least one of the soluble CD137L domains (iii) and (v), is a soluble CD137L domain with an N-terminal sequence which starts at amino acid D86 or R88 or Q89 or G90 of human CD137L and wherein D86 or R88 or Q89 may be replaced by a neutral amino acid, e.g., Ser or Gly. In another embodiment, at least one of the soluble CD137L domains, particularly at least one of the soluble CD137L domains (iii) and (v), is a soluble CD137L domain with an N-terminal sequences selected from (a) D86-G90 and (b) (Gly/Ser)89-G90. In one embodiment, the soluble CD137L domain ends with amino acid E254 of human CD137L and/or optionally comprises one or more mutation at positions D86, L87, R88, Q89, D112, V118, A154, A174, A176, A188, T241. In one embodiment, the soluble CD137L domains (i), (iii) and (v) comprise amino acids D86-E254 of human CD137L according to SEQ ID NO: 1.

In one embodiment, at least one of the soluble CD137L domains, particularly at least the soluble CD137L domains (i), is a soluble CD137L domain with an N-terminal sequence which starts at amino acid R88 and wherein R88 may be replaced by Ser or Gly. In one embodiment, at least one of the soluble CD137L domains, particularly at least the soluble CD137L domain (iii), is a soluble C-terminal shortened CD137L domain ending with V240. In another embodiment, at least one of the soluble CD137L domains, particularly at least the soluble CD137L domains (iii), is a soluble C-terminal shortened CD137L domain ending with T241. In still another embodiment, at least one of the soluble CD137L domains, particularly at least the soluble CD137L domains (iii), is a soluble C-terminal shortened CD137L domain ending with E243.

In one embodiment, the first and second peptide linkers (ii) and (iv) independently have a length of 3-8 amino acids, particularly a length of 3, 4, 5, 6, 7, or 8 amino acids, and preferably are glycine/serine linkers, optionally comprising an asparagine residue which may be glycosylated. In one embodiment, the first and the second peptide linkers (ii) and (iv) consist of the amino acid sequence according to SEQ ID NO: 2. In another embodiment, the polypeptide additionally comprises an N-terminal signal peptide domain, e.g., of SEQ ID NO: 17, which may comprise a protease cleavage site, and/or which additionally comprises a C-terminal element which may comprise and/or connect to a recognition/purification domain, e.g., a Strep-tag attached to a serine linker according to SEQ ID NO: 18.

In one embodiment, the antibody Fc fragment (vii) is fused to the soluble CD137L domain (i) and/or (v) via a hinge-linker, preferably of SEQ ID NO: 16. In another embodiment, the antibody Fc fragment (vii) consists of the amino acid sequence as shown in SEQ ID NO: 13 or 14.

In one embodiment, the single-chain fusion polypeptide of the present invention comprises the amino acid sequence selected from the group consisting of SEQ ID NO: 15, and 25-35.

In one embodiment, the present invention provides a CD137 receptor agonist protein comprising a dimer of two single-chain fusion polypeptides each having the amino acid sequence set forth in SEQ ID NO: 27. In one embodiment, the two polypeptides are covalently linked through three interchain disulfide bonds formed between cysteine residues 484, 490, and 493 of each polypeptide. Similar cysteine residues are positions 484, 490 and 493 of SEQ ID NO: 28, 29 or 32, positions 489, 495 and 498 of SEQ ID NO: 30, positions 493, 499 and 502 of SEQ ID NO: 31, and positions 487, 493 and 496 of SEQ ID NO: 33 or 34

In one embodiment, one or more of the asparagine residues at positions 158 and 318 of the mature polypeptide(s) SEQ ID NO: 27, 28 or 29 are N-glycosylated. In another embodiment, the asparagine residues at positions 158 and 318 of the polypeptide(s) are both N-glycosylated. Similar asparagine residues are positions 161 and 324 of SEQ ID NO: 30 or 31, and positions 159 and 320 of SEQ ID NO: 33 or 34

In another embodiment, the polypeptide(s) are further post-translationally modified. In another embodiment, the post-translational modification comprises the N-terminal glutamine of the D86Q mutein of the first soluble domain (i) modified to pyroglutamate. In still another embodiment, the post-translational modification comprises the N-terminal glutamine of the first soluble domain (i) starting with Q89 modified to pyroglutamate.

DETAILED DESCRIPTION OF THE INVENTION

Figure 1:
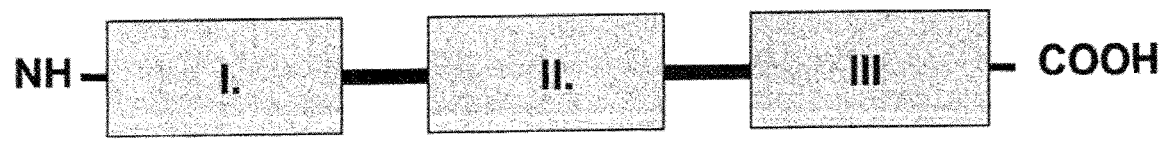
FIG. 1 Domain structure of a single-chain fusion polypeptide comprising three CD137L domains. I., II., III. Soluble CD137L domains.
Figure 1:
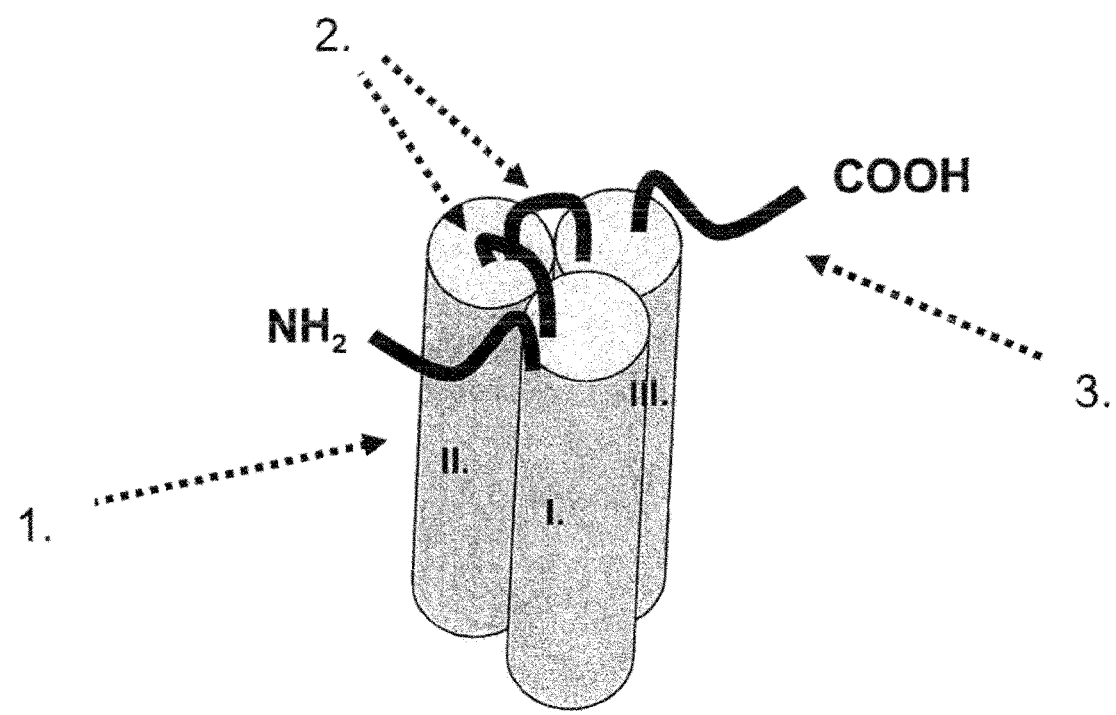
Figure 2:
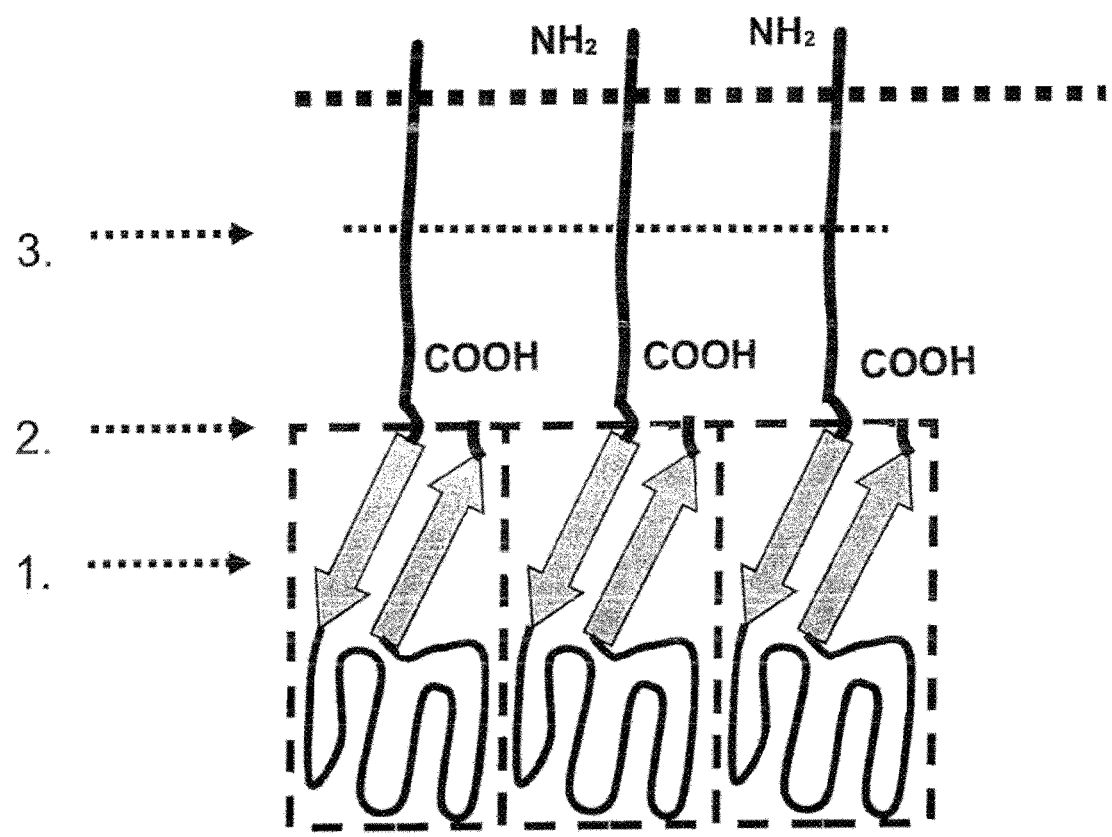
FIG. 2 Schematic picture representing the general structure of CD137L.
■ ■ ■ Cell membrane, N-terminus located within the cell,
1. anti-parallel β-fold of receptor-binding domain (RBD),
2. interface of RBD and cell membrane,
3. protease cleavage site.
Figure 3:
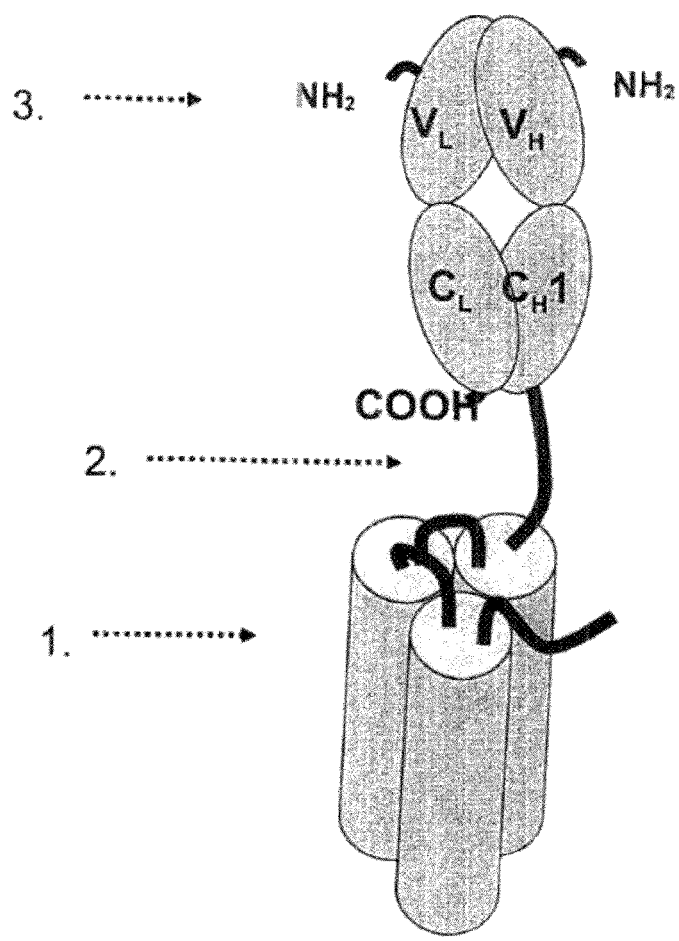
FIG. 3 Single-chain fusion polypeptide comprising an additional Fab antibody fragment.
Figure 4:
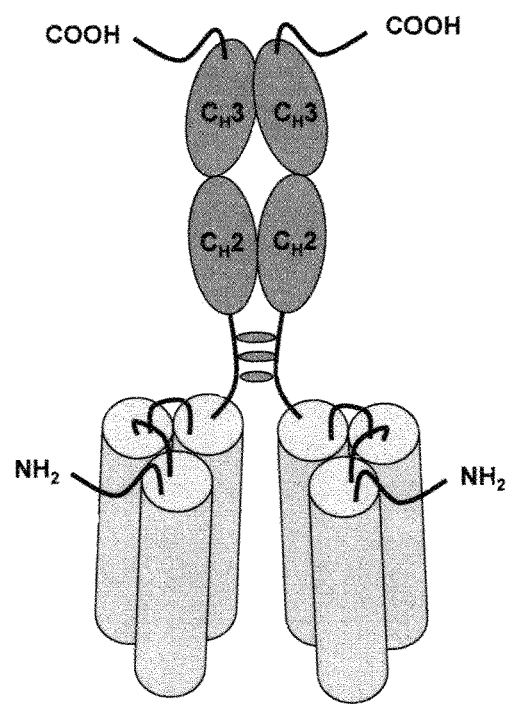
FIG. 4 Dimerization of two C-terminally fused single-chain Fc fusion polypeptides via three disulfide bridges.
Figure 5:
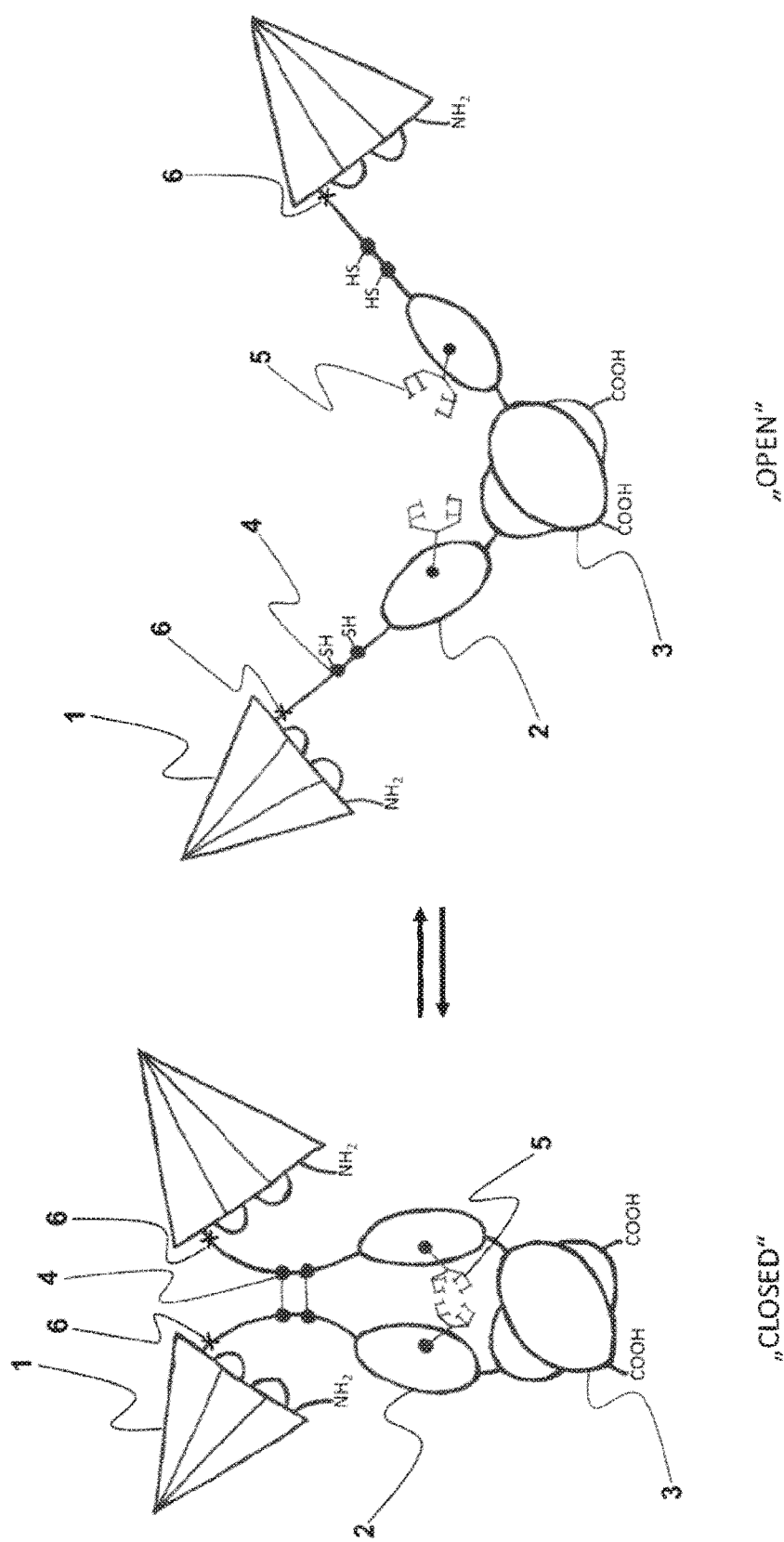
FIG. 5 Schematic representation of the hexavalent single chain CD27 receptor agonist fusion protein of the invention. CH2-Carbohydrates (5) present on the inner surface areas normally shield the CH2-subdomain sterically (2) from proteases during "open Fc-conformation transits" wherein hinge-interchain disulfide bonds (4) are reduced and the covalent interchain linkage is disrupted. This enables CH2-dissociation and exposure of the inner surface areas and the upper hinge lysine K223 (6) towards proteases. Dimer association in the "open stage" remains intact due to the high affinity of the CH3 domains (3) to each other.
(1) scCD27L-RBD; (2) CH2 domain; (3) CH3 domain; (4) Hinge-Cysteines (left side: oxidized to disulfide bridges; right side reduced stage with free thiols); (5) CH2-Carbohydrates attached to N297 position (EU-numbering); (6) Upper Hinge Lysine (K223)

The present invention provides a single-chain fusion polypeptide comprising at least three soluble CD137L domains connected by two peptide linkers and N-terminally and/or C-terminally an antibody-derived dimerization domain. The inventors have discovered that dimerization of the two single-chain fusion polypeptides through the dimerization domain results in a hexavalent CD137 receptor agonist, which provides high biological activity and good stability.

Preferably, the single-chain fusion polypeptide is non-aggregating. The term "non-aggregating" refers to a monomer content of the preparation of ≥50%, preferably ≥70% and more preferably ≥90%. The ratio of monomer content to aggregate content may be determined by examining the amount of aggregate formation using size-exclusion chromatography (SEC). The stability concerning aggregation may be determined by SEC after defined time periods, e.g. from a few to several days, to weeks and months under different storage conditions, e.g. at 4° C. or 25° C. For the fusion protein, in order to be classified as substantially non-aggregating, it is preferred that the "monomer" content is as defined above after a time period of several days, e.g. 10 days, more preferably after several weeks, e.g. 2, 3 or 4 weeks, and most preferably after several months, e.g. 2 or 3 months of storage at 4° C., or 25° C. With regard to the definition of "monomer" in the case of FC-fusion proteins, the assembly of two polypeptide chains is driven by the FC-part and the functional unit of the resulting assembled protein consists of two chains. This unit is defined as "monomer" in the case of Fc-fusion proteins regardless of being a dimerized single-chain fusion polypeptide.

The single-chain fusion polypeptide may comprise additional domains which may be located at the N- and/or C-termini thereof. Examples for additional fusion domains are e.g. an N-terminal signal peptide domain which may comprise a protease cleave site or a C-terminal element which may comprise and/or connect to a recognition/purification domain. According to a preferred embodiment, the fusion polypeptide comprises a Strep-tag at its C-terminus that is fused via a linker. An exemplary Strep-tag including a short serine linker is shown in SEQ ID NO: 18.

The CD137 receptor agonist protein of the present invention comprises three soluble domains derived from CD137L. Preferably, those soluble domains are derived from a mammalian, particularly human CD137L including allelic variants and/or derivatives thereof. The soluble domains comprise the extracellular portion of CD137L including the receptor binding domain without membrane located domains. Like other proteins of the TNF superfamily, CD137L is anchored to the membrane via an N-terminal portion of 15-30 amino acids, the so-called stalk-region. The stalk region contributes to trimerization and provides a certain distance to the cell membrane. However, the stalk region is not part of the trimeric receptor binding domain (RBD) with the receptor binding sites located at the protomer interfaces.

Importantly, the RBD of the Tumor Necrosis Factor Superfamily is characterized by a particular localization of its N- and C-terminal amino acids. Said amino acids are immediately adjacent and are located in close proximity to the axis of the trimer. The first N-terminal amino acids of the RBD form an anti-parallel beta-strand with a C-terminal region of the RBD. Thus, the aforementioned anti-parallel beta-strand of the RBD forms an interface with the cell membrane, which is connected to and anchored within the cell membrane via the amino acids of the stalk region.

Human CD137L contains a stalk region as well as most likely a C-terminal extension (V240-E254).

It is highly preferred that the soluble CD137L domains of the CD137 receptor agonist protein comprise a receptor binding domain of the CD137L lacking any amino acids from the stalk region. Otherwise, a long linker connecting the C-terminus of one of the soluble domains with the N-terminus of the next soluble domain would be required to compensate for the N-terminal stalk-region of the next soluble domain, which might result in instability and/or formation of aggregates. For the same reason, it is also highly preferred that the soluble CD137L domains of the CD137 receptor agonist protein comprise a receptor binding domain of the CD137L lacking any amino acids from the C-terminal extension.

A further advantage of such soluble domains is that the N-terminal amino acids of the RBD are not accessible for any anti-drug antibodies. Preferably, the single-chain fusion polypeptide consisting of (i) a first soluble CD137L domain; (ii) a first peptide linker; (iii) a second soluble CD137L domain; (iv) a second peptide linker; (v) a third soluble CD137L domain is capable of forming an ordered structure mimicking the trimeric organization of its natural counterpart thereby comprising at least one functional binding site for the respective CD137L receptor. The single-chain fusion polypeptide comprising components (i)-(v) is therefore also termed single-chain-CD137L-receptor-binding-domain (scCD137L-RBD). Importantly, compared to homotrimeric wild type CD137L-RBD, the scCD137L-RBD comprises an enhanced stability as the soluble CD137L domains (i), (iii) and (v) are enforced to trimerize by the covalent linkage to each other provided by the linkers (ii) and (iv).

The CD137 receptor agonist protein comprises three functional CD137 receptor binding sites, i.e. amino acid sequences capable of forming a complex with a CD137 receptor. Thus, the soluble domains are capable of binding to the corresponding CD137 receptor. In one embodiment, at least one of the soluble domains is capable of receptor activation, whereby apoptotic and/or proliferative activity may be affected. In a further embodiment, one or more of the soluble domains are selected as not being capable of receptor activation.

The soluble CD137L domain may be derived from human CD137L as shown in SEQ ID NO: 1. Preferably, the soluble CD137L domains are derived from human CD137L, particularly starting from amino acids 86, 88, 89 or 90 and comprise particularly amino acids 86-254 or 88-254 or 89-254 of SEQ ID NO: 1. Optionally, amino acid R88 of SEQ ID NO: 1 may be replaced by a noncharged amino acid, e.g. Ser or Gly or is replaced by Glutamine.

TABLE 1

Sequence of Wild-Type Human CD137IL Protein

| SEQ ID NO | Sequence |
|---|---|
| 1 | MEYASDASLDPEAPWPPAPRARACRVLPWALVAGLLLLLLLAAAC AVFLACPWAVSGARASPGSAASPRLREGPELSPDDPAGLLDLRQG MFAQLVAQNVLLIDGPLSWYSDPGLAGVSLTGGLSYKEDTKELVV AKAGVYYVFFQLELRRVVAGEGSGSVSLALHLQPLRSAAGAAALA LTVDLPPASSEARNSAFGFQGRLLHLSAGQRLGVHLHTEARARHA WQLTQGATVLGLFRVTPEIPAGLPSPRSE |

As indicated above, the soluble CD137L domains may comprise the wild-type sequences as indicated in SEQ ID NO: 1. It should be noted, however, that it is possible to introduce mutations in one or more of these soluble domains, e.g. mutations which alter (e.g. increase or decrease) the binding properties of the soluble domains. In one embodiment, soluble domains that cannot bind to the corresponding cytokine receptor can be selected.

In a further embodiment of the invention, the soluble CD137L domain (i) comprises a mutant of CD137L or a receptor binding domain thereof resulting in reduced affinity and/or reduced activation of CD137 receptor.

CD137L-Muteins Affecting Receptor Binding and/or Activity

The mutant may be generated by any technique known by a skilled person. The substitution may affect at least one amino acid of CD137L, e.g., human CD137L (e.g., SEQ ID NO: 1) or a receptor binding domain thereof as described herein. Preferred substitutions in this regard affect at least one of the following amino acids of human CD137L of SEQ ID NO: 1: L115, K127, R150, R193 and Q227.

In another preferred embodiment, the C-terminal region 1243-E254 is deleted from at least one of the soluble domains (i), (Ill) or (v).

The amino acid substitution(s) may affect the binding and/or activity of CD137L, e.g., human CD137L, to or on either the CD137 binding or the CD137 induced signaling.

The binding and/or activity of the CD137 may be affected positively, i.e., stronger, more selective or more specific binding and/or more activation of the receptor. Alternatively, the binding and/or activity of the CD137 may be affected negatively, i.e., weaker, less selective or less specific binding and/or less or no activation of the receptor.

Thus one embodiment is a CD137 receptor agonist protein as described herein wherein at least one of the soluble domains comprises a mutant of CD137L or a receptor binding domain thereof which binds and/or activates CD137 to a lesser extent than the wildtype-CD137L.

CD137L-Muteins with Enhanced Stability/Solubility

In a further embodiment of the invention, one or more of the soluble CD137L domains (i), (iii), and (v) may comprise a mutant of CD137L or a receptor binding domain thereof resulting in reduced self-aggregation and/or prolonged in vivo stability. A174, A176. Preferred substitutions in this regard are A174[D, N] and A176[S, T]. The mutation(s) of each CD137L domain may be the same or different.

The single-chain fusion molecule of the present invention comprises three soluble CD137L domains, namely components (i), (iii) and (v). The stability of a single-chain CD137L fusion polypeptide against aggregation is enhanced, if the second and/or third soluble CD137L domain is an N-terminally shortened domain which optionally comprises amino acid sequence mutations. Thus, preferably, both the second and the third soluble CD137L domain are N-terminally shortened domains which optionally comprise amino acid sequence mutations in the N-terminal regions, preferably within the first five amino acids of the N-terminus of the soluble CD137L domain. These mutations may comprise replacement of basic amino acids, by neutral amino acids, particularly serine or glycine.

In contrast thereto, the selection of the first soluble CD137L domain is not as critical. Here, a soluble domain having a full-length N-terminal sequence may be used. It should be noted, however, that also the first soluble CD137L domain may have an N-terminally shortened and optionally mutated sequence.

In a further preferred embodiment of the present invention, the soluble CD137L domains (i), (iii) and (v) are soluble human CD137L domains. The first soluble CD137L domain (i) may be selected from native, shortened and/or mutated sequences. Thus, the first soluble CD137L domain (i) has a N-Terminal sequence which may start at amino acid D86 or R88 of human CD137L, and wherein R88 may be replaced by a neutral amino acid, e.g. by Ser or Gly or by Gln to enable pyroglutamate formation during expression. The second and third soluble CD137L domains (iii) and (v) have a shortened N-terminal sequence which preferably starts with amino acid Q89 or G90 of human CD137L (SEQ ID NO:1) and wherein Q89 may be replaced by another amino acid, e.g. Ser or Gly.

Preferably, the N-terminal sequence of the soluble CD137L domains (iii) and (v) is selected from:
(a) D86 or Q89
(b) (Gly/Ser) 89

The soluble CD137L domain preferably ends with amino acid E254 of human CD137L. In certain embodiments, the CD137L domain may comprise internal mutations as described above.

In another preferred embodiment, the soluble CD137L domain preferably ends with amino acid V240 of human CD137L. In certain embodiments, the CD137L domain may comprise internal mutations as described above.

Components (ii) and (iv) of the CD137 receptor agonist protein are peptide linker elements located between components (i) and (iii) or (iii) and (v), respectively. The flexible linker elements have a length of 3-8 amino acids, particularly a length of 3, 4, 5, 6, 7, or 8 amino acids. The linker elements are preferably glycine/serine linkers, i.e. peptide linkers substantially consisting of the amino acids glycine and serine. In cases in in which the soluble cytokine domain starts with S or G (N-terminus), the linker ends before this S or G.

It should be noted that linker (ii) and linker (iv) do not need to be of the same length. In order to decrease potential immunogenicity, it may be preferred to use shorter linkers. In addition it turned out that shorter linkers lead to single chain molecules with reduced tendency to form aggregates. Whereas linkers that are substantially longer than the ones disclosed here may exhibit unfavorable aggregations properties.

If desired, the linker may comprise an asparagine residue which may form a glycosylate site Asn-Xaa-Ser. In certain embodiments, one of the linkers, e.g. linker (ii) or linker (iv) comprises a glycosylation site. In other embodiments, both linkers (iv) comprise glycosylation sites. In order to increase the solubility of the CD137L agonist proteins and/or in order to reduce the potential immunogenicity, it may be preferred that linker (ii) or linker (iv) or both comprise a glycosylation site.

Preferred linker sequences are shown in Table 2. A preferred linker is GSGSGNGS (SEQ ID NO: 2).

TABLE 2

Example Linker Sequences

| SEQ ID NO | Sequence |
|---|---|
| 2 | GSGSGNGS |
| 3 | GSGSGSGS |
| 4 | GGSGSGSG |
| 5 | GGSGSG |
| 6 | GGSG |
| 7 | GGSGNGSG |
| 8 | GGNGSGSG |
| 9 | GGNGSG |
| 10 | GSGSGS |
| 11 | GSGS |
| 12 | GSG |

The CD137 receptor agonist protein additionally comprises an antibody Fc fragment domain which may be located N-terminal to the first CD137L domain (i) and/or C-terminal to the third CD137L domain (v). Preferably, the antibody Fc fragment domain comprises a reduced capability to interact with Fc-gamma-R receptors in vivo. Preferably, the antibody Fc fragment domain comprises or consists of an amino acid sequence as shown in SEQ ID NO: 13 or 14 (see Table 3). Sequence ID NO: 13 has N297S mutation compared to wildtype human IGG1-Fc. Sequence ID NO: 14 is a glycosylated (N297 wildtype) human IGG1 Fc mutein with reduced Fc-gamma-R binding capability.

TABLE 3

Examples of Fc Fragment Domains

| SEQ ID NO | Sequence |
|---|---|
| 13 | PAPELLGGPSVFLFPPKPKDTLMISRTPEVTCVVVDVSHEDPEVK FNWYVDGVEVHNAKTKPREEQY<u>SS</u>TYRVVSVLTVLHQDWLNGKEY KCKVSNKALPAPIEKTISKAKGQPREPQVYTLPPSREEMTKNQVS LTCLVKGFYPSDIAVEWESNGQPENNYKTTPPVLDSDGSFFLYSK LTVDKSRWQQGNVFSCSVMHEALHNHYTQKSLSLSPGK |
| 14 | PAPPVAGPSVFLFPPKPKDTLMISRTPEVTCVVVDVSHEDPEVKF NWYVDGVEVHNAKTKPREEQY<u>N</u>STYRVVSVLTVLHQDWLNGKEYK CKVSNKGLPSSIEKTISKAKGQPREPQVYTLPPSREEMTKNQVSL TCLVKGFYPSDIAVEWESNGQPENNYKTTPPVLDSDGSFFLYSKL TVDKSRWQQGNVFSCSVMHEALHNHYTQKSLSLSPGK |

Number of Glycosylation Sites and In Vivo Stability

The total number of glycosylation sites and the individual position of the carbohydrates in three dimensions impacts the in-vivo stability of CD137 receptor agonist proteins.

Further, carbohydrate recognition depends on local density of the terminal saccharides, the branching of the carbohydrate tree and the relative position of the carbohydrates to each other matter.

Further, partially degraded carbohydrates reduce the in vivo half-life of CD137 receptor agonist proteins through lectin-driven mechanisms. By reducing the total number of glycosylation sites on the molecule, the resulting compound is less accessible to these mechanisms, increasing half-life.

Depletion of the CH2-domain carbohydrates of the Fc-domain is necessary in order to avoid Fc-gamma-Receptor based binding. FcR-gamma-Receptors on cells could lead to hyper-crosslinking of the fusion-protein in vivo potentially leading to CD137-receptor superclustering-based toxicity. Also, unwanted Fc-driven mechanisms like ADCC could lead to toxic events. Accordingly, in one embodiment, the overall number of glycosylation sites on the CD137 receptor agonist proteins of the instant invention is reduced through the depletion of CH2 glycosylation sites, particularly the N-glycosylation site, resulting in CD137 receptor agonist proteins comprising N297S equivalent mutations of SEQ ID NO: 15 (PROTEIN A) (according to the EU numbering system) creating aglycosl-CH2 domains.

CH2-Domain Destabilization is Compensated by an Additional Hinge-Cysteine

CH2-glycosylation present on the inner surface areas normally shields the subdomain from proteases during "open Fc-conformation transits" wherein hinge-interchain disulfide bonds are reduced and the covalent interchain linkage is disrupted. This enables CH2-dissociation and exposure of the inner surface area towards proteases. CD137 receptor agonist proteins comprising an Fc-domain with a N297S equivalent mutation of SEQ ID NO: 15 (PROTEIN A) (according to the EU numbering system) creates an aglycosylated-CH2 and are therefore likely to be subject to protease digestion and less stable than equivalent structures with wild-type CH2 glycosylation. This would impact the compound's stability during USP/DSP/storage, where host cell proteases are present and have long-term access to the structure. Accordingly, in certain embodiments, the CD137 receptor agonist lacks CH2 glycosylation sites, but comprises glycosylation sites in the linker sequences of each polypeptide chain (e.g., GSGSGNGS, SEQ ID NO: 2).

According to a preferred embodiment of the invention, the antibody Fc fragment domain is fused via a hinge linker element. The hinge-linker element has a length of 10-30 amino acids, particularly a length of 15-25 amino acids, e.g. 22 amino acids. The term "hinge-linker" includes any linker long enough to allow the domains attached by the hinge linker element to attain a biologically active confirmation. The hinge-linker element preferably comprises the hinge-region sequence of an immunoglobulin, herein referred to as "Ig hinge-region". The term "Ig hinge region" means any polypeptide comprising an amino acid sequence that shares sequence identity or similarity with a portion of a naturally occurring Ig hinge-region sequence which includes one or more cysteine residues, e.g., two cysteine residues, at which the disulfide bonds link the two heavy chains of the immunoglobulin.

Derivatives and analogues of the hinge-region can be obtained by mutations. A derivative or analogue as referred to herein is a polypeptide comprising an amino acid sequence that shares sequence identity or similarity with the full length sequence of the wild type (or naturally occurring protein) except that it has one or more amino acid sequence differences attributable to a deletion, insertion and/or substitution.

The number of molecules with open Fc-conformation in an individual CD137 receptor agonist protein depends on the number of interchain-disulfide bonds present in the hinge region. Accordingly, in one embodiment a third cysteine (C225 according to the EU numbering system) was introduced into the hinge region of the CD137 receptor agonist proteins of the instant invention in order to ameliorate the effect of depleting the CH2-glycosites.

Exchange of a Lysine to Glycine in the Hinge Region Results in Enhanced Proteolytic Stability In one embodiment, the CD137 receptor agonist proteins of the invention additionally comprise a mutation of the upper-hinge lysine (K223, according to the EU numbering system) to a glycine to reduce proteolytic processing at this site, thereby enhancing the overall stability of the fusion protein. Combining aforementioned introduction of a third cysteine (C225, according to the EU numbering system) with the aforementioned lysine to glycine mutation (K223G, according to the EU numbering system) within the hinge region results in an overall stabilized CD137 receptor agonist protein of the instant invention.

A particularly preferred hinge-linker element including the aforementioned cysteine (C225) and the lysine to glycine mutation (K223G) comprises or consists of the amino acid sequence as shown in SEQ ID NO: 16 (Table 4).

The CD137 receptor agonist protein may additionally comprise an N-terminal signal peptide domain, which allows processing, e.g. extracellular secretion, in a suitable host cell. Preferably, the N-terminal signal peptide domain comprises a protease cleavage site, e.g. a signal peptidase cleavage site and thus may be removed after or during expression to obtain the mature protein. A particularly preferred N-terminal signal peptide domain comprises the amino acid sequence as shown in SEQ ID NO: 17 (Table 4).

Further, the CD137 receptor agonist protein may additionally comprise a C-terminal element, having a length of e.g. 1-50, preferably 10-30 amino acids which may include or connect to a recognition/purification domain, e.g. a FLAG domain, a Streptag or Strep-tag II domain and/or a poly-His domain. According to a preferred embodiment, the fusion polypeptide comprises a Streptag fused to the C-terminus via a short serine linker as shown in SEQ ID NO: 18 (Table 4).

Preferred hinge-linker elements (SEQ ID NO: 16, 19-24), a preferred N-terminal signal peptide domain (SEQ ID NO: 17) and a preferred serine linker-strep tag (SEQ ID NO: 18) are shown in Table 4.

TABLE 4

Exemplary domains and linkers

| SEQ ID NO | Sequence |
| --- | --- |
| 16 | GSSSSSSSSGSCDKTHTCPPC |
| 17 | METDTLLVFVLLVWVPAGNG |
| 18 | SSSSSSAWSHPQFEK |
| 19 | GSSSSSSSGSCDKTHTCPPC |
| 20 | GSSSSSSGSCDKTHTCPPC |
| 21 | GSSSSSGSCDKTHTCPPC |
| 22 | GSSSGSCDKTHTCPPC |
| 23 | GSSSGSCDKTHTCPPCGS |
| 24 | GSSSGSCDKTHTCPPCGSGS |

In one embodiment of the invention, the fusion polypeptide comprises three soluble CD137L domains fused by peptide linker elements of SEQ ID NO: 2. All three soluble CD137L domain (i), (iii), (v) consists of amino acids 89-240 of human CD137L according to SEQ ID NO: 1. The resulting scCD137L-RBD sequence module is shown in table 5b SEQ ID NO: 36.

In a further preferred embodiment of the invention, the fusion polypeptide comprises three soluble CD137L domains fused by peptide linker elements of SEQ ID NO: 2. All three soluble CD137L domain (i), (iii), (v) consists of amino acids 86-240 of human CD137L according to SEQ ID NO: 1 with D86Q mutation in the first domain (i). The resulting scCD137L-RBD sequence module is shown in table 5b SEQ ID NO: 39.

In another embodiment of the invention, the fusion polypeptide comprises three soluble CD137L domains fused by peptide linker elements of SEQ ID NO: 2. All three soluble CD137L domain (i), (iii), (v) consists of amino acids 88-240 of human CD137L according to SEQ ID NO: 1. The resulting scCD137L-RBD sequence module is shown in table 5b SEQ ID NO: 40.

In still another preferred embodiment of the invention, the fusion polypeptide comprises three soluble CD137L domains fused by peptide linker elements of SEQ ID NO: 2. All three soluble CD137L domain (i), (iii), (v) consists of amino acids 88-240 of human CD137L according to SEQ ID NO: 1 with R88Q mutation in the first domain (i) and R88G mutation in domains (iii) and (v). The resulting scCD137L-RBD sequence module is shown in table 5b SEQ ID NO: 41.

In still another preferred embodiment of the invention, the fusion polypeptide comprises three soluble CD137L domains fused by peptide linker elements of SEQ ID NO: 2. All three soluble CD137L domain (i), (iii), (v) consists of amino acids 88-240 of human CD137L according to SEQ ID NO: 1 with R88S mutation in the first domain (i) and R88G mutation in domains (iii) and (v). The resulting scCD137L-RBD sequence module is shown in table 5b SEQ ID NO: 42.

In still another preferred embodiment of the invention, the fusion polypeptide comprises three soluble CD137L domains fused by peptide linker elements of SEQ ID NO: 2. All three soluble CD137L domain (i), (iii), (v) consists of amino acids 89-240 of human CD137L according to SEQ ID NO: 1 and comprise the A174N and A176S mutations. The resulting scCD137L-RBD sequence module is shown in table 5b SEQ ID NO: 43.

The aforementioned scCD137L-RBD modules (SEQ ID: 36, 39-43) are well suited to generate fusion proteins with additional domains fused to either N- or C-terminal end employing the linkers described in Table 2 (SEQ ID NO: 2-12).

Preferred Configuration CD137L-Fc

Additionally, the fusion polypeptide comprises an antibody Fc fragment domain according to SEQ ID NO: 13 that is fused C-terminally to the soluble CD137L domain (v) via a hingelinker according to SEQ ID NO: 16. The inventors surprisingly found that this particular fusion polypeptide provides improved biological activity as compared to bivalent agonistic anti-CD137-mAB and has a prolonged stability as compared to fusion proteins comprising a lysine in position 223 and a N297S mutation in the CH2 domain (according to the EU numbering).

The amino acid sequence of an exemplary embodiment of a CD137 receptor agonist protein of the invention is set forth in SEQ ID NO: 27.

Further, the fusion polypeptide may comprise an N-terminal signal peptide domain e.g. according to SEQ ID NO: 17. A specific example of a CD137 receptor agonist protein of the invention is shown in SEQ ID NO: 25.

According to another preferred embodiment, the fusion polypeptide may additionally comprise a C-terminal Strep-tag that is fused to the polypeptide of the invention via a short serine linker as shown in SEQ ID NO: 18. According to this aspect of the invention, the Fc fragment preferably consists of the amino acid sequence as shown in SEQ ID NO: 13 or 14. Further, the Fc fragment may consist of a shorter Fc fragment, for example including amino acids 1217 of SEQ ID NO: 13. Particularly preferred examples of fusion polypeptides comprising a C-terminal Strep-tag are shown in SEQ ID NO: 15 (PROTEIN A).

The exemplary CD137 receptor agonist proteins as shown in SEQ ID Nos: 15, 25, and 26, each comprises an N-terminal signal peptide domain, at amino acids 1-20 of each sequence. In each case, the mature protein starts with amino acid 21. Mature exemplary CD137 receptor agonist proteins (without a signal peptide) of the instant invention are set forth in SEQ ID NO: 27-35. Exemplary CD137 receptor agonist proteins described above are shown in Table 5.

The CD137 receptor agonist as set forth in SEQ ID NO: 27 has a reduced total number of glycosylation sites (the N297S mutation in the CH2 region providing an aglycosylated CH2 domain, according to the EU numbering system), an increased number of inter-chain disulfide bonds in the hinge region, and the mutation of an upper-hinge lysine to a glycine (K223G, according to the EU numbering system). These alterations provide a decrease in potential degradation and CD137 receptor superclustering (along with concomitant toxicity).

The CD137 receptor agonist as set forth in SEQ ID NO: 30 comprises a scCD137L-RBD module with SEQ ID NO: 36, a third peptide linker with SEQ ID NO: 21 and (vii) an antibody Fc fragment with SEQ ID NO: 13.

The CD137 receptor agonist as set forth in SEQ ID NO: 31 comprises a scCD137L-RBD module with SEQ ID NO: 39, a third peptide linker with SEQ ID NO: 16 and (vii) an antibody Fc fragment with SEQ ID NO: 13.

The CD137 receptor agonist as set forth in SEQ ID NO: 32 comprises a scCD137L-RBD module with SEQ ID NO: 40, a third peptide linker with SEQ ID NO: 16 and (vii) an antibody Fc fragment with SEQ ID NO: 13.

The CD137 receptor agonist as set forth in SEQ ID NO: 33 comprises a scCD137L-RBD module with SEQ ID NO: 41, a third peptide linker with SEQ ID NO: 16 and (vii) an antibody Fc fragment with SEQ ID NO: 13.

The CD137 receptor agonist as set forth in SEQ ID NO: 34 comprises a scCD137L-RBD module with SEQ ID NO: 42, a third peptide linker with SEQ ID NO: 16 and (vii) an antibody Fc fragment with SEQ ID NO: 13.

TABLE 5

Exemplary CD137 receptor agonist proteins

| SEQ ID NO | | Sequence |
|---|---|---|
| 25 | PROTEIN A without StrepTag | METDTLLVFVLLVWVPAGNGQGMFAQLVAQNVLLIDGPLSWYSDPGLAGVSLTGGLSYKEDTKELV VAKAGVYYVFFQLELRRVVAGEGSGSVSLALHLQPLRSAAGAAALALTVDLPPASSEARNSAFGFQ GRLLHLSAGQRLGVHLHTEARARHAWQLTQGATVLGLFRVGSGSGNGSQGMFAQLVAQNVLLIDGP LSWYSDPGLAGVSLTGGLSYKEDTKELVVAKAGVYYVFFQLELRRVVAGEGSGSVSLALHLQPLRS AAGAAALALTVDLPPASSEARNSAFGFQGRLLHLSAGQRLGVHLHTEARARHAWQLTQGATVLGLF RVGSGSGNGSQGMFAQLVAQNVLLIDGPLSWYSDPGLAGVSLTGGLSYKEDTKELVVAKAGVYYVF FQLELRRVTAGEGSGSVSLALHLQPLRSAAGAAALALTVDLPPASSEARNSAFGFQGRLLHLSAGQ RLGVHLHTEARARHAWQLTQGATVLGLFRVGSSSSSSSSGSCDKTHTCPPCPAPELLGGPSVFLFP PKPKDTLMISRTPEVTCVVVDVSHEDPEVKFNWYVDGVEVHNAKTKPREEQYSSTYRVVSVLTVLH QDWLNGKEYKCKVSNKALPAPIEKTISKAKGQPREPQVYTLPPSREEMTKNQVSLTCLVKGFYPSD IAVEWESNGQPENNYKTTPPVLDSDGEFFLYSKLTVDKSRWQQGNVFSCSVMHEALHNHYTQKSLS LSPGK |
| 15 | PROTEIN A | METDTLLVFVLLVWVPAGNGQGMFAQLVAQNVLLIDGPLSWYSDPGLAGVSLTGGLSYKEDTKELV VAKAGVYYVFFQLELRRVVAGEGSGSVSLALHLQPLRSAAGAAALALTVDLPPASSEARNSAFGFQ GRLLHLSAGQRLGVHLHTEARARHAWQLTQGATVLGLFRVGSGSGNGSQGMFAQLVAQNVLLIDGP LSWYSDPGLAGVSLTGGLSYKEDTKELVVAKAGVYYVFFQLELRRVVAGEGSGSVSLALHLQPLRS AAGAAALALTVDLPPASSEARNSAFGFQGRLLHLSAGQRLGVHLHTEARARHAWQLTQGATVLGLF RVGSGSGNGSQGMFAQLVAQNVLLIDGPLSWYSDPGLAGVSLTGGLSYKEDTKELVVAKAGVYYVF FQLELRRVVAGEGSGSVSLALHLQPLRSAAGAAALALTVDLPPASSEARNSAFGFQGRLLHLSAGQ RLGVHLHTEARARHAWQLTQGATVLGLFRVGSSSSSSSSGSCDKTHTCPPCPAPELLGGPSVFLFP PKPKDTLMISRTPEVTCVVVDVSHEDPEVKFNWYVDGVEVENAKTKPREEQYSSTYRVVSVLTVLH QDWLNGKEYKCKVSNKALPAPIEKTISKAKGQPREPQVYTLPPSREEMTKNQVSLTCLVKGFYPSD IAVEWESNGQPENNYKTTPPVLDSDGSFFLYSKLTVDKSRWQQGNVFSCSVMHEALHNHYTQKSLS LSPGSSSSSSAWSHPQFEK |
| 26 | CD137 L-wt + SEQ 14 | METDTLLVFVLLVWVPAGNGQGMFAQLVAQNVLLIDGPLSWYSDPGLAGVSLTGGLSYKEDTKELV VAKAGVYYVFFQLELRRVVAGEGSGSVSLALHLQPLRSAAGAAALALTVDLPPASSEARNSAFGFQ GRLLHLSAGQRLGVHLHTEARARHAWQLTQGATVLGLFRVGSGSGNGSQGMFAQLVAQNVLLIDGP LSWYSDPGLAGVSLTGGLSYKEDTKELVVAKAGVYYVFFQLELRRVVAGEGSGSVSLALHLQPLRS AAGAAALALTVDLPPASSEARNSAFGFQGRLLHLSAGQRLGVHLHTEARARHAWQLTQGATVLGLF RVGSGSGNGSQGMFAQLVAQNVLLIDGPLSWYSDPGLAGVSLTGGLSYKEDTKELVVAKAGVYYVF FQLELRRVVAGEGSGSVSLALHLQPLRSAAGAAALALTVDLPPASSEARNSAFGFQGRLLHLSAGQ RLGVHLHTEARARHAWQLTQGATVLGLFRVGSSSSSSSSGSCDKTHTCPPCPAPPVAGPSVFLFPP KPKDTLMISRTPEVTCVVVDVSHEDPEVKFNWYVDGVEVHNAKTKPREEQYNSTYRVVSVLTVLHQ DWLNGKEYKCKVSNKGLPSSIEKTISKAKGQPREPQVYTLPPSREEMTKNQVSLTCLVKGFYPDSI AVEWESNGQPENNYKTTPPVLDSDGSFFLYSKLTVDKSRWQQGNVFSCSVMHEALHNHYTQKSLSL SPGK |
| 27 | CD137 L-wt + SEQ 13 FC No Signal No Strep No Glyco | QGMFAQLVAQNVLLIDGPLSWYSDPGLAGVSLTGGLSYKEDTKELVVAKAGVYYVFFQLELRRVVA GEGSGSVSLALHLQPLRSAAGAAALALTVDLPPASSEARNSAFGFQGRLLHLSAGQRLGVHLHTEA RARHAWQLTQGATVLGLFRVGSGSGNGSQGMFAQLVAQNVLLIDGPLSWYSDPGLAGVSLTGGLSY KEDTKELVVAKAGVYYVFFQLELRRVVAGEGSGSVSLALHLQPLRSAAGAAALALTVDLPPASSEA RNSAFGFQGRLLHLSAGQRLGVHLHTEARARHAWQLTQGATVLGLFRVGSGSGNGSQGMFAQLVAQ NVLLIDGPLSWYSDPGLAGVSLTGGLSYKEDTKELVVAKAGVYYVFFQLELRRVVAGEGSGSVSLA LHLQPLRSAAGAAALALTVDLPPASSEARNSAFGFQGRLLHLSAGQRLGVHLHTEARARHAWQLTQ GATVLGLFRVGSSSSSSSSGSCDKTHTCPPCPAPELLGGPSVFLFPPKPKDTLMISRTPEVTCVVV DVSHEDPEVKFNWYVDGVEVHNAKTKPREEQYSSTYRVVSVLTVLHQDWLNGKEYKCKVSNKALPA PIEKTISKAKGQPREPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGK |
| 28 | Deglyco-Fc No Signal + StrepTag | QGMFAQLVAQNVLLIDGPLSWYSDPGLAGVSLTGGLSYKEDTKELVVAKAGVYYVFFQLELRRVVA GEGSGSVSLALHLQPLRSAAGAAALALTVDLPPASSEARNSAFGFQGRLLHLSAGQRLGVHLHTEA RARHAWQLTQGATVLGLFRVGSGSGNGSQGMFAQLVAQNVLLIDGPLSWYSDPGLAGVSLTGGLSY KEDTKELVVAKAGVYYVFFQLELRRVVAGEGSGSVSLALHLQPLRSAAGAAALALTVDLPPASSEA RNSAFGFQGRLLHLSAGQRLGVHLHTEARARHAWQLTQGATVLGLFRVGSGSGNGSQGMFAQLVAQ NVLLIDGPLSWYSDPGLAGVSLTGGLSYKEDTKELVVAKAGVYYVFFQLELRRVVAGEGSGSVSLA LHLQPLRSAAGAAALALTVDLPPASSEARNSAFGFQGRLLHLSAGQRLGVHLHTEARARHAWQLTQ GATVLGLFRVGSSSSSSSSGSCDKTHTCPPCPAPELLGGPSVFLFPPKPKDTLMISRTPEVTCVVV DVSHEDPEVKFNWYVDGVEVHNAKTKPREEQYSSTYRVVSVLTVLHWDWLNGKEYKCKVSNKALPA PIEKTISKAKGQPREPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGSSSSSSAWSHPQFEK |

TABLE 5-continued

Exemplary CD137 receptor agonist proteins

| SEQ ID NO | Sequence |
|---|---|
| 29<br>Glyco<br>FC<br>No Signal<br>No strep | QGMFAQLVAQNVLLIDGPLSWYSDPGLAGVSLTGGLSYKEDTKELVVAKAGVYYVFFQLELRRVVA<br>GEGSGGSVSLALHLQPLRSAAGAAALALTVDLPPASSEARNSAFGFQGRLLHLSAGQRLGVHLHTEA<br>RARHAWQLTQGATVLGLFRVGSGSGNGSQGMFAQLVAQNVLLIDGPLSWYSDPGLAGVSLTGGLSY<br>KEDTKELVVAKAGVYYVFFQLELRRVVAGEGSGSVSLALHLQPLRSAAGAAALALTVDLPPASSEA<br>RNSAFGFQGRLLHLSAGQRLGVHLHTEARARHAWQLTQGATVLGLFRVGSGSGNGSQGMFAQLVAQ<br>NVLLIDGPLSWYSDPGLAGVSLTGGLSYKEDTKELVVAKAGVYYVFFQLELRRVVAGEGSGSVSLA<br>LHLQPLRSAAGAAALALTVDLPPASSEARNSAFGFQGRLLHLSAGQRLGVHLHTEARARHAWQLTQ<br>GATVLGLFRVGSSSSSSSGSCDKTHTCPPCPAPPVAGPSVFLFPPKPKDTLMISRTPEVTCVVVD<br>VSHEDPEVKFNWYVDGVEVHNAKTKPREEQY<u>NS</u>TYRVVSVLTVLHQDWLNGKEYKCKVSNKGLPSS<br>IEKTISKAKGQPREPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| 30<br>SEQ<br>39 +<br>FC<br>13 Linker<br>21 | QLRQGMFAQLVAQNVLLIDGPLSWYSDPGLAGVSLTGGLSYKEDTKELVVAKAGVYYVFFQLELRR<br>VVAGEGSGSVSLALHLQPLRSAAGAAALALTVDLPPASSEARNSAFGFQGRLLHLSAGQRLGVHLH<br>TEARARHAWQLTQGATVLGLFRVGSGSGNGSDLRQGMFAQLVAQNVLLIDGPLSWYSDPGLAGVSL<br>TGGLSYKEDTKELVVAKAGVYYVFFQLELRRVVAGEGSGSVSLALHLQPLRSAAGAAALALTVDLP<br>PASSEARNSAFGFQGRLLHLSAGQRLGVHLHTEARARHAWQLTQGATVLGLFRVGSGSGNGSDLRQ<br>GMFAQLVAQNVLLIDGPLSWYSDPGLAGVSLTGGLSYKEDTKELVVAKAGVYYVFFQLELRRVVAG<br>EGSGSVSLALHLQPLRSAAGAAALALTVDLPPASSEARNSAFGFQGRLLHLSAGQRLGVHLHTEAR<br>ARHAWQLTQGATVLGLFRVGSSSSGSCDKTHTCPPCPAPELLGGPSVFLFPPKPKDTLMISRTPEV<br>TCVVVDVSHEDPEVKFNWYVDGVEVHNAKTKPREEQY<u>SST</u>YRVVSVLTVLHQDWLNGKEYKCKVSN<br>KALPAPIEKTISKAKGQPREPQVYTLPPSREEMTKNQVSLTCLVKGFYPSDIAVEWESNGQPENNY<br>KTTPPVLDSDGSFFLYSKLTVDKSRWQQGNVFSGSVMHEALHNHYTQKSLSLSPGK |
| 31 | QLRQGMFAQLVAQNVLLIDGPLSWYSDPGLAGVSLTGGLSYKEDTKELVVAKAGVYYVFFQLELRR<br>VVAGAGSGSVSLALHLQPLRSAAGAAALALTVDLPPASSEARNSAFGFQGRLLHLSAGQRLGVHLH<br>TEARARHAWQLTQGATVLGLFRVGSGSGNGSDLRQGMFAQLVAQNVLLIDGPLSWYSDPGLAGVSL<br>TGGLSYKEDTKELVVAKAGVYYVFFQLELRRVVAGEGSGSVSLALHLQPLRSAAGAAALALTVDLP<br>PASSEARNSAFGFQGRLLHLSAGQRLGVHLHTEARARHAWQLTQGATVLGLFRVGSGSGNGSDLRQ<br>GMFAQLVAQNVLLIDGPLSWYSDPGLAGVSLTGGLSYKEDTKELVVAKAGVYYVFFQLELRRVVAG<br>EGSGSVSLALHLQPLRSAAGAAALALTVDLPPASSEARNSAFGFQGRLLHLSAGQRLGVHLHTEAR<br>ARHAWQLTQGATVLGLFRVGSSSSSSSGSCDKTHTCPPCPAPELLGGPSVFLFPPKPKDTLMISR<br>TPEVTCVVVDVSHEDPEVKFNWYVDGVEVHNAKTKPREEQY<u>SST</u>YRVVSVLTVLHQDWLNGKEYKC<br>KVSNKALPAPIEKTISKAKGQPREPQVYTLPPSREEMTKNQVSLTCLVKGFYPSDIAVEWESNGQP<br>ENNYKTTPPVLDSDGSFFLYSKLTVDKSRWQQGNVFSCSVMHEALHNHYTQKSKSKSPGK |
| 32 | RQGMFAQLVAQNVLLIDGPLSWYSDPGLAGVSLTGGLSYKEDTKELVVAKAGVYYVFFQLELRRVV<br>AGEGSGSVSLALHLQPLRSAAGAAALALTVDLPPASSEARNSAFGFQGRLLHLSAGQRLGVHLHTE<br>ARARHAWQLTQGATVLGLFRVGSGSGNGSRQGMFAQLVAQNVLLIDGPLSWYSDPGLAGVSLTGGL<br>SYKEDTKELVVAKAGVYYVFFQLELRRVVAGEGSGSVSLALHLQPLRSAAGAAALALTVDLPPASS<br>EARNSAFGFQGRLLHLSAGQRLGVHLHTEARARHAWQLTQGATVLGLFRVGSGSGNGSRQGMFAQL<br>VAQNVLLIDGPLSWYSDPGLAGVSLTGGLSYKEDTKELVVAKAGVYYVFFQLELRRVVAGEGSGSV<br>SLALHLQPLRSAAGAAALALTVDLPPASSEARNSAFGFQGRLLHLSAGQRLGVHLHTEARARHAWQ<br>LTQGATVLGLFRVGSSSSGSCDKTHTCPPCPAPELLGGPSVFLFPPKPKDTLMISRTPEVTCVVV<br>DVSHEDPEVKFNWYVDGVEVHNAKTKPREEQY<u>SST</u>YRVVSVLTVLHQDWLNGKEYKCKVSNKALPA<br>PIEKTISKAKGQPREPQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPGK |
| 33 | QQGMFAQLVAQNVLLIDGPLSWYSDPGLAGVSLTGGLSYKEDTKELVVAKAGVYYVFFQLELRRVV<br>AGEGSGSVSLALHLQPLRSAAGAAALALTVDLPPASSEARNSAFGFQGRLLHLSAGQRLGVHLHTE<br>ARARHAWQLTQGATVLGLFRVGSGSGNGSgQGMFAQLVAQNVLLIDGPLSWYSDPGLAGVSLTGGL<br>SYKEDTKELVVAKAGVYYVFFQLELRRVVAGEGSGSVSLALHLQPLRSAAGAAALALTVDLPPASS<br>EARNSAFGFQGRLLHLSAGQRLGVHLHTEARARHAWQLTQGATVLGLFRVGSGSGNGSgQGMFAQL<br>VAQNVLLIDGPLSWYSDPGLAGVSLTGGLSYKEDTKELVVAKAGVYYVFFQLELRRVVAGEGSGSV<br>SLALHLQPLRSAAGAAALALTVDLPPASSEARNSAFGFQGRLLHLSAGQRLGVHLHTEARARHAWQ<br>LTQGATVLGLFRVGSSSSSSSGSCDKTHTCPPCPAPELLGGPSVFLFPPKPKDTLMISRTPEVTC<br>VVVDVSHEDPEVKFNWYVDGVEVHNAKTKPREEQ<u>SST</u>YRVVSVLTVLHQDWLNGKEYKCKVSNKA<br>LPAPIEKTISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGK |
| 34 | SQGMFAQLVAQNVLLIDGPLSWYSDPGLAGVSLTGGLSYKEDTKELVVAKAGVYYVFFQLELRRVV<br>AGEGSGSVSLALHLQPLRSAAGAAALALTVDLPPASSEARNSAFGFQGRLLHLSAGQRLGVHLHTE<br>ARARHAWQLTQGATVLGLFRVGSGSGNGSgQGMFAQLVAQNVLLIDGPLSWYSDPGLAGVSLTGGL<br>SYKEDTKELVVAKAGVYYVFFQLELRRVVAGEGSGSVSLALHLQPLRSAAGAAALALTVDLPPASS<br>EARNSAFGFQGRLLHLSAGQRLGVHLHTEARARHAWQLTQGATVLGLFRVGSGSGNGSgQGMFAQL<br>VAQNVLLIDGPLSWYSDPGLAGVSLTGGLSYKEDTKELVVAKAGVYYVFFQLELRRVVAGEGSGSV<br>SLALHLQPLRSAAGAAALALTVDLPPASSEARNSAFGFQGRLLHLSAGQRLGVHLHTEARARHAWQ<br>LTQGATVLGLFRVGSSSSSSSGSCDKTHTCPPCPAPELLGGPSVFLFPPKPKDTLMISRTPEVTC<br>VVVDVSHEDPEVKFNWYVDGVEVHNAKTKPREEQY<u>SST</u>YRVVSVLTVLHQDWLNGKEYKCKVSNKA<br>LPAPIEKTISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGK |

TABLE 5-continued

Exemplary CD137 receptor agonist proteins

| SEQ ID NO | Sequence |
|---|---|
| 35 (Seq 27 with additional glycol-sites) | QGMFAQLVAGNVLLIDGPLSWYSDPGLAGVSLTGGLSYKEDTKELVVAKAGVYYVFFQLELRRVVA GEGSGSVSLALHLQPLRSANGSAALALTVDLPPASSEARNSAFGFQGRLLHLSAGQRLGVHLHTEA RARHAWQLTQGATVLGLFRVGSGSGNGSQGMFAQLVAQNVLLIDGPLSWYSDPGLAGVSLTGGLSY KEDTKELVVAKAGVYYVFFQLELRRVVAGEGSGSVSLALHLQPLRSANGSAALALTVDLPPASSEA RNSAFGFQGRLLHLSAGQRLGVHLHTEARARHAWQLTQGATVLGLFRVGSGSGNGSQGMFAQLVAQ NVLLIDGPLSWYSDPGLAGVSLTGGLSYKEDTKELVVAKAGVYYVFFQLELRRVVAGEGSGSVSLA LHLQPLRSANGSAALALTVDLPPASSEARNSAFGFQGRLLHLSAGQRLGVHLHTEARAREAWQLTQ GATVLGLFRVGSSSSSSSGSCDKTHTCPPCPAPELLGGPSVFLFPPKPKDTLMISRTPEVTCVVV DVSHEDPEVKFNWYVDGVEVHNAKTKPREEQYSSTYRVVSVLTVLHQDWLNGKEYKCKVSNKALPA PIEKTISKAKGQPREPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGK |

TABLE 5B

Exemplary scCD137L-RBD modules

| | |
|---|---|
| 36 | QGMFAQLVAQNVLLIDGPLSWYSDPGLAGVSLTGGLSYKEDTKELVVAKAGVYYVFFQLELRRVVAGE GSGSVSLALHLQPLRSAAGAAALALTVDLPPASSEARNSAFGFQGRLLHLSAGQRLGVHLHTEARARH AWQLTQGATVLGLFRVGSGSGNGSQGMFAQLVAQNVLLIDGPLSWYSDPGLAGVSLTGGLSYKEDTKE LVVAKAGVYYVFFQLELRRVVAGEGSGSVSLALHLQPLRSAAGAAALALTVDLPPASSEARNSAFGFQ GRLLHLSAGQRLGVHLHTEARARHAWQLTQGATVLGLFRVGSGSGNGSQGMFAQLVAQNVLLIDGPLS WYSDPGLAGVSLTGGLSYKEDTKELVVAKAGVYYVFFQLELRRVVAGEGSGSVSLALHLQPLRSAAGA AALALTVDLPPASSEARNSAFGFQGRLLHLSAGQRLGVHLHTEARARHAWQLTQGATVLGLFRV |
| 39 | QLRQGMFAQLVAQNVLLIDGPLSWYSDPGLAGVSLIGGLSYKEDTKELVVAKAGVYYVFFQLELRRVV AGEGSGSVSLALHLQPLRSAAGAAALALTVDLPPASSEARNSAFGFQGRLLHLSAGQRLGVHLHTEAR ARHAWQLTQGATVLGLFRVGSGSGNGSDLRQGMFAQLVAQNVLLIDGPLSWYSDPGLAGVSLTGGLSY KEDTKELVVAKAGVYYVFFQLELRRVVAGFGSGSVSLALHLQPLRSAAGAAALALTVDLPPASSEARN SAFGFQGRLLHLSAGQRLGVHLHTEARARHAWQLTQGATVLGLFRVGSGSGNGSDLRQGMFAQLVAQN VLLIDGPLSWYSDPGLAGVSLTGGLSYKEDTKELVVAKAGVYYVFFQLELRRVVAGEGSGSVSLALHL QPLRSAAGAAALALTVDLPPASSEARNSAFGFQGRLLHLSAGQRLGVHLHTEARARHAWQLTQGATVL GLFRV |
| 40 | RQGMFAQLVAGNVLLIDGPLSWYSDPGLAGVSLTGGLSYKEDTKELVVAKAGVYYVFFQLELRRVVAG EGSGSVSLALHLQPLRSAAGAAALALTVDLPPASSEARNSAFGFQGRLLHLSAGQRLGVHLHTEARAR HAWQLTQGATVLGLFRVGSGSGNGSRQGMFAQLVAQNVLLIDGPLSWYSDPGLAGVSLTGGLSYKEDT KELVVAKAGVYYVFFQLELRRVVAGEGSGSVSLALHLQPLRSAAGAAALALTVDLPPASSEARNSAFG FQGRLLHLSAGQRLGVHLHTEARARHAWQLTQGATVLGLFRVGSGSGNGSRQGMFAQLVAGNVLLIDG PLSWYSDPGLAGVSLTGGLSYKEDTKELVVAKAGVYYVFFQLELRRVVAGEGSGSVSLALHLQPLRSA AGAAALALTVDLPPASSEARNSAFGFQGRLLHLSAGQRLGVHLHTEARARHAWQLTQGATVLGLFRV |
| 41 | QQGMFAQLVAGNVLLIDGPLSWYSDPGLAGVSLTGGLSYKEDTKELVVAKAGVYYVFFQLELRRVVAG EGSGSVSLALHLQPLRSAAGAAALALTVDLPPASSEARNSAFGFQGRLLHLSAGQRLGVHLHTEARAR HAWQLTQGATVLGLFRVGSGSGNGSgQGMFAQLVAQNVLLIDGPLSWYSDPGLAGVSLTGGLSYKEDT KELVVAKAGVYYVFFQLELRRVVAGEGSGSVSLALHLQPLRSAAGAAALALTVDLPPASSEARNSAFG FQGRLLHLSAGQRLGVHLHTEARARHAWQLTQGATVLGLFRVGSGSGNGSgQGMFAQLVAQNVLLIDG PLSWYSDPGLAGVSLTGGLSYKEDTKELVVAKAGVYYVFFQLELRRVVAGEGSGSVSLALHLQPLRSA AGAAALALTVDLPPASSEARNSAFGFQGRLLHLSAGQRLGVHLHTEARARHAWQLTQGATVLGLFRV |
| 42 | SQGMFAQLVAQNVLLIDGPLSWYSDPGLAGVSLTGGLSYKEDTKELVVAKAGVYYVFFQLELRRVVAG EGSGSVSLALHLQPLRSAAGAAALALTVDLPPASSEARNSAFGFQGRLLHLSAGQRLGVHLHTEARAR HAWQLTQGATVLGLFRVGSGSGNGSgQGMFAQLVAGNVLLIDGPLSWYSDPGLAGVSLTGGLSYKEDT KELVVAKAGVYYVFFQLELRRVVAGEGSGSVSLALHLQPLRSAAGAAALALTVDLPPASSEARNSAFG FQGRLLHLSAGQRLGVHLHTEARARHAWQLTQGATVLGLFRVGSGSGNGSgQGMFAQLVAQNVLLIDG PLSWYSDPGLAGVSLTGGLSYKEDTKELVVAKAGVYYVFFQLELRRVVAGEGSGSVSLALHLQPLRSA AGAAALALTVDLPPASSEARNSAFGFQGRLLHLSAGQRLGVHLHTEARARHAWQLTQGATVLGLFRV |
| 43 | QGMFAQLVAQNVLLIDGPLSWYSDPGLAGVSLTGGLSYKEDTKELVVAKAGVYYVFFQLELRRVVAGE GSGSVSLALHLQPLRSANGSAALALTVDLPPASSEARNSAFGFQGRLLHLSAGQRLGVHLHTEARARH AWQLTQGATVLGLFRVGSGSGNGSQGMFAQLVAGNVLLIDGPLSWYSDPGLAGVSLTGGLSYKEDTKE LVVAKAGVYYVFFQLELRRVVAGEGSGSVSLALHLQPLRSANGSAALALTVDLPPASSEARNSAFGFQ GRLLHLSAGQRLGVHLHTEARARHAWQLTQGATVLGLFRVGSGSGNGSQGMFAQLVAQNVLLIDGPLS WYSDPGLAGVSLTGGLSYKEDTKELVVAKAGVYYVFFQLELRRVVAGEGSGSVSLALHLQPLRSANGS AALALTVDLPPASSEARNSAFGFQGRLLHLSAGQRLGVHLHTEARARHAWQLTQGATVLGLFRV |

A further aspect of the present invention relates to a nucleic acid molecule encoding a CD137 receptor agonist protein as described herein. The nucleic acid molecule may be a DNA molecule, e.g. a double-stranded or single-stranded DNA molecule, or an RNA molecule. The nucleic acid molecule may encode the CD137 receptor agonist protein or a precursor thereof, e.g. a pro- or pre-proform of the CD137 receptor agonist protein which may comprise a signal sequence or other heterologous amino acid portions for secretion or purification which are preferably located at the N- and/or C-terminus of the CD137 receptor agonist protein. The heterologous amino acid portions may be linked to the first and/or second domain via a protease cleavage site, e.g. a Factor X3, thrombin or IgA protease cleavage site. A specific example of a nucleic acid sequence of the invention is shown in Table 6 as SEQ ID NO: 37. This nucleic acid molecule comprises the open reading frame encoding the fusion polypeptide of SEQ ID NO: 25.

A further aspect of the present invention relates to a pharmaceutical or diagnostic composition comprising as the active agent at least one CD137 receptor agonist protein, a respective nucleic acid encoding therefore, or a transformed or transfected cell, all as described herein.

In another aspect, the present invention provides a pharmaceutical composition comprising an CD137 receptor agonist protein disclosed herein and one or more pharmaceuti-

TABLE 6

Nucleic Acid Sequence of Exemplary CD137 receptor agonist protein

| SEQ ID NO | Sequence |
|---|---|
| 37 | AAGCTTTAGGGATAACAGGGTAATAGCCGCCACCATGGAGACTGACACCCTGCTGGTGTTCGTGCTGCT<br>GGTCTGGGTGCCTGCAGGAAATGGACAGGGCATGTTCGCTCAACTGGTCGCACAGAACGTGCTGCTCAT<br>TGACGGTCCCCTGTCTTGGTACTCCGATCCAGGGTTGGCAGGAGTGTCCTTGACAGGAGGGCTGTCCTA<br>TAAGGAGGATACCAAAGAGCTGGTGGTAGCAAAGGCTGGTGTGTATTACGTGTTCTTTCAGCTGGAGCT<br>GCGCAGAGTCGTCGCAGGCGAAGGATCTGGTAGTGTGTCACTGGCACTGCACTTGCAGCCCCTTCGGTC<br>CGCTGCCGGGGCAGCAGCACTGGCCCTGACCGTCGATCTGCCACCCGCTTCTAGCGAGGCACGAAACTC<br>AGCCTTTGGGTTTCAGGGTCGCCTGCTGCACCTGAGCGCCGGACAGAGGCTGGGCGTTCATCTGCACAC<br>CGAGGCCAGAGCCAGACACGCTTGGCAGTTGACTCAGGGAGCTACGGTCCTCGGTCTGTTTCGAGTAGG<br>CAGCGGAAGCGGCAATGGCTCTCAGGGCATGTTTGCTCAGCTGGTAGCCCAGAACGTACTCCTGATCGA<br>TGGCCCTCTTTCATGGTACTCAGACCCCGGACTGGCCGGAGTTAGCCTTACAGGTGGGCTTAGTTATAA<br>GGAGGACACAAAGGAATTGGTTGTGGCCAAAGCTGGCGTGTACTATGTGTTCTTCCAGCTTGAGCTCCG<br>CAGAGTCGTGGCTGGGGAGGGCTCTGGCAGTGTGAGCCTTGCCCTTCATCTGCAACCTTTGCGGAGCGC<br>AGCCGGCGCTGCTGCACTGGCCCTTACAGTGGATTTGCCACCCGCAAGTAGTGAAGCTCGCAATTCCGC<br>ATTCGGTTTCCAGGGCCGTCTGCTCCATCTTTCTGCCGGTCAACGTCTGGGAGTTCACCTCCACACTGA<br>GGCTAGGGCCAGGCATGCTTGGCAGCTGACTCAAGGAGCCACTGTCTTGGGACTCTTTCGGGTAGGCTC<br>CGGGTCTGGCAACGGCTCCCAGGGGATGTTTGCCCAACTGGTCGCCCAGAATGTCCTGCTCATCGATGG<br>TCCTCTGAGCTGGTATTCCGACCCTGGACTGGCTGGTGTGAGCCTGACTGGCGGACTCTCCTACAAAGA<br>GGACACCAAGGAACTGGTGGTGGCCAAAGCCGGGGTCTACTACGTGTTCTTCCAGTTGGAACTGCGGCG<br>GGTTGTGGCTGGCGAGGGATCAGGTTCCGTTAGTCTGGCCCTGCACCTCCAGCCTCTGAGGTCTGCTGC<br>TGGTGCCGCCGCTCTGGCCTTGACCGTCGACCTCCCACCCGCATCTTCCGAAGCCCGAAATTCAGCCTT<br>CGGGTTCCAGGGCAGACTGCTGCATCTGAGTGCTGGACAGCGCCTTGGGGTTCATCTCCACACCGAAGC<br>CAGGGCCCGACATGCCTGGCAGCTCACACAAGGCGCAACCGTTTTGGGGCTCTTTCGTGTGggatcctc<br>gagTTCATCGTCCTCATCCGGCTCATGTGATAAGACCCACACCTGCCCTCCCTGTCCTGCCCCTGAGCT<br>GCTGGGCGGACCTTCTGTGTTCCTGTTCCCCCCCAAGCCTAAGGACACCCTGATGATCTCCAGGACCCC<br>TGAGGTGACCTGTGTGGTGGTGGACGTGTCTCACGAAGATCCCGAGGTGAAGTTCAACTGGTACGTGGA<br>CGGCGTGGAGGTCCACAACGCCAAGACCAAGCCTAGGGAGGAGCAGTACAGCTCCACCTACCGGGTGGT<br>GTCTGTGCTGACCGTGCTGCACCAGGATTGGCTGAACGGAAAGGAGTATAAGTGTAAGGTCTCCAACAA<br>GGCCCTGCCTGCCCCCATCGAGAAAACCATCTCCAAGGCCAAGGGCCAGCCTCGGGAGCCTCAGGTGTA<br>CACCCTGCCTCCTAGCAGGGAGGAGATGACCAAGAACCAGGTGTCCCTGACCTGTCTGGTGAAGGGCTT<br>CTACCCTTCCGATATCGCCGTGGAGTGGGAGTCTAATGGCCAGCCCGAGAACAACTACAAGACCACCCC<br>TCCTGTGCTGGACTCTGACGGCTCCTTCTTCCTGTACTCCAAGCTGACCGTGGACAAGTCCAGATGGCA<br>GCAGGGCAACGTGTTCTCCTGCTCCGTGATGCACGAGGCCCTGCACAATCACTACACCCAGAAGTCCCT<br>GTCTCTGAGTCCGGGCAAGTAATAggcgcgcc |

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosomal integration vector, etc.

Examples of suitable expression control sequences and vectors are described for example by Sambrook et al. (1989) Molecular Cloning, A Laboratory Manual, Cold Spring Harbor Press, and Ausubel et al. (1989), Current Protocols in Molecular Biology, John Wiley & Sons or more recent editions thereof.

Various expression vector/host cell systems may be used to express the nucleic acid sequences encoding the CD137 receptor agonist proteins of the present invention. Suitable host cells include, but are not limited to, prokaryotic cells such as bacteria, e.g. E. coli, eukaryotic host cells such as yeast cells, insect cells, plant cells or animal cells, preferably mammalian cells and, more preferably, human cells. Further, the invention relates to a non-human organism transformed or transfected with a nucleic acid molecule as described above. Such transgenic organisms may be generated by known methods of genetic transfer including homologous recombination.

cally acceptable carriers, diluents, excipients, and/or adjuvants. In another aspect, the present invention provides a nucleic acid molecule encoding the CD137 receptor agonist protein. In another embodiment, the present invention provides an expression vector comprising the nucleic acid molecule. In another embodiment, the present invention provides a cell comprising the nucleic acid molecule. In a further embodiment, the cell is a eukaryotic cell. In another embodiment, the cell is a mammalian cell. In another embodiment, the cell is a Chinese Hamster Ovary (CHO) cell. In other embodiments, the cell is selected from the group consisting of CHO-DBX11, CHO-DG44, CHO-S, and CHO-K1 cells. In other embodiments, the cell is selected from the group consisting of Vero, BHK, HeLa, COS, MDCK, HEK-293, NIH-3T3, W138, BT483, Hs578T, HTB2, BT20, T47D, NSO, CRL7030, HsS78Bst, PER.C6, SP2/0-Agl4, and hybridoma cells.

In another aspect, the present invention provides a method of treating a subject having anCD137L-associated disease or disorder, the method comprising administering to the subject an effective amount of the CD137 receptor agonist protein. In one embodiment, the CD137 receptor agonist protein is administered alone. In another embodiment, the CD137 receptor agonist protein is administered before, concurrently, or after the administration of a second agent. In another embodiment, the disease or disorder is selected from the group consisting of: tumors, infectious diseases, inflammatory diseases, metabolic diseases, autoimmune disorders, degenerative diseases, apoptosis-associated diseases, and transplant rejections. In one embodiment, the tumors are solid tumors. In one embodiment, the tumors arise from the group of cancers consisting of sarcoma, esophageal cancer, and gastric cancer. In another embodiment, the tumors arise from Ewing's sarcoma or fibrosarcoma, In another embodiment, the tumors arise from the group of cancers consisting of Non-Small Cell Lung Carcinoma (NSCLC), pancreatic cancer, colorectal cancer, breast cancer, ovarian cancer, head and neck cancers, and Small Cell Lung Cancer (SCLC). In another embodiment, the tumors are lymphatic tumors. In one embodiment, the tumors are hematologic tumors. In another embodiment, the tumors arise from non-Hodgkin's lymphoma, leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), or hairy cell leukemia. In another embodiment, the autoimmune disorders are rheumatoid diseases, arthritic diseases, or rheumatoid and arthritic diseases. In a further embodiment, the disease or disorder is rheumatoid arthritis. In another embodiment, the degenerative disease is a neurodegenerative disease. In a further embodiment, the neurodegenerative disease is multiple sclerosis.

In one embodiment, the second agent is a chemotherapeutic, radiotherapeutic, or biological agent. In one embodiment, the second agent is selected from the group consisting of Duvelisib, Ibrutinib, Navitoclax, and Venetoclax, In another embodiment, the second agent is an apoptotic agent. In one embodiment, the apoptotic second agent is selected from the group consisting of Bortezomib, Azacitidine, Dasatinib, and Gefitinib. In a particular embodiment, the pharmaceutical compositions disclosed herein are administered to a patient by intravenous or subcutaneous administration. In other embodiments, the disclosed pharmaceutical compositions are administered to a patient byoral, parenteral, intramuscular, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal administration.

In one embodiment, the CD137 receptor agonist protein is administered as a single bolus. In another embodiment, CD137 receptor agonist protein may be administered over several divided doses. The CD137 receptor agonist protein can be administered at about 0.1-100 mg/kg. In one embodiment, the CD137 receptor agonist protein can be administered at a dosage selected from the group consisting of: about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, and 10-100 mg/kg. In other embodiments, the CD137 receptor agonist protein is present in pharmaceutical compositions at about 0.1-100 mg/ml. In one embodiment, the CD137 receptor agonist protein is present in pharmaceutical compositions at an amount selected from the group consisting of: about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml. In other embodiments, a therapeutically effective amount of CD137 receptor agonist protein is administered to a subject. In another embodiment, a prophylactically effective amount of CD137 receptor agonist protein is administered to a subject.

The term "CD137L-associated disease or disorder" as used herein is any disease or disorder which may be ameliorated by administering an effective amount of a CD137 receptor agonist to a subject in need thereof. At least one CD137 receptor agonist protein, respective nucleic acid encoding therefore, or transformed or transfected cell, all as described herein may be used in therapy, e.g., in the prophylaxis and/or treatment of disorders caused by, associated with and/or accompanied by dysfunction of CD137L, particularly proliferative disorders, such as tumors, e.g. solid or lymphatic tumors; infectious diseases; inflammatory diseases; metabolic diseases; autoimmune disorders, e.g. rheumatoid and/or arthritic diseases; degenerative diseases, e.g. neurodegenerative diseases such as multiple sclerosis; apoptosis-associated diseases or transplant rejections.

The term "dysfunction of CD137L" as used herein is to be understood as any function or expression of CD137L that deviates from the normal function or expression of CD137L, e.g., overexpression of the CD137L gene or protein, reduced or abolished expression of the CD137L gene or protein compared to the normal physiological expression level of CD137L, increased activity of CD137L, reduced or abolished activity of CD137L, increased binding of CD137L to any binding partners, e.g., to a receptor, particularly a CD137L receptor or another cytokine molecule, reduced or abolished binding to any binding partner, e.g. to a receptor, particularly a CD137L receptor or another cytokine molecule, compared to the normal physiological activity or binding of CD137L.

In various embodiments, a method is provided for diagnosing and/or treating a human subject suffering from a disorder which can be diagnosed and/or treated by targeting CD137L receptors comprising administering to the human subject a CD137 receptor agonist protein disclosed herein such that the effect on the activity of the target, or targets, in the human subject is agonistic, one or more symptoms is alleviated, and/or treatment is achieved. The CD137 receptor agonist proteins provided herein can be used to diagnose and/or treat humans suffering from primary and metastatic cancers, including carcinomas of breast, colon, rectum, lung (e.g., small cell lung cancer "SCLC" and non-small cell lung cancer "NSCLC"), oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), tumors arising from hematopoietic malignancies, acute leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), hairy cell leukemia, Hodgkin's and non-Hodgkin's lymphomas, DLBCL, follicular lymphomas, hematopoietic malignancies, Kaposi's sarcoma, malignant lymphoma, malignant histiocytosis, malignant melanoma, multiple myeloma, paraneoplastic syndrome/hypercalcemia of malignancy, or solid tumors.

A pharmaceutical composition comprising a CD137 receptor agonist protein disclosed herein and a pharmaceutically acceptable carrier is provided. In some embodiments, the pharmaceutical composition comprises at least one additional therapeutic agent for treating a disorder. For example, the additional agent may be a therapeutic agent, a chemotherapeutic agent; an imaging agent, a cytotoxic agent, an angiogenesis inhibitor, a kinase inhibitor (including but not limited to a KDR and a TIE-2 inhibitor), a co-stimulation molecule modulator or an immune checkpoint inhibitor (including but not limited to anti-B7.1, anti-B7.2, anti-B7.3, anti-B7.4, anti-CD28, anti-B7RP1, CTLA4-Ig, anti-CTLA-4, anti-PD-1, anti-PD-L1, anti-PD-L2, anti-ICOS, anti-LAG-3, anti-Tim3, anti-VISTA, anti-HVEM, anti-BTLA, LIGHT fusion protein, anti-CD137, anti-CD137L, anti-OX40, anti-OX40L, anti-CD70, anti-CD27, anti-CD27L, anti-GAL9, anti-A2AR, anti-KIR, anti-IDO-1, anti-CD20), a dendritic cell/antigen-presenting cell modulator (including but not limited to anti-CD40 antibody, anti-CD40L, anti-DC-SIGN, anti-Dectin-1, anti-CD301, anti-CD303, anti-CD123, anti-CD207, anti-DNGR1, anti-CD205, anti-DCIR, anti-CD206, anti-ILT7), a modulator for Toll-like receptors (including but not limited to anti-TLR-1, anti-TLR-2, anti-TLR-3, anti-TLR-4, anti-TLR-4, anti-TLR-5, anti-TLR-6, anti-TLR-7, anti-TLR-8, anti-TLR-9), an adhesion molecule blocker (including but not limited to an anti-LFA-1 antibody, an anti-E/L selectin antibody, a small molecule inhibitor), an anti-cytokine antibody or functional fragment thereof (including but not limited to an anti-IL-18, an anti-TNF, or an anti-IL-6/cytokine receptor antibody), a bispecific redirected T cell or NK cell cytotoxicity (including but not limited to a BiTE®), a chimeric T cell receptor (CAR-T) based therapy, a T cell receptor (TCR)-based therapy, a therapeutic cancer vaccine, methotrexate, cyclosporin, rapamycin, FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

In an embodiment, a method of treating a cancer or in the prevention or inhibition of metastases from the tumors described herein, the CD137 receptor agonist protein(s) can be used alone or in combination with one or more additional agents, e.g., a chemotherapeutic, radiotherapy, or biological agent. In some embodiments, the agent can include the following:13-cis-Retinoic Acid; 2-CdA; 2-Chlorodeoxyadenosine; 5-Azacitidine; 5-Fluorouracil; 5-FU; 6-Mercaptopurine; 6-MP; 6-TG; 6-Thioguanine; Abraxane; Accutane®; Actinomycin-D; Adriamycin®; Adrucil®; Afinitor®; Agrylin®; Ala-Corte; Aldesleukin; Alemtuzumab; ALIMTA; Alitretinoin; Alkaban-AQ®; Alkeran®; All-transretinoic Acid; Alpha Interferon; Altretamine; Amethopterin; Amifostine; Aminoglutethimide; Anagrelide; Anandron®; Anastrozole; Arabinosylcytosine; Ara-C Aranesp®; Aredia®; Arimidex®; Aromasin®; Arranon®; Arsenic Trioxide; Arzerra™; Asparaginase; ATRA; Avastin®; Azacitidine; BCG; BCNU; Bendamustine; Bevacizumab; Bexarotene; BEXXAR®; Bicalutamide; BiCNU; Blenoxane®; Bleomycin; Bortezomib; Busulfan; Busulfex®; C225; Calcium Leucovorin; Campath®; Camptosar®; Camptothecin-11; Capecitabine Carac™; Carboplatin; Carmustine; Carmustine Wafer; Casodex®; CC-5013; CCI-779; CCNU; CDDP; CeeNU; Cerubidine®; Cetuximab; Chlorambucil; Cisplatin; Citrovorum Factor; Cladribine; Cortisone; Cosmegen®; CPT-11; Cyclophosphamide; Cytadren®; Cytarabine; Cytarabine Liposomal; Cytosar-U®; Cytoxan®; Dacarbazine; Dacogen; Dactinomycin; Darbepoetin Alfa; Dasatinib; Daunomycin; Daunorubicin; Daunorubicin Hydrochloride; Daunorubicin Liposomal; DaunoXome®; Decadron; Decitabine; Delta-Cortef®; Deltasone®; Denileukin; Diftitox; DepoCyt™; Dexamethasone; Dexamethasone Acetate; Dexamethasone Sodium Phosphate; Dexasone; Dexrazoxane; DHAD; DIC; Diodex; Docetaxel; Doxil®; Doxorubicin; Doxorubicin Liposomal; Droxia™; DTIC; DTIC-Dome®; Duralone®; Duvelisib; Efudex®; Eligard™; Ellence™; Eloxatin™; Elspar®; Emcyt®; Epirubicin; Epoetin Alfa; Erbitux; Erlotinib; Erwinia L-asparaginase; Estramustine; Ethyol Etopophos®; Etoposide; Etoposide Phosphate; Eulexin®; Everolimus; Evista®; Exemestane; Fareston®; Faslodex®; Femara® Filgrastim; Floxuridine; Fludara®; Fludarabine; Fluoroplex®; Fluorouracil; Fluorouracil (cream); Fluoxymesterone; Flutamide; Folinic Acid; FUDR®; Fulvestrant; Gefitinib; Gemcitabine; Gemtuzumab ozogamicin; Gemzar; Gleevec™; Gliadel® Wafer; GM-CSF; Goserelin; Granulocyte-Colony Stimulating Factor (G-CSF); Granulocyte Macrophage Colony Stimulating Factor (G-MCSF); Halotestin®; Herceptin®; Hexadrol; Hexalen®; Hexamethylmelamine; HMM; Hycamtin®; Hydrea®; Hydrocort Acetate®; Hydrocortisone; Hydrocortisone Sodium Phosphate; Hydrocortisone Sodium Succinate; Hydrocortone Phosphate; Hydroxyurea; Ibrutinib; Ibritumomab; Ibritumomab Tiuxetan; Idamycin®; Idarubicin Ifex®; Interferon-alpha; Interferon-alpha-2b (PEG Conjugate); Ifosfamide; Interleukin-11 (IL-11); Interleukin-2 (IL-2); Imatinib mesylate; Imidazole Carboxamide; Intron A®; ipilimumab, Iressa®; Irinotecan; Isotretinoin; Ixabepilone; Ixempra™; KADCYCLA®; Kidrolase (t) Lanacort®; Lapatinib; L-asparaginase; LCR; Lenalidomide; Letrozole; Leucovorin; Leukeran; Leukine™; Leuprolide; Leurocristine; Leustatin™; Lirilumab; Liposomal Ara-C; Liquid Pred®; Lomustine; L-PAM; L-Sarcolysin; Lupron®; Lupron Depot® Matulane®; Maxidex; Mechlorethamine; Mechlorethamine Hydrochloride; Medralone®; Medrol®; Megace®; Megestrol; Megestrol Acetate; MEK inhibitors; Melphalan; Mercaptopurine; Mesna; Mesnex™; Methotrexate; Methotrexate Sodium; Methylprednisolone; Meticorten®; Mitomycin; Mitomycin-C; Mitoxantrone M-Prednisol®; MTC; MTX; Mustargen®; Mustine; Mutamycin®; Myleran®; Mylocel™; Mylotarg®; Navitoclax; Navelbine®; Nelarabine; Neosar®; Neulasta™; Neumega®; Neupogen®; Nexavar®; Nilandron®; Nilotinib; Nilutamide; Nipent®; Nitrogen Mustard Novaldex®; Nivolumab; Novantrone®; Nplate; Octreotide; Octreotide acetate; Ofatumumab; Oncospar®; Oncovin®; Ontak®; Onxal™; Oprelvekin; Orapred®; Orasone®; Oxaliplatin; Paclitaxel; Paclitaxel Protein-bound; Pamidronate; Panitumumab; Panretin®; Paraplatin®; Pazopanib; Pediapred®; PEG Interferon; Pegaspargase; Pegfilgrastim; PEG-INTRON™; PEG-L-asparaginase; PEMETREXED; Pembrolizumab; Pentostatin; Pertuzumab; Phenylalanine Mustard; Pidilizumab; Platinol®; Platinol-AQ®; Prednisolone; Prednisone; Prelone®; Procarbazine; PROCRIT®; Proleukin®; Prolifeprospan 20 with Carmustine Implant; Purinethol®; BRAF inhibitors; Raloxifene; Revlimid®; Rheumatrex®; Rituxan®; Rituximab; Roferon-A®; Romiplostim;

Rubex®; Rubidomycin hydrochloride; Sandostatin®; Sandostatin LAR®; Sargramostim; Solu-Cortef®; Solu-Medrol®; Sorafenib; SPRYCEL™; STI-571; STIVAGRA™; Streptozocin; SU11248; Sunitinib; Sutent®; Tamoxifen Tarceva®; Targretin®; Tasigna®; Taxol®; Taxotere®; Temodar®; Temozolomide Temsirolimus; Teniposide; TESPA; Thalidomide; Thalomid®; TheraCys®; Thioguanine; Thioguanine Tabloid®; Thiophosphoamide; Thioplex®; Thiotepa; TICE®; Toposar®; Topotecan; Toremifene; Torisel®; Tositumomab; Trastuzumab; Treanda®; Tremelimumab; Tretinoin; Trexall™; Trisenox®; TSPA; TYKERB®; Urelumab; VCR; Vectibix™; Velban®; Velcade®; Venetoclax; VePesid®; Vesanoid®; Viadur™; Vidaza®; Vinblastine; Vinblastine Sulfate; Vincasar Pfs®; Vincristine; Vinorelbine; Vinorelbine tartrate; VLB; VM-26; Vorinostat; Votrient; VP-16; Vumon®; Xeloda®; Zanosar®; Zevalin™; Zinecard®; Zoladex®; Zoledronic acid; Zolinza; or Zometa®, and/or any other agent not specifically listed here that target similar pathways.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more than one, or all of the substances or principles to be administered, while still achieving the desired therapeutic action. This may, e.g., be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In various embodiments, pharmaceutical compositions comprising one or more CD137 receptor agonist proteins, either alone or in combination with prophylactic agents, therapeutic agents, and/or pharmaceutically acceptable carriers are provided herein. In various embodiments, nonlimiting examples of the uses of the pharmaceutical compositions disclosed herein include diagnosing, detecting, and/or monitoring a disorder, preventing, treating, managing, and/or ameliorating a disorder or one or more symptoms thereof, and/or in research. The formulation of pharmaceutical compositions, either alone or in combination with prophylactic agents, therapeutic agents, and/or pharmaceutically acceptable carriers, are known to one skilled in the art (US Patent Publication No. 20090311253 A1).

As used herein, the phrase "effective amount" means an amount of CD137L agonist protein that results in a detectable improvement (e.g., at least about 5%, 10%, 15%, 20%, 25%, 30%, 35%, 40%, 45%, 50%, 55%, 60%, 65%, 70%, 75%, or more from baseline) in one or more parameters associated with a dysfunction of CD137L or with a CD137L-associated disease or disorder.

Methods of administering a therapeutic agent provided herein include, but are not limited to, oral administration, parenteral administration (e.g., intradermal, intramuscular, intraperitoneal, intravenous and subcutaneous), epidural administration, intratumoral administration, mucosal administration (e.g., intranasal and oral routes) and pulmonary administration (e.g., aerosolized compounds administered with an inhaler or nebulizer). The formulation of pharmaceutical compositions for specific routes of administration, and the materials and techniques necessary for the various methods of administration are available and known to one skilled in the art (US Patent Publication No. 20090311253 A1).

In various embodiments, dosage regimens may be adjusted to provide for an optimum desired response (e.g., a therapeutic or prophylactic response). For example, a single bolus may be administered, several divided doses may be administered over time or the dose may be proportionally reduced or increased as indicated by the exigencies of the therapeutic situation. In some embodiments, parenteral compositions are formulated in dosage unit form for ease of administration and uniformity of dosage. The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier.

An exemplary, non-limiting range for a therapeutically or prophylactically effective amount of a CD137 receptor agonist protein provided herein is about 0.1-100 mg/kg, (e.g., about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, or 10-100 mg/kg, or any concentration in between). In some embodiments, the CD137 receptor agonist protein is present in a pharmaceutical composition at a therapeutically effective concentration, e.g., a concentration of about 0.1-100 mg/ml (e.g., about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml, or any concentration in between). Note that dosage values may vary with the type and/or severity of the condition to be alleviated. It is to be further understood that for any particular subject, specific dosage regimens may be adjusted over time according to the individual need and/or the professional judgment of the person administering or supervising the administration of the compositions, and that dosage ranges set forth herein are exemplary only and are not intended to limit the scope or practice of the claimed composition.

EXAMPLES 1.1 Polypeptide Structure
A) Amino acids Met1-Gly20
   Ig-Kappa-signal peptide, assumed signal peptidase cleavage site after amino acid Gly 20.
B) Amino acids Gln21-Val172
   First soluble cytokine domain of the human CD137L ligand (CD137L, amino acid 89-240 of SEQ ID NO: 1).
C) Amino acids Gly173-Ser 180
   First peptide linker element of SEQ ID NO: 2.
D) Amino acids Gln181-Val332
   Second soluble cytokine domain of the human CD137L ligand (CD137L, amino acid 89-240 of SEQ ID NO: 1).
E) Amino acids Gly333-Ser340.
   Second peptide linker element of SEQ ID NO: 2.
F) Amino acids Gln341-Val492
   Third soluble cytokine domain of the human CD137L ligand (CD137L, amino acid 89-240 of SEQ ID NO: 1).
G) Amino acids Gly493-Cys513
   Hinge-linker element of SEQ ID NO: 16.
H) Amino acids Pro514-Lys731
   Antibody Fc fragment domain of SEQ ID NO: 13.

The above CD137 receptor agonist protein is shown in SEQ ID NO: 25.

The indicated linkers may be replaced by other preferred linkers, e.g. as shown in SEQ ID NOs: 3-12.

The indicated Hinge-linker element may be replaced by other preferred Hinge-linkers, e.g. as shown in SEQ ID NOs: 19-24.

It should be noted that the first and second peptide linkers do not need to be identical.

The signal peptide sequence (A) may be replaced by any other suitable, e.g. mammalian signal peptide sequence.

1.2 Gene Cassette Encoding the Polypeptide

The synthetic gene may be optimized in view of its codon usage for the expression in suitable host cells, e.g. insect cells or mammalian cells. A preferred nucleic acid sequence is shown in SEQ ID NO: 37.

Example 2. Expression and Purification 2.1 Cloning, Expression and Purification of Fusion Polypeptides The aforementioned fusion proteins are expressed recombinantly in different eukaryotic host cells employing the methods described below:

Method for Small Scale Expression of CD137 Receptor Agonist Fusion Proteins:

For small scale analysis of aforementioned CD137 receptor agonist fusion proteins, Hek293 cells are grown in DMEM+GlutaMAX (GibCo) supplemented with 10% FBS, 100 units/ml Penicillin and 100 [mu]g/ml Streptomycin and are transiently transfected with a plasmid containing an expression cassette for a fusion polypeptide and an appropriate selection marker, e.g. a functional expression cassette comprising a blasticidine, puromycin or hygromycin resistence gene. In those cases, where a plurality of polypeptide chains is necessary to achieve the final product, the expression cassettes are either combined on one plasmid or positioned on different plasmids during the transfection. Cell culture supernatant containing recombinant fusion polypeptide are harvested three days post transfection and clarified by centrifugation at 300×g followed by filtration through a 0.22 μm sterile filter.

Method for Large Scale Expression and Purification of CD137 Receptor Agonist Fusion Proteins For larger scale expression of CD137 receptor agonist fusion proteins, synthetic DNA cassettes encoding the aforementioned proteins are inserted into eukaryotic expression vectors comprising appropriate selection markers (e.g. a functional expression cassette comprising a blasticidin, puromycin or hygromycin resistance gene) and genetic elements suitable to enhance the number of transcriptionally active insertion sites within the host cells genome. The sequence verified expression vectors is introduced by electroporation into suspension adapted Chinese Hamster Ovary cells (CHO-S, Invitrogen). Appropriate selection pressure will be applied three days post-transfection to transfected cells. Surviving cells carrying the vector derived resistance gene(s) are recovered by subsequent cultivation under selection pressure. Upon stable growth of the selected cell pools in chemically defined medium (PowerCHO2-CD, Lonza) at 37° C. and 7% CO2 atmosphere in an orbital shaker incubator (100 rpm, 50 mm shaking throw), the individual supernatants are analyzed by ELISA-assays detecting the aforementioned proteins and the cell pools with the highest specific productivity are expanded in shake flasks prior to protein production (orbital shaker, 100 rpm, shaking throw 50 mm).

For lab-scale protein production, individual cell pools are cultured for 7-12 days in chemically defined medium (PowerCHO2-CD, Lonza) at 37° C. and 7% CO2 atmosphere in a Wave bioreactor 20/50 EHT (GE-Healthcare). The basal medium is PowerCHO2-CD supplemented with 4 mM Glutamax. Wave culture is started with a viable cell concentration of 0.3 to 0.4×10e6 cells/ml and the following settings (for a five- or ten liter bag): shaking frequency 18 rpm, shaking ankle 7°, gas current 0.2-0.3 L/min, 7% CO2, 36.5° C. During the Wave run, the cell culture is fed twice with PowerFeed A (Lonza), usually on day 2 (20% feed) and day 5 (30% feed). After the second feed, shaking frequency is increased to 22 rpm, as well as the shaking ankle to 8°.

The bioreactor is usually harvested in between day 7 to day 12 when the cell viability drops below 80%. First, the culture supernatant is clarified using a manual depth filtration system (Millipore Millistak Pod, MCOHC 0.054 m²). For Strep-tagged proteins, Avidin is added to a final concentration of 0.5 mg/L. Finally, the culture supernatant containing the CD137 receptor agonist fusion protein is sterile filtered using a bottle top filter (0.22 μm, PES, Corning) and stored at 2-8° C. until further processing.

For affinity purification Streptactin Sepharose is packed to a column (gel bed 2 ml), equilibrated with 15 ml buffer W (100 mM Tris-HCl, 150 mM NaCl, pH 8.0) or PBS pH 7.4 and the cell culture supernatant is applied to the column with a flow rate of approx. 4 ml/min. Subsequently, the column is washed with 15 ml buffer W and bound polypeptide is eluted stepwise by addition of 7×1 ml buffer E (100 mM Tris HCl, 150 mM NaCl, 2.5 mM Desthiobiotin, pH 8.0). Alternately, PBS pH 7.4 containing 2.5 mM Desthiobiotin can be used for this step.

Alternately to the Streptactin Sepharose based method, the affinity purification is performed employing a column with immobilized Protein-A as affinity ligand and an Akta chromatography system (GE-Healthcare). A solid phase material with high affinity for the FC-domain of the fusion protein is chosen: MABSelect Sure™ (GE Healthcare). Briefly, the clarified cell culture supernatant is loaded on a HiTrap MabSelectSure column (CV=5 ml) equilibrated in wash-buffer-1 (20 mM Pi, 95 mM NaCl, pH7.2) not exceeding a load of 10 mg fusion protein per ml column-bed. The column is washed with ten column-volumes (10CV) of aforementioned equilibration buffer followed by four column-volumes (4CV) of wash-buffer-2 (20 mM Pi, 95 mM NaCl, pH 8.0) to deplete host-cell protein and host-cell DNA. The column is then eluted with elution buffer (20 mM Pi, 95 mM NaCl, pH 3.5) and the eluate is collected in up to ten fractions with each fraction having a volume equal to column-bed volume (5 ml). Each fraction is neutralized with an equal volume of aforementioned wash-buffer-2. The linear velocity is set to 150 cm/h and kept constant during the aforementioned affinity chromatography method.

The protein amount of the eluate fractions is quantitated and peak fractions are concentrated by ultrafiltration and further purified by size exclusion chromatography (SEC).

SEC is performed on Superdex 200 10/300 GL or HiLoad 26/60 columns using an Akta chromatography system (GE-Healthcare). The columns are equilibrated with phosphate buffered saline and the concentrated, affinity-purified polypeptide is loaded onto the SEC column with the sample volume not exceeding 2% (v/v) of the column-volume. In the case of Superdex 200 10/300 GL columns (GE Healthcare), a flow rate of 0.5 ml per minute is applied. In the case of HiLoad 26/60 Superdex200 columns, a flow rate of 2.5 ml per minute is applied. The elution profile of the polypeptide is monitored by absorbance at 280 nm.

For determination of the apparent molecular weight of purified fusion polypeptide under native conditions a Superdex 200 column is loaded with standard proteins of known molecular weight. Based on the elution volume of the standard proteins a calibration curve is plotted and the molecular weight of purified fusion polypeptide is determined. The FC-domain comprising CD137 receptor agonist fusion proteins elutes from the Superdex200 columns with an apparent molecular weight of approx. 140-180 kDa, which would confirm the homodimerization of the mature CD137 receptor agonist fusion polypeptide by the Fc domain.

Example 3: Trivalent Control Protein

To compare the relative binding between hexavalent CD137 receptor agonist fusion proteins and the, homo-trimeric trivalent CD137 receptor agonist fusion proteins stabilized with bacteriophage RB69-FOLDON is expressed in CHO-S cells and purified as described in the former section. The sequence is shown in the table below:

| SEQ ID NO | Sequence |
|---|---|
| 38 (Trivalent control protein) | METDTLLVFVLLVWVPAGNGQGMFAQLVAQNVLLIDGPL SWYSDPGLAGVSLTGGLSYKEDTKELVVAKAGVYYVFFQ LELRRVVAGAGSGSVSLALHLQPLRSAAGAAALALTVDL PPASSEARNSAFGFQGRLLHLSAGQRLGVHLHTEARARH AWQLTQGATVLGLFRVGSGSSGSSGSSGSGYIEDAPSDG KFYVRKDGAWVELPTASGPSSSSSSAWSHPQFEK. |

Example 4: Determination of the In Vitro Stability of CD137 Receptor Agonist Proteins by Limited Protease Digestion All CD137 receptor agonist proteins to be investigated will be expressed and purified as hexavalent Fc-Fusion protein as described in Example 1. The set will include CD137 receptor agonist proteins comprising the N297S mutation [according to the EU numbering system] in the CH2-domain and a hinge region that enables the formation of three disulfide bridges and additionally lack the upper hinge lysine [K223, according to the EU numbering system] which is mutated to glycine [K223G]. In a limited protease digestion assay, the aforementioned CD137 receptor agonist proteins comprising the N297S mutation and the K223G mutation simultaneously in context of a three disulfide enabling hinge will be compared to CD137 receptor agonist proteins comprising the N297S mutation but have the K223 wildtype present either in the context of a two disulfide or three disulfide enabling hinge region.

In addition CD137 receptor agonist proteins with the second linker element (iv) reduced to 4 amino-acids and the shortened hinge element (vi) will be investigated (e.g. SEQ ID NO: 32 and 34). Both engineering strategies (N297S combined with K223G mutation in context of a three disulfide enabling hinge region) and shortage of linker elements (iv and vi) have a potential impact on the stability of the respective molecules.

The stability of different CD137 agonistic proteins of the present invention can be addressed by limited protease digestion in vitro. For this analysis, the aforementioned CD137 receptor agonist proteins are incubated with low concentrations of proteases (e.g. Trypsin, V8 protease) at different temperatures (e.g. 4° C., 25° C., 37° C.) for different amounts of time. Quantification of specific proteolytic fragments and their appearance over time can be subsequently measured by different methods, like SDS-PAGE, analytical SEC or analytical Mass-Spectrometry methods known in the art (e.g Nano-RP-HPLC-ESI-MSMS). As the investigated proteins have most of their sequences in common, the faster appearance and enlarged quantities of specific proteolytic fragments from individual proteins over time can then be used to judge their relative stability and rank them to each other. With regard to protease based decoy kinetics of the aforementioned CD137 receptor agonist proteins investigated, the following order regarding their proteolytic stability is to be expected:

The CD137 receptor agonist proteins comprising the N297S and the K223G and the three disulfide enabling hinge region simultaneously have a prolonged stability as compared to the CD137 receptor agonist proteins comprising the N297S and wildtype K223 in the hinge region. The CD137 receptor agonist proteins comprising the SEQ ID NO: 21 as hinge linker have a prolonged stability as compared to CD137 receptor agonist proteins comprising the SEQ ID NO: 16 as hinge linker element.

Example 5: Stability/Aggregation Test

The contents of monomers and aggregates are determined by analytical SEC as described in Example 2. For this particular purpose the analysis is performed in buffers containing physiological salt concentrations at physiological pH (e.g. 0.9% NaCl, pH 7.4; PBS pH 7.4). A typical aggregation analysis is done on a Superdex200 column (GE Healthcare). This column separates proteins in the range between 10 to 800 kDa.

For determination of the apparent molecular weight of purified fusion polypeptide under native conditions a Superdex 200 column is loaded with standard proteins of known molecular weight. Based on the elution volume of the standard proteins a calibration curve is plotted and the apparent molecular weight of purified fusion proteins of unknown molecular weight is calculated based on the elution volume.

SEC analysis of soluble, non-aggregated protein typically shows a distinct single protein peak at a defined elution volume (measured at OD at 280 nm or at OD 214 nm). This elution volume corresponds to the apparent native molecular weight of the particular protein. With regard to the definition of "monomer" in the case of FC-fusion proteins, the assembly of two polypeptide-chains is driven by the FC-part of the protein and the functional unit is a protein consisting of two chains. This unit that contains two FC-linked polypeptide chains is defined as "monomer" in the case of Fc-fusion proteins regardless of being a dimerized single-chain fusion polypeptide.

If protein aggregation occurs, the SEC analysis shows additional protein peaks with lower retention volumes. Protein oligomers potentially serve as aggregation seeds and a high content of oligomers potentially leads to aggregation of the protein. Oligomers of large molecular weight and aggregates elute in the void volume of the Superdex200 column and cannot be analyzed by SEC with respect to their native molecular weight.

Purified preparations of CD137 receptor agonist fusion proteins should preferably contain only defined monomeric protein and only a very low amount of oligomeric protein. The degree of aggregation/oligomerization of a particular CD137 receptor agonist fusion protein preparation is determined on basis of the SEC analysis by calculating the peak areas of the OD280 diagram for the defined monomer and the oligomer/aggregate fraction, respectively. Based on the total peak area the percentage of defined monomer protein is calculated as follows:

monomer content [%]=[Peak area monomer protein]/ [Total peak area]×100)

Example 6: Determination of the Equilibrium Binding Constants for Tri- and Hexavalent CD137 Receptor Ligand Constructs by QCM Analysis The equilibrium binding constants ($K_D$) of trivalent and hexavalent constructs of CD137 receptor ligand are calculated based on kinetic binding data ($k_{on}$ and $k_{off}$) that are determined with an automated biosensor system (Attana A100). The A100 allows to investigate molecular interactions in real-time based on the Quartz Crystal Microbalance (QCM) technique.

For this purpose the human CD137 receptor is immobilized to the surface of a carboxyl-activated QCM-chip. Subsequently the tri- or hexavalent CD137 receptor ligand, respectively, is used as an analyte at different concentrations (e.g. 0.5, 1, 2, 5, and 10 µg/ml) for analyzing the kinetic binding data for ligand-receptor binding ($k_{on}$) and dissociation ($k_{off}$). The analysis is done in real time and the respective $K_D$ can be calculated: $K_D=k_{off}/k_{on}$.

The QCM analysis shows that the trivalent CD137 receptor ligand binds to the respective immobilized CD137 receptor with a KD in the low nM-range with an expected $K_D$ of 1-500 nM. However, hexavalent constructs of CD137 receptor ligand show a higher binding affinity in the pM-range towards the respective immobilized CD137 receptor with an expected $K_D$ of 1 pM-500 nM. A common characteristic of the kinetic binding data ($k_{on}$ and $k_{off}$) is that the hexavalent constructs show faster $k_{on}$ in comparison to the trivalent constructs. In addition slower dissociation ($k_{off}$) is commonly observed for the hexavalent ligands if compared to the trivalent ligand.

Example 7: T Cell Proliferation Assay

To assess the T cell activation capability of the CD137 receptor agonist, T cells are purified from human buffy coat preparations by negative selection using magnetic beads. Cells are labeled with CFSE and incubated with or without varying amounts of the CD137 receptor agonist and combined with an anti-human CD3 antibody for 2-5 days at 37° C. Data on CFSE dilution as a means to measure cell division is acquired on a flow cytometer. IFNγ production is measured by an ELISA assay using cell culture supernatants and an anti-human IFNγ antibody for capture.

One expects to observe a clear augmentation of IFNγ secretion by both CD4+ and CD8+ T cells when the CD137 receptor agonist is present in the T cell cultures along with the anti-human CD3 antibody. As well as higher IFNγ production one expects to see more T cells to be driven into cell cycle by measuring CFSE dilution using flow cytometry. This would demonstrate a co-stimulatory effect of the CD137 receptor agonist in the context of T cell activation.

Example 8: CD137 Agonist Binding Assay

Primary, human T cells are isolated from fresh buffy coat preparations using negative selection and magnetic beads. Cells are seeded into 24-well plates at 2×10e6 cells per well. T cells are incubated with an anti-human CD3 antibody (clone HIT3a, 1 µg/ml), anti-human CD28 antibody (clone CD28.2, 5 µg/ml) and varying amounts of Protein A (CD137L, 10-1000 ng/ml) or simply left in medium as control. After 3 days at 37° C. cells are fluorescently labeled with anti-human CD137 and anti-human CD4 or anti-human CD8 antibodies. CD137 fluorescence is assessed on a guava easyCyte flow cytometer within CD4+ and CD8+ T cell populations.

When comparing T cell populations incubated with anti-CD3 and anti-CD28 antibodies to control cells left in medium alone, one expects to observe a lower flourescent signal for CD137 indicating an activation-induced down-regulation of the receptor. This effect can be stronger and dose-dependent, when cells are co-incubated with the CD137 agonist (Protein A), which indicates a supplementary effect caused by the CD137 agonist (Protein A). Such results would suggest a binding of the CD137 agonist (Protein A) to its receptor in vitro.

Example 9: Human In Vitro T Cell Proliferation Assay

Total T cells (human) purified by negative selection and magnetic beads (pan T cell isolation kit, Miltenyi Biotec) from the peripheral blood of healthy donors and stained with CFSE (CellTrace™ CFSE Cell Proliferation Kit, for flow cytometry, ThermoFisher) and seeded into 24-well plates at 2×10e6 cells per well. Cells were incubated at 37° C. for 5 days with media alone, soluble anti-CD3 antibody (clone OKT3 at 1 µg/ml) alone, anti-CD3 antibody plus anti-CD28 antibody (clone 28.2 at 1 µg/ml) or anti-CD3 antibody plus mature Protein A (SEQ ID NO: 27) at 10, 100 or 1000 ng/ml, respectively.

On day 5, cells were washed and stained with DAPI (to exclude dead cells) and specific antibodies. Expression of Forward Scatter (FSC or size) and proliferation dependent CFSE dilution was measured by flow cytometry with a Guava EasyCyte 12 Flow Cytometer (EMD Millipore). Data analysis was performed on a minimum of ten thousand recorded events per sample with FlowJo 10.1 software (FlowJo, LLC). The percentage of responding cells was determined by gating on Forward Scatter and CFSE using the media control to determine proper gate location. Cells that had either increased cell size or decreased CFSE levels were labeled as responding cells. The individual data from two biological replicates from one donor is shown in below copied table (Quantification of T cell activation) These results are consistent with results from additional donors and clearly showed that treatment of human T cells in vitro with Protein A enhances T cell activation and proliferation as compared to antibody stimulation alone.

Quantification of T cell activation.

Human T Cell Activation Following Treatment with Protein A In Vitro

| Stimulation | % of cells responding | |
|---|---|---|
| | Sample 1 | Sample 2 |
| Media | 3 | 3 |
| anti-CD3 | 56 | 62 |
| anti-CD3/28 | 87 | 85 |
| anti-CD3 + APG1472 10 ng/ml | 71 | 69 |
| anti-CD3 + APG1472 100 ng/ml | 75 | 71 |
| anti-CD3 + APG1472 1000 ng/ml | 66 | 75 |

Example 10: Receptor Binding Assay

Figure 6:
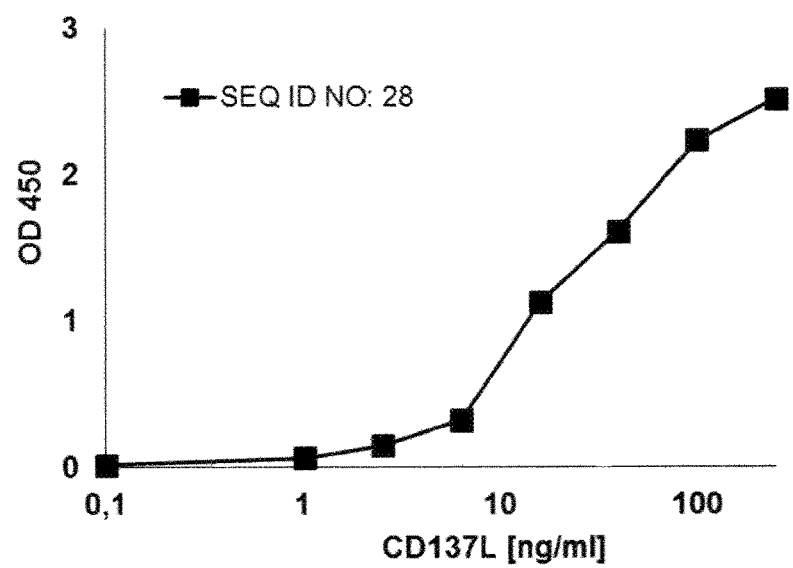
FIG. 6 ELISA assessing the binding of CD137 receptor agonist protein (Protein A) to its receptor FIG. 7 Analytical size exclusion chromatography of strep tagged Protein A (SEQ ID NO: 28) performed on a 1260 Infinity HPLC system using a Tosoh TSKgelG3000SWxl column. The column was loaded with protein at a concentration of 1 mg/ml in a total volume of 20 μl. The flow rate was set to 0.5 ml/min. One observes a single main peak at 16.97 min for Protein A. The low molecular weight buffer components of the sample elute after one column volume (>23.5 min).
Figure 7:
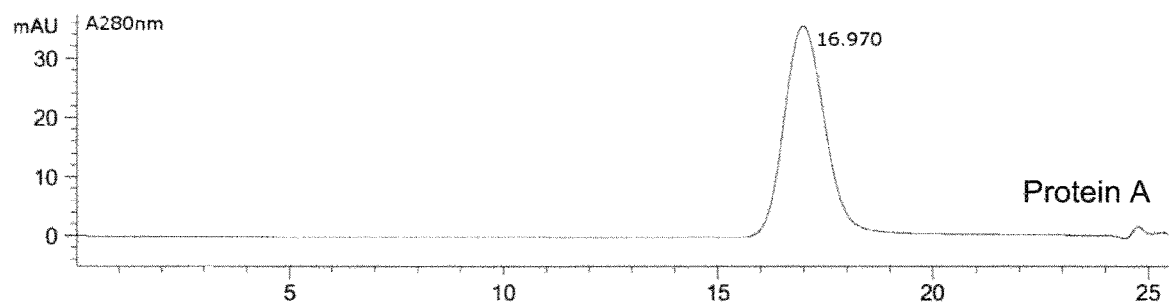
Figure 8:
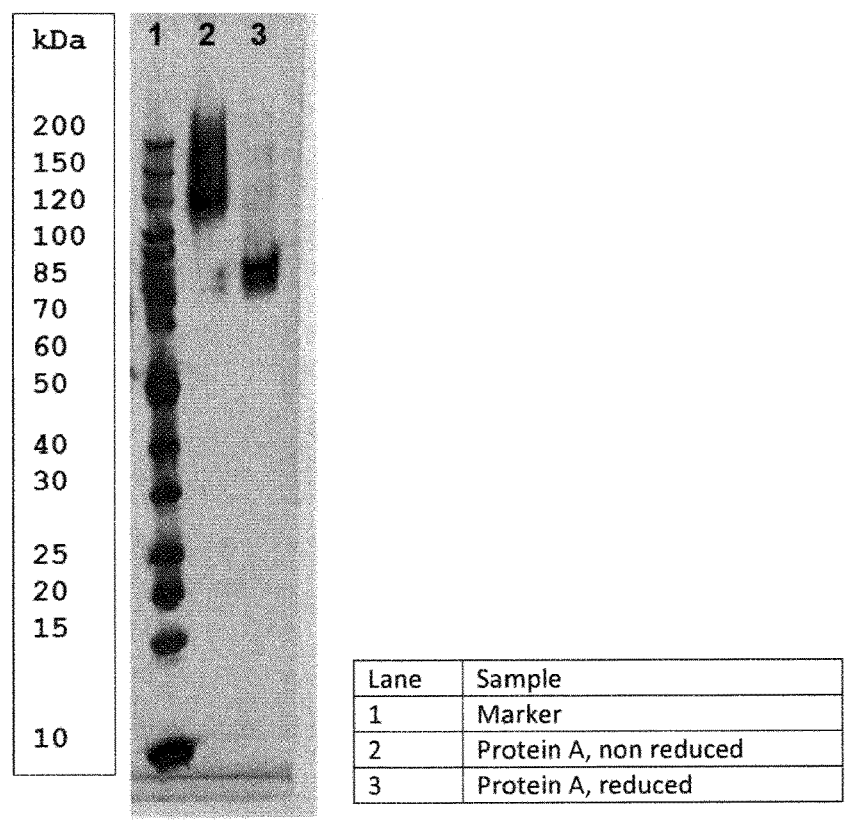
FIG. 8 SDS-PAGE results of Protein A under non-reducing and reducing conditions. 360 ng of Protein A were loaded on an SDS-PAGE 4-12% Bis-Tris gel under non-reducing (Lane 1) or reducing (Lane 2) conditions containing DTT as reducing agent. Gels were run at 130V for 15 min followed by 180V for 60 min and were subsequently stained using a silver-stain protocol. One observes a molecular weight difference between the main bands in A and B of about 70-80 kDa. As this is about half the molecular weight as observed for the main band in lane 1, this indicates that the homodimer in lane 2 is covalently linked by disulfide bridges. The bonds are lost under reducing conditions in lane 2

For ELISA assays assessing functional binding of CD137 receptor agonist protein of the invention to its corresponding receptor, coating of microtiter plates was performed with 1 µg/ml CD137-Fc (Bio-Techne GmbH, Wiesbaden-Nordenstadt, Germany). After blocking with StartingBlock (Life Technologies GmbH, Darmstadt, Germany), wells were incubated with indicated concentrations of strep-tagged Protein A (SEQ ID NO: 28). Binding to its corresponding receptor was detected via its Strep Tag II employing the anti-StrepTag-peroxidase StrepTactin-HRP (1:5000, IBA GmbH, Goettingen, Germany) and subsequent detection of the converted Peroxidase-substrate TMB one (Kem-En-Tec Diagnostics, Taastrup, Denmark) at a wavelength of 450 nm in an ELISA reader. FIG. 6 clearly depicts concentration dependent binding of Protein A to its receptor.

What is claimed is:

1. A CD137 receptor agonist protein comprising a single-chain fusion polypeptide comprising:
   (i) a first soluble CD137L domain,
   (ii) a first peptide linker having 3 to 8 amino acids,
   (iii) a second soluble CD137L domain,
   (iv) a second peptide linker having 3 to 8 amino acids, and
   (v) a third soluble CD137L domain, and
   (vi) a hinge-linker selected from the group comprising SEQ ID NOs: 16 and 19-24, and
   (vii) an antibody Fc fragment, wherein the antibody Fc fragment (vii) consists of the amino acid sequence as shown in SEQ ID NO: 13 or amino acids 1-217 of SEQ ID NO: 13, and the soluble CD137L domains (i), (iii), and (v) independently comprise amino acids 90-240, of SEQ ID NO: 1.

2. The CD137 receptor agonist protein of claim 1, wherein the antibody Fc fragment (vii) is fused to the C-terminal end of the third CD137L domain (v) via a hinge-linker (vi).

3. The CD137 receptor agonist protein of claim 1, wherein the soluble CD137L domains (i), (iii) and (v) consist of amino acids 89-240 of SEQ ID NO: 1.

4. The CD137 receptor agonist protein of claim 1, wherein the first and second peptide linkers (ii) and (iv) independently have one of the amino acid sequence of SEQ ID NOs: 2-12.

5. The CD137 receptor agonist protein of claim 4, wherein the first and the second peptide linkers (ii) and (iv) consist of the amino acid sequence according to SEQ ID NO: 2.

6. The CD137 receptor agonist protein of claim 1 which additionally comprises an N-terminal signal peptide domain, or a C-terminal element comprising a recognition or purification domain.

7. The CD137 receptor agonist protein of claim 1, comprising the amino acid sequence of any one of SEQ ID NOs: 15 and 25-35.

8. A dimer comprising two polypeptides each having the amino acid sequence as set forth in SEQ ID NOs: 27, 29, 30, 32, 33, 34 or 35, fused via three disulfide bridges.

9. The dimer of claim 8, wherein the two polypeptides are covalently linked through three interchain disulfide bonds formed at:
   a) positions 484, 490 and 493 of SEQ ID NO: 27, 29, 30, 32, or 35 or
   b) positions 489, 490 and 493 of SEQ ID NO: 30, or
   c) positions 493, 489 and 502 of SEQ ID NO: 31, or
   d) positions 487, 493 and 496 of SEQ ID NO: 33 or 34.

10. The dimer of claim 8, comprising one or more N-glycosylated asparagine residues selected from the group consisting of N158 and N318 of SEQ ID NOs: 27 and 29; N161 and N324 of SEQ ID NO: 30 and 31; N159 and N320 of SEQ ID NO: 33 and 34; and N86, N158, N246, N318 and N406 of SEQ ID NO 35.

11. A pharmaceutical composition comprising the CD137 receptor agonist protein of claim 1 and one or more pharmaceutically acceptable carriers, diluents, excipients, or adjuvants.

12. The CD137 receptor agonist protein of claim 1, wherein each of the soluble CD137L domains (i), (iii), and (v) independently consists of amino acids 89-240, 89-241, 89-243, 90-240, 90-241, or 90-243 of SEQ ID NO: 1.

13. The CD137 receptor agonist protein of claim 1, wherein the antibody fragment (vii) consists of the amino acid sequence of SEQ ID NO: 13 or the amino acids 1-217 of SEQ ID NO: 13.

14. A CD137 receptor agonist protein comprising a single-chain fusion polypeptide comprising:
- (i) a first soluble CD137L domain,
- (ii) a first peptide linker having 3 to 8 amino acids,
- (iii) a second soluble CD137L domain,
- (iv) a second peptide linker having 3 to 8 amino acids, and
- (v) a third soluble CD137L domain, and
- (vi) a hinge-linker selected from the group comprising SEQ ID NOs: 16 and 19-24, and
- (vii) an antibody Fc fragment consisting of the amino acid sequence of SEQ ID NO: 13 or amino acids 1-217 of SEQ ID NO: 13,
- wherein the soluble CD137L domain (i) comprises amino acids 89-240 of SEQ ID NO: 1, with the Glu89 being post-translationally modified to pyroglutamate, and the soluble CD137L domains (iii) and (v) independently comprise amino acids 90-240 of SEQ ID NO: 1.

15. The CD137 receptor agonist protein of claim 14, wherein the soluble CD137L domain (i) consists of amino acids 89-240, 89-241, or 89-243 of SEQ ID NO: 1, with the Glu89 being post-translationally modified to pyroglutamate, and each of the soluble CD137L domains (iii) and (v) independently consists of amino acid acids 89-240, 89-241, 89-243, 90-240, 90-241, or 90-243 of SEQ ID NO: 1.

* * * * *

SEQUENCE LISTING

```
<160> NUMBER OF SEQ ID NOS: 43

<210> SEQ ID NO 1
<211> LENGTH: 254
<212> TYPE: PRT
<213> ORGANISM: Homo sapiens
<220> FEATURE:
<223> OTHER INFORMATION: CD137 ligand WT

<400> SEQUENCE: 1

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
    210                 215                 220
```

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 2
<211> LENGTH: 8
<212> TYPE: PRT
<213> ORGANISM: Artificial Sequence
<220> FEATURE:
<223> OTHER INFORMATION: linker

<400> SEQUENCE: 2

Gly Ser Gly Ser Gly Asn Gly Ser
1               5

<210> SEQ ID NO 3
<211> LENGTH: 8
<212> TYPE: PRT
<213> ORGANISM: Artificial Sequence
<220> FEATURE:
<223> OTHER INFORMATION: linker

<400> SEQUENCE: 3

Gly Ser Gly Ser Gly Ser Gly Ser
1               5

<210> SEQ ID NO 4
<211> LENGTH: 8
<212> TYPE: PRT
<213> ORGANISM: Artificial Sequence
<220> FEATURE:
<223> OTHER INFORMATION: linker

<400> SEQUENCE: 4

Gly Gly Ser Gly Ser Gly Ser Gly
1               5

<210> SEQ ID NO 5
<211> LENGTH: 6
<212> TYPE: PRT
<213> ORGANISM: Artificial Sequence
<220> FEATURE:
<223> OTHER INFORMATION: linker

<400> SEQUENCE: 5

Gly Gly Ser Gly Ser Gly
1               5

<210> SEQ ID NO 6
<211> LENGTH: 4
<212> TYPE: PRT
<213> ORGANISM: Artificial Sequence
<220> FEATURE:
<223> OTHER INFORMATION: linker

<400> SEQUENCE: 6

Gly Gly Ser Gly
1

<210> SEQ ID NO 7
<211> LENGTH: 8
<212> TYPE: PRT
<213> ORGANISM: Artificial Sequence
<220> FEATURE:
<223> OTHER INFORMATION: linker

```
<400> SEQUENCE: 7

Gly Gly Ser Gly Asn Gly Ser Gly
1               5

<210> SEQ ID NO 8
<211> LENGTH: 8
<212> TYPE: PRT
<213> ORGANISM: Artificial Sequence
<220> FEATURE:
<223> OTHER INFORMATION: linker

<400> SEQUENCE: 8

Gly Gly Asn Gly Ser Gly Ser Gly
1               5

<210> SEQ ID NO 9
<211> LENGTH: 6
<212> TYPE: PRT
<213> ORGANISM: Artificial Sequence
<220> FEATURE:
<223> OTHER INFORMATION: linker

<400> SEQUENCE: 9

Gly Gly Asn Gly Ser Gly
1               5

<210> SEQ ID NO 10
<211> LENGTH: 6
<212> TYPE: PRT
<213> ORGANISM: Artificial Sequence
<220> FEATURE:
<223> OTHER INFORMATION: linker

<400> SEQUENCE: 10

Gly Ser Gly Ser Gly Ser
1               5

<210> SEQ ID NO 11
<211> LENGTH: 4
<212> TYPE: PRT
<213> ORGANISM: Artificial Sequence
<220> FEATURE:
<223> OTHER INFORMATION: linker

<400> SEQUENCE: 11

Gly Ser Gly Ser
1

<210> SEQ ID NO 12
<211> LENGTH: 3
<212> TYPE: PRT
<213> ORGANISM: Artificial Sequence
<220> FEATURE:
<223> OTHER INFORMATION: linker

<400> SEQUENCE: 12

Gly Ser Gly
1

<210> SEQ ID NO 13
<211> LENGTH: 218
<212> TYPE: PRT
<213> ORGANISM: Artificial Sequence
<220> FEATURE:
<223> OTHER INFORMATION: IGG1-Fc N297S

<400> SEQUENCE: 13
```

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Asp Val Ser His Glu Asp Pro Glu Val Lys Phe Asn Trp
            35                  40                  45

Tyr Val Asp Gly Val Glu Val His Asn Ala Lys Thr Lys Pro Arg Glu
        50                  55                  60

Glu Gln Tyr Ser Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
                100                 105                 110

Gln Pro Arg Glu Pro Gln Val Tyr Thr Leu Pro Pro Ser Arg Glu Glu
            115                 120                 125

Met Thr Lys Asn Gln Val Ser Leu Thr Cys Leu Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
                180                 185                 190

Val Phe Ser Cys Ser Val Met His Glu Ala Leu His Asn His Tyr Thr
            195                 200                 205

Gln Lys Ser Leu Ser Leu Ser Pro Gly Lys
210                 215

<210> SEQ ID NO 14
<211> LENGTH: 217
<212> TYPE: PRT
<213> ORGANISM: Artificial Sequence
<220> FEATURE:
<223> OTHER INFORMATION: IGG1-Fc WT

<400> SEQUENCE: 14

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
                100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
        210                 215

<210> SEQ ID NO 15
<211> LENGTH: 745
<212> TYPE: PRT
<213> ORGANISM: Artificial Sequence
<220> FEATURE:
<223> OTHER INFORMATION: PROT A (CD137L Deglyco Fc)

<400> SEQUENCE: 15

Met Glu Thr Asp Thr Leu Leu Val Phe Val Leu Leu Val Trp Val Pro
1               5                   10                  15

Ala Gly Asn Gly Gln Gly Met Phe Ala Gln Leu Val Ala Gln Asn Val
                20                  25                  30

Leu Leu Ile Asp Gly Pro Leu Ser Trp Tyr Ser Asp Pro Gly Leu Ala
            35                  40                  45

Gly Val Ser Leu Thr Gly Gly Leu Ser Tyr Lys Glu Asp Thr Lys Glu
        50                  55                  60

Leu Val Val Ala Lys Ala Gly Val Tyr Tyr Val Phe Phe Gln Leu Glu
65                  70                  75                  80

Leu Arg Arg Val Val Ala Gly Glu Gly Ser Gly Ser Val Ser Leu Ala
                85                  90                  95

Leu His Leu Gln Pro Leu Arg Ser Ala Ala Gly Ala Ala Ala Leu Ala
            100                 105                 110

Leu Thr Val Asp Leu Pro Pro Ala Ser Ser Glu Ala Arg Asn Ser Ala
        115                 120                 125

Phe Gly Phe Gln Gly Arg Leu Leu His Leu Ser Ala Gly Gln Arg Leu
130                 135                 140

Gly Val His Leu His Thr Glu Ala Arg Ala Arg His Ala Trp Gln Leu
145                 150                 155                 160

Thr Gln Gly Ala Thr Val Leu Gly Leu Phe Arg Val Gly Ser Gly Ser
                165                 170                 175

Gly Asn Gly Ser Gln Gly Met Phe Ala Gln Leu Val Ala Gln Asn Val
            180                 185                 190

Leu Leu Ile Asp Gly Pro Leu Ser Trp Tyr Ser Asp Pro Gly Leu Ala
        195                 200                 205

Gly Val Ser Leu Thr Gly Gly Leu Ser Tyr Lys Glu Asp Thr Lys Glu
    210                 215                 220

Leu Val Val Ala Lys Ala Gly Val Tyr Tyr Val Phe Phe Gln Leu Glu
225                 230                 235                 240

Leu Arg Arg Val Val Ala Gly Glu Gly Ser Gly Ser Val Ser Leu Ala
                245                 250                 255

Leu His Leu Gln Pro Leu Arg Ser Ala Ala Gly Ala Ala Ala Leu Ala
            260                 265                 270

Leu Thr Val Asp Leu Pro Pro Ala Ser Ser Glu Ala Arg Asn Ser Ala
        275                 280                 285

```
Phe Gly Phe Gln Gly Arg Leu Leu His Leu Ser Ala Gly Gln Arg Leu
    290                 295                 300

Gly Val His Leu His Thr Glu Ala Arg Ala Arg His Ala Trp Gln Leu
305                 310                 315                 320

Thr Gln Gly Ala Thr Val Leu Gly Leu Phe Arg Val Gly Ser Gly Ser
                325                 330                 335

Gly Asn Gly Ser Gln Gly Met Phe Ala Gln Leu Val Ala Gln Asn Val
                340                 345                 350

Leu Leu Ile Asp Gly Pro Leu Ser Trp Tyr Ser Asp Pro Gly Leu Ala
        355                 360                 365

Gly Val Ser Leu Thr Gly Gly Leu Ser Tyr Lys Glu Asp Thr Lys Glu
370                 375                 380

Leu Val Val Ala Lys Ala Gly Val Tyr Tyr Val Phe Phe Gln Leu Glu
385                 390                 395                 400

Leu Arg Arg Val Val Ala Gly Glu Gly Ser Gly Ser Val Ser Leu Ala
                405                 410                 415

Leu His Leu Gln Pro Leu Arg Ser Ala Ala Gly Ala Ala Ala Leu Ala
                420                 425                 430

Leu Thr Val Asp Leu Pro Pro Ala Ser Ser Glu Ala Arg Asn Ser Ala
        435                 440                 445

Phe Gly Phe Gln Gly Arg Leu Leu His Leu Ser Ala Gly Gln Arg Leu
    450                 455                 460

Gly Val His Leu His Thr Glu Ala Arg Ala Arg His Ala Trp Gln Leu
465                 470                 475                 480

Thr Gln Gly Ala Thr Val Leu Gly Leu Phe Arg Val Gly Ser Ser Ser
                485                 490                 495

Ser Ser Ser Ser Ser Gly Ser Cys Asp Lys Thr His Thr Cys Pro Pro
                500                 505                 510

Cys Pro Ala Pro Glu Leu Leu Gly Gly Pro Ser Val Phe Leu Phe Pro
        515                 520                 525

Pro Lys Pro Lys Asp Thr Leu Met Ile Ser Arg Thr Pro Glu Val Thr
        530                 535                 540

Cys Val Val Val Asp Val Ser His Glu Asp Pro Glu Val Lys Phe Asn
545                 550                 555                 560

Trp Tyr Val Asp Gly Val Glu Val His Asn Ala Lys Thr Lys Pro Arg
                565                 570                 575

Glu Glu Gln Tyr Ser Ser Thr Tyr Arg Val Val Ser Val Leu Thr Val
                580                 585                 590

Leu His Gln Asp Trp Leu Asn Gly Lys Glu Tyr Lys Cys Lys Val Ser
        595                 600                 605

Asn Lys Ala Leu Pro Ala Pro Ile Glu Lys Thr Ile Ser Lys Ala Lys
    610                 615                 620

Gly Gln Pro Arg Glu Pro Gln Val Tyr Thr Leu Pro Pro Ser Arg Glu
625                 630                 635                 640

Glu Met Thr Lys Asn Gln Val Ser Leu Thr Cys Leu Val Lys Gly Phe
                645                 650                 655

Tyr Pro Ser Asp Ile Ala Val Glu Trp Glu Ser Asn Gly Gln Pro Glu
                660                 665                 670

Asn Asn Tyr Lys Thr Thr Pro Pro Val Leu Asp Ser Asp Gly Ser Phe
            675                 680                 685

Phe Leu Tyr Ser Lys Leu Thr Val Asp Lys Ser Arg Trp Gln Gln Gly
    690                 695                 700
```

```
Asn Val Phe Ser Cys Ser Val Met His Glu Ala Leu His Asn His Tyr
705                 710                 715                 720

Thr Gln Lys Ser Leu Ser Leu Ser Pro Gly Ser Ser Ser Ser Ser
            725                 730                 735

Ala Trp Ser His Pro Gln Phe Glu Lys
            740                 745

<210> SEQ ID NO 16
<211> LENGTH: 21
<212> TYPE: PRT
<213> ORGANISM: Artificial Sequence
<220> FEATURE:
<223> OTHER INFORMATION: hinge linker

<400> SEQUENCE: 16

Gly Ser Ser Ser Ser Ser Ser Ser Gly Ser Cys Asp Lys Thr His
1               5                   10                  15

Thr Cys Pro Pro Cys
            20

<210> SEQ ID NO 17
<211> LENGTH: 20
<212> TYPE: PRT
<213> ORGANISM: Artificial Sequence
<220> FEATURE:
<223> OTHER INFORMATION: universal signal peptide

<400> SEQUENCE: 17

Met Glu Thr Asp Thr Leu Leu Val Phe Val Leu Leu Val Trp Val Pro
1               5                   10                  15

Ala Gly Asn Gly
            20

<210> SEQ ID NO 18
<211> LENGTH: 15
<212> TYPE: PRT
<213> ORGANISM: Artificial Sequence
<220> FEATURE:
<223> OTHER INFORMATION: serine linker with strep tag

<400> SEQUENCE: 18

Ser Ser Ser Ser Ser Ser Ala Trp Ser His Pro Gln Phe Glu Lys
1               5                   10                  15

<210> SEQ ID NO 19
<211> LENGTH: 20
<212> TYPE: PRT
<213> ORGANISM: Artificial Sequence
<220> FEATURE:
<223> OTHER INFORMATION: hinge linker

<400> SEQUENCE: 19

Gly Ser Ser Ser Ser Ser Ser Gly Ser Cys Asp Lys Thr His Thr
1               5                   10                  15

Cys Pro Pro Cys
            20

<210> SEQ ID NO 20
<211> LENGTH: 19
<212> TYPE: PRT
<213> ORGANISM: Artificial Sequence
<220> FEATURE:
<223> OTHER INFORMATION: hinge linker

<400> SEQUENCE: 20
```

```
Gly Ser Ser Ser Ser Ser Gly Ser Cys Asp Lys Thr His Thr Cys
1               5                   10                  15

Pro Pro Cys

<210> SEQ ID NO 21
<211> LENGTH: 18
<212> TYPE: PRT
<213> ORGANISM: Artificial Sequence
<220> FEATURE:
<223> OTHER INFORMATION: hinge linker

<400> SEQUENCE: 21

Gly Ser Ser Ser Ser Ser Gly Ser Cys Asp Lys Thr His Thr Cys Pro
1               5                   10                  15

Pro Cys

<210> SEQ ID NO 22
<211> LENGTH: 16
<212> TYPE: PRT
<213> ORGANISM: Artificial Sequence
<220> FEATURE:
<223> OTHER INFORMATION: hinge linker

<400> SEQUENCE: 22

Gly Ser Ser Ser Gly Ser Cys Asp Lys Thr His Thr Cys Pro Pro Cys
1               5                   10                  15

<210> SEQ ID NO 23
<211> LENGTH: 18
<212> TYPE: PRT
<213> ORGANISM: Artificial Sequence
<220> FEATURE:
<223> OTHER INFORMATION: hinge linker

<400> SEQUENCE: 23

Gly Ser Ser Ser Gly Ser Cys Asp Lys Thr His Thr Cys Pro Pro Cys
1               5                   10                  15

Gly Ser

<210> SEQ ID NO 24
<211> LENGTH: 20
<212> TYPE: PRT
<213> ORGANISM: Artificial Sequence
<220> FEATURE:
<223> OTHER INFORMATION: hinge linker

<400> SEQUENCE: 24

Gly Ser Ser Ser Gly Ser Cys Asp Lys Thr His Thr Cys Pro Pro Cys
1               5                   10                  15

Gly Ser Gly Ser
            20

<210> SEQ ID NO 25
<211> LENGTH: 731
<212> TYPE: PRT
<213> ORGANISM: Artificial Sequence
<220> FEATURE:
<223> OTHER INFORMATION: PROTEIN A - no strep tag

<400> SEQUENCE: 25

Met Glu Thr Asp Thr Leu Leu Val Phe Val Leu Val Trp Val Pro
1               5                   10                  15

Ala Gly Asn Gly Gln Gly Met Phe Ala Gln Leu Val Ala Gln Asn Val
```

-continued

```
                20                  25                  30
Leu Leu Ile Asp Gly Pro Leu Ser Trp Tyr Ser Asp Pro Gly Leu Ala
             35                  40                  45
Gly Val Ser Leu Thr Gly Gly Leu Ser Tyr Lys Glu Asp Thr Lys Glu
 50                  55                  60
Leu Val Val Ala Lys Ala Gly Val Tyr Tyr Val Phe Phe Gln Leu Glu
 65                  70                  75                  80
Leu Arg Arg Val Val Ala Gly Glu Gly Ser Gly Ser Val Ser Leu Ala
                     85                  90                  95
Leu His Leu Gln Pro Leu Arg Ser Ala Ala Gly Ala Ala Ala Leu Ala
                100                 105                 110
Leu Thr Val Asp Leu Pro Pro Ala Ser Ser Glu Ala Arg Asn Ser Ala
                115                 120                 125
Phe Gly Phe Gln Gly Arg Leu Leu His Leu Ser Ala Gly Gln Arg Leu
                130                 135                 140
Gly Val His Leu His Thr Glu Ala Arg Ala Arg His Ala Trp Gln Leu
145                 150                 155                 160
Thr Gln Gly Ala Thr Val Leu Gly Leu Phe Arg Val Gly Ser Gly Ser
                     165                 170                 175
Gly Asn Gly Ser Gln Gly Met Phe Ala Gln Leu Val Ala Gln Asn Val
                180                 185                 190
Leu Leu Ile Asp Gly Pro Leu Ser Trp Tyr Ser Asp Pro Gly Leu Ala
                195                 200                 205
Gly Val Ser Leu Thr Gly Gly Leu Ser Tyr Lys Glu Asp Thr Lys Glu
                210                 215                 220
Leu Val Val Ala Lys Ala Gly Val Tyr Tyr Val Phe Phe Gln Leu Glu
225                 230                 235                 240
Leu Arg Arg Val Val Ala Gly Glu Gly Ser Gly Ser Val Ser Leu Ala
                     245                 250                 255
Leu His Leu Gln Pro Leu Arg Ser Ala Ala Gly Ala Ala Ala Leu Ala
                260                 265                 270
Leu Thr Val Asp Leu Pro Pro Ala Ser Ser Glu Ala Arg Asn Ser Ala
                275                 280                 285
Phe Gly Phe Gln Gly Arg Leu Leu His Leu Ser Ala Gly Gln Arg Leu
                290                 295                 300
Gly Val His Leu His Thr Glu Ala Arg Ala Arg His Ala Trp Gln Leu
305                 310                 315                 320
Thr Gln Gly Ala Thr Val Leu Gly Leu Phe Arg Val Gly Ser Gly Ser
                     325                 330                 335
Gly Asn Gly Ser Gln Gly Met Phe Ala Gln Leu Val Ala Gln Asn Val
                340                 345                 350
Leu Leu Ile Asp Gly Pro Leu Ser Trp Tyr Ser Asp Pro Gly Leu Ala
                355                 360                 365
Gly Val Ser Leu Thr Gly Gly Leu Ser Tyr Lys Glu Asp Thr Lys Glu
                370                 375                 380
Leu Val Val Ala Lys Ala Gly Val Tyr Tyr Val Phe Phe Gln Leu Glu
385                 390                 395                 400
Leu Arg Arg Val Val Ala Gly Glu Gly Ser Gly Ser Val Ser Leu Ala
                     405                 410                 415
Leu His Leu Gln Pro Leu Arg Ser Ala Ala Gly Ala Ala Ala Leu Ala
                420                 425                 430
Leu Thr Val Asp Leu Pro Pro Ala Ser Ser Glu Ala Arg Asn Ser Ala
                435                 440                 445
```

```
Phe Gly Phe Gln Gly Arg Leu Leu His Leu Ser Ala Gly Gln Arg Leu
    450                 455                 460

Gly Val His Leu His Thr Glu Ala Arg Ala Arg His Ala Trp Gln Leu
465                 470                 475                 480

Thr Gln Gly Ala Thr Val Leu Gly Leu Phe Arg Val Gly Ser Ser Ser
                485                 490                 495

Ser Ser Ser Ser Ser Gly Ser Cys Asp Lys Thr His Thr Cys Pro Pro
            500                 505                 510

Cys Pro Ala Pro Glu Leu Leu Gly Gly Pro Ser Val Phe Leu Phe Pro
        515                 520                 525

Pro Lys Pro Lys Asp Thr Leu Met Ile Ser Arg Thr Pro Glu Val Thr
    530                 535                 540

Cys Val Val Val Asp Val Ser His Glu Asp Pro Glu Val Lys Phe Asn
545                 550                 555                 560

Trp Tyr Val Asp Gly Val Glu Val His Asn Ala Lys Thr Lys Pro Arg
                565                 570                 575

Glu Glu Gln Tyr Ser Ser Thr Tyr Arg Val Val Ser Val Leu Thr Val
            580                 585                 590

Leu His Gln Asp Trp Leu Asn Gly Lys Glu Tyr Lys Cys Lys Val Ser
        595                 600                 605

Asn Lys Ala Leu Pro Ala Pro Ile Glu Lys Thr Ile Ser Lys Ala Lys
    610                 615                 620

Gly Gln Pro Arg Glu Pro Gln Val Tyr Thr Leu Pro Pro Ser Arg Glu
625                 630                 635                 640

Glu Met Thr Lys Asn Gln Val Ser Leu Thr Cys Leu Val Lys Gly Phe
                645                 650                 655

Tyr Pro Ser Asp Ile Ala Val Glu Trp Glu Ser Asn Gly Gln Pro Glu
            660                 665                 670

Asn Asn Tyr Lys Thr Thr Pro Pro Val Leu Asp Ser Asp Gly Ser Phe
        675                 680                 685

Phe Leu Tyr Ser Lys Leu Thr Val Asp Lys Ser Arg Trp Gln Gln Gly
    690                 695                 700

Asn Val Phe Ser Cys Ser Val Met His Glu Ala Leu His Asn His Tyr
705                 710                 715                 720

Thr Gln Lys Ser Leu Ser Leu Ser Pro Gly Lys
                725                 730

<210> SEQ ID NO 26
<211> LENGTH: 730
<212> TYPE: PRT
<213> ORGANISM: Artificial Sequence
<220> FEATURE:
<223> OTHER INFORMATION: CD137L-wt fused to Seq_14

<400> SEQUENCE: 26

Met Glu Thr Asp Thr Leu Leu Val Phe Val Leu Leu Val Trp Val Pro
1               5                   10                  15

Ala Gly Asn Gly Gln Gly Met Phe Ala Gln Leu Val Ala Gln Asn Val
            20                  25                  30

Leu Leu Ile Asp Gly Pro Leu Ser Trp Tyr Ser Asp Pro Gly Leu Ala
        35                  40                  45

Gly Val Ser Leu Thr Gly Gly Leu Ser Tyr Lys Glu Asp Thr Lys Glu
    50                  55                  60

Leu Val Val Ala Lys Ala Gly Val Tyr Tyr Val Phe Phe Gln Leu Glu
65                  70                  75                  80
```

```
Leu Arg Arg Val Val Ala Gly Glu Gly Ser Gly Ser Val Ser Leu Ala
                85                  90                  95

Leu His Leu Gln Pro Leu Arg Ser Ala Ala Gly Ala Ala Ala Leu Ala
                100                 105                 110

Leu Thr Val Asp Leu Pro Pro Ala Ser Ser Glu Ala Arg Asn Ser Ala
                115                 120                 125

Phe Gly Phe Gln Gly Arg Leu Leu His Leu Ser Ala Gly Gln Arg Leu
130                 135                 140

Gly Val His Leu His Thr Glu Ala Arg Ala Arg His Ala Trp Gln Leu
145                 150                 155                 160

Thr Gln Gly Ala Thr Val Leu Gly Leu Phe Arg Val Gly Ser Gly Ser
                165                 170                 175

Gly Asn Gly Ser Gln Gly Met Phe Ala Gln Leu Val Ala Gln Asn Val
                180                 185                 190

Leu Leu Ile Asp Gly Pro Leu Ser Trp Tyr Ser Asp Pro Gly Leu Ala
                195                 200                 205

Gly Val Ser Leu Thr Gly Gly Leu Ser Tyr Lys Glu Asp Thr Lys Glu
                210                 215                 220

Leu Val Val Ala Lys Ala Gly Val Tyr Tyr Val Phe Phe Gln Leu Glu
225                 230                 235                 240

Leu Arg Arg Val Val Ala Gly Glu Gly Ser Gly Ser Val Ser Leu Ala
                245                 250                 255

Leu His Leu Gln Pro Leu Arg Ser Ala Ala Gly Ala Ala Ala Leu Ala
                260                 265                 270

Leu Thr Val Asp Leu Pro Pro Ala Ser Ser Glu Ala Arg Asn Ser Ala
                275                 280                 285

Phe Gly Phe Gln Gly Arg Leu Leu His Leu Ser Ala Gly Gln Arg Leu
                290                 295                 300

Gly Val His Leu His Thr Glu Ala Arg Ala Arg His Ala Trp Gln Leu
305                 310                 315                 320

Thr Gln Gly Ala Thr Val Leu Gly Leu Phe Arg Val Gly Ser Gly Ser
                325                 330                 335

Gly Asn Gly Ser Gln Gly Met Phe Ala Gln Leu Val Ala Gln Asn Val
                340                 345                 350

Leu Leu Ile Asp Gly Pro Leu Ser Trp Tyr Ser Asp Pro Gly Leu Ala
                355                 360                 365

Gly Val Ser Leu Thr Gly Gly Leu Ser Tyr Lys Glu Asp Thr Lys Glu
                370                 375                 380

Leu Val Val Ala Lys Ala Gly Val Tyr Tyr Val Phe Phe Gln Leu Glu
385                 390                 395                 400

Leu Arg Arg Val Val Ala Gly Glu Gly Ser Gly Ser Val Ser Leu Ala
                405                 410                 415

Leu His Leu Gln Pro Leu Arg Ser Ala Ala Gly Ala Ala Ala Leu Ala
                420                 425                 430

Leu Thr Val Asp Leu Pro Pro Ala Ser Ser Glu Ala Arg Asn Ser Ala
                435                 440                 445

Phe Gly Phe Gln Gly Arg Leu Leu His Leu Ser Ala Gly Gln Arg Leu
                450                 455                 460

Gly Val His Leu His Thr Glu Ala Arg Ala Arg His Ala Trp Gln Leu
465                 470                 475                 480

Thr Gln Gly Ala Thr Val Leu Gly Leu Phe Arg Val Gly Ser Ser Ser
                485                 490                 495
```

-continued

Ser Ser Ser Ser Ser Gly Ser Cys Asp Lys Thr His Thr Cys Pro Pro
                500                 505                 510

Cys Pro Ala Pro Pro Val Ala Gly Pro Ser Val Phe Leu Phe Pro Pro
        515                 520                 525

Lys Pro Lys Asp Thr Leu Met Ile Ser Arg Thr Pro Glu Val Thr Cys
530                 535                 540

Val Val Val Asp Val Ser His Glu Asp Pro Glu Val Lys Phe Asn Trp
545                 550                 555                 560

Tyr Val Asp Gly Val Glu Val His Asn Ala Lys Thr Lys Pro Arg Glu
                565                 570                 575

Glu Gln Tyr Asn Ser Thr Tyr Arg Val Val Ser Val Leu Thr Val Leu
            580                 585                 590

His Gln Asp Trp Leu Asn Gly Lys Glu Tyr Lys Cys Lys Val Ser Asn
        595                 600                 605

Lys Gly Leu Pro Ser Ser Ile Glu Lys Thr Ile Ser Lys Ala Lys Gly
    610                 615                 620

Gln Pro Arg Glu Pro Gln Val Tyr Thr Leu Pro Pro Ser Arg Glu Glu
625                 630                 635                 640

Met Thr Lys Asn Gln Val Ser Leu Thr Cys Leu Val Lys Gly Phe Tyr
                645                 650                 655

Pro Ser Asp Ile Ala Val Glu Trp Glu Ser Asn Gly Gln Pro Glu Asn
            660                 665                 670

Asn Tyr Lys Thr Thr Pro Pro Val Leu Asp Ser Asp Gly Ser Phe Phe
        675                 680                 685

Leu Tyr Ser Lys Leu Thr Val Asp Lys Ser Arg Trp Gln Gln Gly Asn
    690                 695                 700

Val Phe Ser Cys Ser Val Met His Glu Ala Leu His Asn His Tyr Thr
705                 710                 715                 720

Gln Lys Ser Leu Ser Leu Ser Pro Gly Lys
                725                 730

<210> SEQ ID NO 27
<211> LENGTH: 711
<212> TYPE: PRT
<213> ORGANISM: Artificial Sequence
<220> FEATURE:
<223> OTHER INFORMATION: CD137L-wt fused to Seq_13 (no sig, no strep
      tag, no glyco)

<400> SEQUENCE: 27

Gln Gly Met Phe Ala Gln Leu Val Ala Gln Asn Val Leu Leu Ile Asp
1               5                   10                  15

Gly Pro Leu Ser Trp Tyr Ser Asp Pro Gly Leu Ala Gly Val Ser Leu
                20                  25                  30

Thr Gly Gly Leu Ser Tyr Lys Glu Asp Thr Lys Glu Leu Val Val Ala
            35                  40                  45

Lys Ala Gly Val Tyr Tyr Val Phe Phe Gln Leu Glu Leu Arg Arg Val
        50                  55                  60

Val Ala Gly Glu Gly Ser Gly Ser Val Ser Leu Ala Leu His Leu Gln
65                  70                  75                  80

Pro Leu Arg Ser Ala Ala Gly Ala Ala Ala Leu Ala Leu Thr Val Asp
                85                  90                  95

Leu Pro Pro Ala Ser Ser Glu Ala Arg Asn Ser Ala Phe Gly Phe Gln
                100                 105                 110

Gly Arg Leu Leu His Leu Ser Ala Gly Gln Arg Leu Gly Val His Leu
            115                 120                 125

```
His Thr Glu Ala Arg Ala Arg His Ala Trp Gln Leu Thr Gln Gly Ala
    130                 135                 140
Thr Val Leu Gly Leu Phe Arg Val Gly Ser Gly Ser Gly Asn Gly Ser
145                 150                 155                 160
Gln Gly Met Phe Ala Gln Leu Val Ala Gln Asn Val Leu Leu Ile Asp
                165                 170                 175
Gly Pro Leu Ser Trp Tyr Ser Asp Pro Gly Leu Ala Gly Val Ser Leu
            180                 185                 190
Thr Gly Gly Leu Ser Tyr Lys Glu Asp Thr Lys Glu Leu Val Val Ala
        195                 200                 205
Lys Ala Gly Val Tyr Tyr Val Phe Phe Gln Leu Glu Leu Arg Arg Val
    210                 215                 220
Val Ala Gly Glu Gly Ser Gly Ser Val Ser Leu Ala Leu His Leu Gln
225                 230                 235                 240
Pro Leu Arg Ser Ala Ala Gly Ala Ala Ala Leu Ala Leu Thr Val Asp
                245                 250                 255
Leu Pro Pro Ala Ser Ser Glu Ala Arg Asn Ser Ala Phe Gly Phe Gln
            260                 265                 270
Gly Arg Leu Leu His Leu Ser Ala Gly Gln Arg Leu Gly Val His Leu
        275                 280                 285
His Thr Glu Ala Arg Ala Arg His Ala Trp Gln Leu Thr Gln Gly Ala
    290                 295                 300
Thr Val Leu Gly Leu Phe Arg Val Gly Ser Gly Ser Gly Asn Gly Ser
305                 310                 315                 320
Gln Gly Met Phe Ala Gln Leu Val Ala Gln Asn Val Leu Leu Ile Asp
                325                 330                 335
Gly Pro Leu Ser Trp Tyr Ser Asp Pro Gly Leu Ala Gly Val Ser Leu
            340                 345                 350
Thr Gly Gly Leu Ser Tyr Lys Glu Asp Thr Lys Glu Leu Val Val Ala
        355                 360                 365
Lys Ala Gly Val Tyr Tyr Val Phe Phe Gln Leu Glu Leu Arg Arg Val
    370                 375                 380
Val Ala Gly Glu Gly Ser Gly Ser Val Ser Leu Ala Leu His Leu Gln
385                 390                 395                 400
Pro Leu Arg Ser Ala Ala Gly Ala Ala Ala Leu Ala Leu Thr Val Asp
                405                 410                 415
Leu Pro Pro Ala Ser Ser Glu Ala Arg Asn Ser Ala Phe Gly Phe Gln
            420                 425                 430
Gly Arg Leu Leu His Leu Ser Ala Gly Gln Arg Leu Gly Val His Leu
        435                 440                 445
His Thr Glu Ala Arg Ala Arg His Ala Trp Gln Leu Thr Gln Gly Ala
    450                 455                 460
Thr Val Leu Gly Leu Phe Arg Val Gly Ser Ser Ser Ser Ser Ser Ser
465                 470                 475                 480
Ser Gly Ser Cys Asp Lys Thr His Thr Cys Pro Pro Cys Pro Ala Pro
                485                 490                 495
Glu Leu Leu Gly Gly Pro Ser Val Phe Leu Phe Pro Pro Lys Pro Lys
            500                 505                 510
Asp Thr Leu Met Ile Ser Arg Thr Pro Glu Val Thr Cys Val Val Val
        515                 520                 525
Asp Val Ser His Glu Asp Pro Glu Val Lys Phe Asn Trp Tyr Val Asp
    530                 535                 540
```

```
Gly Val Glu Val His Asn Ala Lys Thr Lys Pro Arg Glu Glu Gln Tyr
545                 550                 555                 560

Ser Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
            580                 585                 590

Pro Ala Pro Ile Glu Lys Thr Ile Ser Lys Ala Lys Gly Gln Pro Arg
        595                 600                 605

Glu Pro Gln Val Tyr Thr Leu Pro Pro Ser Arg Glu Glu Met Thr Lys
    610                 615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
            660                 665                 670

Lys Leu Thr Val Asp Lys Ser Arg Trp Gln Gln Gly Asn Val Phe Ser
        675                 680                 685

Cys Ser Val Met His Glu Ala Leu His Asn His Tyr Thr Gln Lys Ser
690                 695                 700

Leu Ser Leu Ser Pro Gly Lys
705                 710

<210> SEQ ID NO 28
<211> LENGTH: 725
<212> TYPE: PRT
<213> ORGANISM: Artificial Sequence
<220> FEATURE:
<223> OTHER INFORMATION: CD137L-wt fused to Seq_13 (no sig, no glyco)

<400> SEQUENCE: 28

Gln Gly Met Phe Ala Gln Leu Val Ala Gln Asn Val Leu Leu Ile Asp
1               5                   10                  15

Gly Pro Leu Ser Trp Tyr Ser Asp Pro Gly Leu Ala Gly Val Ser Leu
            20                  25                  30

Thr Gly Gly Leu Ser Tyr Lys Glu Asp Thr Lys Glu Leu Val Val Ala
        35                  40                  45

Lys Ala Gly Val Tyr Tyr Val Phe Phe Gln Leu Glu Leu Arg Arg Val
    50                  55                  60

Val Ala Gly Glu Gly Ser Gly Ser Val Ser Leu Ala Leu His Leu Gln
65                  70                  75                  80

Pro Leu Arg Ser Ala Ala Gly Ala Ala Ala Leu Ala Leu Thr Val Asp
                85                  90                  95

Leu Pro Pro Ala Ser Ser Glu Ala Arg Asn Ser Ala Phe Gly Phe Gln
            100                 105                 110

Gly Arg Leu Leu His Leu Ser Ala Gly Gln Arg Leu Gly Val His Leu
        115                 120                 125

His Thr Glu Ala Arg Ala Arg His Ala Trp Gln Leu Thr Gln Gly Ala
    130                 135                 140

Thr Val Leu Gly Leu Phe Arg Val Gly Ser Gly Ser Gly Asn Gly Ser
145                 150                 155                 160

Gln Gly Met Phe Ala Gln Leu Val Ala Gln Asn Val Leu Leu Ile Asp
                165                 170                 175

Gly Pro Leu Ser Trp Tyr Ser Asp Pro Gly Leu Ala Gly Val Ser Leu
            180                 185                 190
```

```
Thr Gly Gly Leu Ser Tyr Lys Glu Asp Thr Lys Glu Leu Val Val Ala
            195                 200                 205

Lys Ala Gly Val Tyr Tyr Val Phe Phe Gln Leu Glu Leu Arg Arg Val
        210                 215                 220

Val Ala Gly Glu Gly Ser Gly Ser Val Ser Leu Ala Leu His Leu Gln
225                 230                 235                 240

Pro Leu Arg Ser Ala Ala Gly Ala Ala Ala Leu Ala Leu Thr Val Asp
                245                 250                 255

Leu Pro Pro Ala Ser Ser Glu Ala Arg Asn Ser Ala Phe Gly Phe Gln
                260                 265                 270

Gly Arg Leu Leu His Leu Ser Ala Gly Gln Arg Leu Gly Val His Leu
                275                 280                 285

His Thr Glu Ala Arg Ala Arg His Ala Trp Gln Leu Thr Gln Gly Ala
        290                 295                 300

Thr Val Leu Gly Leu Phe Arg Val Gly Ser Ser Gly Asn Gly Ser
305                 310                 315                 320

Gln Gly Met Phe Ala Gln Leu Val Ala Gln Asn Val Leu Leu Ile Asp
                325                 330                 335

Gly Pro Leu Ser Trp Tyr Ser Asp Pro Gly Leu Ala Gly Val Ser Leu
                340                 345                 350

Thr Gly Gly Leu Ser Tyr Lys Glu Asp Thr Lys Glu Leu Val Val Ala
            355                 360                 365

Lys Ala Gly Val Tyr Tyr Val Phe Phe Gln Leu Glu Leu Arg Arg Val
        370                 375                 380

Val Ala Gly Glu Gly Ser Gly Ser Val Ser Leu Ala Leu His Leu Gln
385                 390                 395                 400

Pro Leu Arg Ser Ala Ala Gly Ala Ala Ala Leu Ala Leu Thr Val Asp
                405                 410                 415

Leu Pro Pro Ala Ser Ser Glu Ala Arg Asn Ser Ala Phe Gly Phe Gln
                420                 425                 430

Gly Arg Leu Leu His Leu Ser Ala Gly Gln Arg Leu Gly Val His Leu
                435                 440                 445

His Thr Glu Ala Arg Ala Arg His Ala Trp Gln Leu Thr Gln Gly Ala
        450                 455                 460

Thr Val Leu Gly Leu Phe Arg Val Gly Ser Ser Ser Ser Ser Ser
465                 470                 475                 480

Ser Gly Ser Cys Asp Lys Thr His Thr Cys Pro Pro Cys Pro Ala Pro
                485                 490                 495

Glu Leu Leu Gly Gly Pro Ser Val Phe Leu Phe Pro Pro Lys Pro Lys
                500                 505                 510

Asp Thr Leu Met Ile Ser Arg Thr Pro Glu Val Thr Cys Val Val Val
                515                 520                 525

Asp Val Ser His Glu Asp Pro Glu Val Lys Phe Asn Trp Tyr Val Asp
                530                 535                 540

Gly Val Glu Val His Asn Ala Lys Thr Lys Pro Arg Glu Glu Gln Tyr
545                 550                 555                 560

Ser Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
                580                 585                 590

Pro Ala Pro Ile Glu Lys Thr Ile Ser Lys Ala Lys Gly Gln Pro Arg
                595                 600                 605

Glu Pro Gln Val Tyr Thr Leu Pro Pro Ser Arg Glu Glu Met Thr Lys
```

```
                610             615             620
Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
                660                 665                 670

Lys Leu Thr Val Asp Lys Ser Arg Trp Gln Gln Gly Asn Val Phe Ser
                675                 680                 685

Cys Ser Val Met His Glu Ala Leu His Asn His Tyr Thr Gln Lys Ser
                690                 695                 700

Leu Ser Leu Ser Pro Gly Ser Ser Ser Ser Ser Ala Trp Ser His
705                 710                 715                 720

Pro Gln Phe Glu Lys
                725

<210> SEQ ID NO 29
<211> LENGTH: 710
<212> TYPE: PRT
<213> ORGANISM: Artificial Sequence
<220> FEATURE:
<223> OTHER INFORMATION: example

<400> SEQUENCE: 29

Gln Gly Met Phe Ala Gln Leu Val Ala Gln Asn Val Leu Leu Ile Asp
1               5                   10                  15

Gly Pro Leu Ser Trp Tyr Ser Asp Pro Gly Leu Ala Gly Val Ser Leu
                20                  25                  30

Thr Gly Gly Leu Ser Tyr Lys Glu Asp Thr Lys Glu Leu Val Val Ala
            35                  40                  45

Lys Ala Gly Val Tyr Tyr Val Phe Phe Gln Leu Glu Leu Arg Arg Val
        50                  55                  60

Val Ala Gly Glu Gly Ser Gly Ser Val Ser Leu Ala Leu His Leu Gln
65                  70                  75                  80

Pro Leu Arg Ser Ala Ala Gly Ala Ala Ala Leu Ala Leu Thr Val Asp
                85                  90                  95

Leu Pro Pro Ala Ser Ser Glu Ala Arg Asn Ser Ala Phe Gly Phe Gln
                100                 105                 110

Gly Arg Leu Leu His Leu Ser Ala Gly Gln Arg Leu Gly Val His Leu
            115                 120                 125

His Thr Glu Ala Arg Ala Arg His Ala Trp Gln Leu Thr Gln Gly Ala
        130                 135                 140

Thr Val Leu Gly Leu Phe Arg Val Gly Ser Gly Ser Gly Asn Gly Ser
145                 150                 155                 160

Gln Gly Met Phe Ala Gln Leu Val Ala Gln Asn Val Leu Leu Ile Asp
                165                 170                 175

Gly Pro Leu Ser Trp Tyr Ser Asp Pro Gly Leu Ala Gly Val Ser Leu
                180                 185                 190

Thr Gly Gly Leu Ser Tyr Lys Glu Asp Thr Lys Glu Leu Val Val Ala
            195                 200                 205

Lys Ala Gly Val Tyr Tyr Val Phe Phe Gln Leu Glu Leu Arg Arg Val
        210                 215                 220

Val Ala Gly Glu Gly Ser Gly Ser Val Ser Leu Ala Leu His Leu Gln
225                 230                 235                 240

Pro Leu Arg Ser Ala Ala Gly Ala Ala Ala Leu Ala Leu Thr Val Asp
```

```
                245                 250                 255
Leu Pro Pro Ala Ser Ser Glu Ala Arg Asn Ser Ala Phe Gly Phe Gln
            260                 265                 270
Gly Arg Leu Leu His Leu Ser Ala Gly Gln Arg Leu Gly Val His Leu
        275                 280                 285
His Thr Glu Ala Arg Ala Arg His Ala Trp Gln Leu Thr Gln Gly Ala
    290                 295                 300
Thr Val Leu Gly Leu Phe Arg Val Gly Ser Gly Ser Gly Asn Gly Ser
305                 310                 315                 320
Gln Gly Met Phe Ala Gln Leu Val Ala Gln Asn Val Leu Leu Ile Asp
                325                 330                 335
Gly Pro Leu Ser Trp Tyr Ser Asp Pro Gly Leu Ala Gly Val Ser Leu
            340                 345                 350
Thr Gly Gly Leu Ser Tyr Lys Glu Asp Thr Lys Glu Leu Val Val Ala
        355                 360                 365
Lys Ala Gly Val Tyr Tyr Val Phe Phe Gln Leu Glu Leu Arg Arg Val
    370                 375                 380
Val Ala Gly Glu Gly Ser Gly Ser Val Ser Leu Ala Leu His Leu Gln
385                 390                 395                 400
Pro Leu Arg Ser Ala Ala Gly Ala Ala Ala Leu Ala Leu Thr Val Asp
                405                 410                 415
Leu Pro Pro Ala Ser Ser Glu Ala Arg Asn Ser Ala Phe Gly Phe Gln
            420                 425                 430
Gly Arg Leu Leu His Leu Ser Ala Gly Gln Arg Leu Gly Val His Leu
        435                 440                 445
His Thr Glu Ala Arg Ala Arg His Ala Trp Gln Leu Thr Gln Gly Ala
    450                 455                 460
Thr Val Leu Gly Leu Phe Arg Val Gly Ser Ser Ser Ser Ser Ser Ser
465                 470                 475                 480
Ser Gly Ser Cys Asp Lys Thr His Thr Cys Pro Pro Cys Pro Ala Pro
                485                 490                 495
Pro Val Ala Gly Pro Ser Val Phe Leu Phe Pro Pro Lys Pro Lys Asp
            500                 505                 510
Thr Leu Met Ile Ser Arg Thr Pro Glu Val Thr Cys Val Val Val Asp
        515                 520                 525
Val Ser His Glu Asp Pro Glu Val Lys Phe Asn Trp Tyr Val Asp Gly
    530                 535                 540
Val Glu Val His Asn Ala Lys Thr Lys Pro Arg Glu Glu Gln Tyr Asn
545                 550                 555                 560
Ser Thr Tyr Arg Val Val Ser Val Leu Thr Val Leu His Gln Asp Trp
                565                 570                 575
Leu Asn Gly Lys Glu Tyr Lys Cys Lys Val Ser Asn Lys Gly Leu Pro
            580                 585                 590
Ser Ser Ile Glu Lys Thr Ile Ser Lys Ala Lys Gly Gln Pro Arg Glu
        595                 600                 605
Pro Gln Val Tyr Thr Leu Pro Pro Ser Arg Glu Glu Met Thr Lys Asn
    610                 615                 620
Gln Val Ser Leu Thr Cys Leu Val Lys Gly Phe Tyr Pro Ser Asp Ile
625                 630                 635                 640
Ala Val Glu Trp Glu Ser Asn Gly Gln Pro Glu Asn Asn Tyr Lys Thr
                645                 650                 655
Thr Pro Pro Val Leu Asp Ser Asp Gly Ser Phe Phe Leu Tyr Ser Lys
            660                 665                 670
```

```
Leu Thr Val Asp Lys Ser Arg Trp Gln Gln Gly Asn Val Phe Ser Cys
        675                 680                 685
Ser Val Met His Glu Ala Leu His Asn His Tyr Thr Gln Lys Ser Leu
        690                 695                 700
Ser Leu Ser Pro Gly Lys
705             710
```

<210> SEQ ID NO 30
<211> LENGTH: 716
<212> TYPE: PRT
<213> ORGANISM: Artificial Sequence
<220> FEATURE:
<223> OTHER INFORMATION: example

<400> SEQUENCE: 30

```
Gln Leu Arg Gln Gly Met Phe Ala Gln Leu Val Ala Gln Asn Val Leu
1               5                   10                  15
Leu Ile Asp Gly Pro Leu Ser Trp Tyr Ser Asp Pro Gly Leu Ala Gly
            20                  25                  30
Val Ser Leu Thr Gly Gly Leu Ser Tyr Lys Glu Asp Thr Lys Glu Leu
        35                  40                  45
Val Val Ala Lys Ala Gly Val Tyr Tyr Val Phe Phe Gln Leu Glu Leu
    50                  55                  60
Arg Arg Val Val Ala Gly Glu Gly Ser Gly Ser Val Ser Leu Ala Leu
65                  70                  75                  80
His Leu Gln Pro Leu Arg Ser Ala Ala Gly Ala Ala Leu Ala Leu
                85                  90                  95
Thr Val Asp Leu Pro Pro Ala Ser Ser Glu Ala Arg Asn Ser Ala Phe
            100                 105                 110
Gly Phe Gln Gly Arg Leu Leu His Leu Ser Ala Gly Gln Arg Leu Gly
        115                 120                 125
Val His Leu His Thr Glu Ala Arg Ala Arg His Ala Trp Gln Leu Thr
    130                 135                 140
Gln Gly Ala Thr Val Leu Gly Leu Phe Arg Val Gly Ser Gly Ser Gly
145                 150                 155                 160
Asn Gly Ser Asp Leu Arg Gln Gly Met Phe Ala Gln Leu Val Ala Gln
                165                 170                 175
Asn Val Leu Leu Ile Asp Gly Pro Leu Ser Trp Tyr Ser Asp Pro Gly
            180                 185                 190
Leu Ala Gly Val Ser Leu Thr Gly Gly Leu Ser Tyr Lys Glu Asp Thr
        195                 200                 205
Lys Glu Leu Val Val Ala Lys Ala Gly Val Tyr Tyr Val Phe Phe Gln
    210                 215                 220
Leu Glu Leu Arg Arg Val Val Ala Gly Glu Gly Ser Gly Ser Val Ser
225                 230                 235                 240
Leu Ala Leu His Leu Gln Pro Leu Arg Ser Ala Ala Gly Ala Ala Ala
                245                 250                 255
Leu Ala Leu Thr Val Asp Leu Pro Pro Ala Ser Ser Glu Ala Arg Asn
            260                 265                 270
Ser Ala Phe Gly Phe Gln Gly Arg Leu Leu His Leu Ser Ala Gly Gln
        275                 280                 285
Arg Leu Gly Val His Leu His Thr Glu Ala Arg Ala Arg His Ala Trp
    290                 295                 300
Gln Leu Thr Gln Gly Ala Thr Val Leu Gly Leu Phe Arg Val Gly Ser
305                 310                 315                 320
```

```
Gly Ser Gly Asn Gly Ser Asp Leu Arg Gln Gly Met Phe Ala Gln Leu
                325                 330                 335

Val Ala Gln Asn Val Leu Leu Ile Asp Gly Pro Leu Ser Trp Tyr Ser
                340                 345                 350

Asp Pro Gly Leu Ala Gly Val Ser Leu Thr Gly Gly Leu Ser Tyr Lys
                355                 360                 365

Glu Asp Thr Lys Glu Leu Val Ala Lys Ala Gly Val Tyr Tyr Val
            370                 375                 380

Phe Phe Gln Leu Glu Leu Arg Arg Val Val Ala Gly Glu Gly Ser Gly
385                 390                 395                 400

Ser Val Ser Leu Ala Leu His Leu Gln Pro Leu Arg Ser Ala Ala Gly
                405                 410                 415

Ala Ala Ala Leu Ala Leu Thr Val Asp Leu Pro Pro Ala Ser Ser Glu
                420                 425                 430

Ala Arg Asn Ser Ala Phe Gly Phe Gln Gly Arg Leu Leu His Leu Ser
                435                 440                 445

Ala Gly Gln Arg Leu Gly Val His Leu His Thr Glu Ala Arg Ala Arg
            450                 455                 460

His Ala Trp Gln Leu Thr Gln Gly Ala Thr Val Leu Gly Leu Phe Arg
465                 470                 475                 480

Val Gly Ser Ser Ser Gly Ser Cys Asp Lys Thr His Thr Cys Pro
                485                 490                 495

Pro Cys Pro Ala Pro Glu Leu Leu Gly Gly Pro Ser Val Phe Leu Phe
                500                 505                 510

Pro Pro Lys Pro Lys Asp Thr Leu Met Ile Ser Arg Thr Pro Glu Val
                515                 520                 525

Thr Cys Val Val Val Asp Val Ser His Glu Asp Pro Glu Val Lys Phe
                530                 535                 540

Asn Trp Tyr Val Asp Gly Val Glu Val His Asn Ala Lys Thr Lys Pro
545                 550                 555                 560

Arg Glu Glu Gln Tyr Ser Ser Thr Tyr Arg Val Val Ser Val Leu Thr
                565                 570                 575

Val Leu His Gln Asp Trp Leu Asn Gly Lys Glu Tyr Lys Cys Lys Val
                580                 585                 590

Ser Asn Lys Ala Leu Pro Ala Pro Ile Glu Lys Thr Ile Ser Lys Ala
                595                 600                 605

Lys Gly Gln Pro Arg Glu Pro Gln Val Tyr Thr Leu Pro Pro Ser Arg
            610                 615                 620

Glu Glu Met Thr Lys Asn Gln Val Ser Leu Thr Cys Leu Val Lys Gly
625                 630                 635                 640

Phe Tyr Pro Ser Asp Ile Ala Val Glu Trp Glu Ser Asn Gly Gln Pro
                645                 650                 655

Glu Asn Asn Tyr Lys Thr Thr Pro Pro Val Leu Asp Ser Asp Gly Ser
                660                 665                 670

Phe Phe Leu Tyr Ser Lys Leu Thr Val Asp Lys Ser Arg Trp Gln Gln
                675                 680                 685

Gly Asn Val Phe Ser Cys Ser Val Met His Glu Ala Leu His Asn His
                690                 695                 700

Tyr Thr Gln Lys Ser Leu Ser Leu Ser Pro Gly Lys
705                 710                 715

<210> SEQ ID NO 31
<211> LENGTH: 720
```

```
<212> TYPE: PRT
<213> ORGANISM: Artificial Sequence
<220> FEATURE:
<223> OTHER INFORMATION: example

<400> SEQUENCE: 31
```

| | | | | | | | | | | | | | | |
|---|---|---|---|---|---|---|---|---|---|---|---|---|---|---|
| Gln | Leu | Arg | Gln | Gly | Met | Phe | Ala | Gln | Leu | Val | Ala | Gln | Asn | Val | Leu |
| 1 | | | | 5 | | | | | 10 | | | | | 15 | |
| Leu | Ile | Asp | Gly | Pro | Leu | Ser | Trp | Tyr | Ser | Asp | Pro | Gly | Leu | Ala | Gly |
| | | | 20 | | | | | 25 | | | | | 30 | | |
| Val | Ser | Leu | Thr | Gly | Gly | Leu | Ser | Tyr | Lys | Glu | Asp | Thr | Lys | Glu | Leu |
| | | | 35 | | | | | 40 | | | | | 45 | | |
| Val | Val | Ala | Lys | Ala | Gly | Val | Tyr | Tyr | Val | Phe | Phe | Gln | Leu | Glu | Leu |
| | 50 | | | | | 55 | | | | | 60 | | | | |
| Arg | Arg | Val | Val | Ala | Gly | Glu | Gly | Ser | Gly | Ser | Val | Ser | Leu | Ala | Leu |
| 65 | | | | | 70 | | | | | 75 | | | | | 80 |
| His | Leu | Gln | Pro | Leu | Arg | Ser | Ala | Ala | Gly | Ala | Ala | Leu | Ala | Leu |
| | | | | 85 | | | | | 90 | | | | | 95 |
| Thr | Val | Asp | Leu | Pro | Pro | Ala | Ser | Ser | Glu | Ala | Arg | Asn | Ser | Ala | Phe |
| | | | 100 | | | | | 105 | | | | | 110 | | |
| Gly | Phe | Gln | Gly | Arg | Leu | Leu | His | Leu | Ser | Ala | Gly | Gln | Arg | Leu | Gly |
| | | | 115 | | | | | 120 | | | | | 125 | | |
| Val | His | Leu | His | Thr | Glu | Ala | Arg | Ala | Arg | His | Ala | Trp | Gln | Leu | Thr |
| | 130 | | | | | 135 | | | | | 140 | | | | |
| Gln | Gly | Ala | Thr | Val | Leu | Gly | Leu | Phe | Arg | Val | Gly | Ser | Gly | Ser | Gly |
| 145 | | | | | 150 | | | | | 155 | | | | | 160 |
| Asn | Gly | Ser | Asp | Leu | Arg | Gln | Gly | Met | Phe | Ala | Gln | Leu | Val | Ala | Gln |
| | | | | 165 | | | | | 170 | | | | | 175 | |
| Asn | Val | Leu | Leu | Ile | Asp | Gly | Pro | Leu | Ser | Trp | Tyr | Ser | Asp | Pro | Gly |
| | | | 180 | | | | | 185 | | | | | 190 | | |
| Leu | Ala | Gly | Val | Ser | Leu | Thr | Gly | Gly | Leu | Ser | Tyr | Lys | Glu | Asp | Thr |
| | | | 195 | | | | | 200 | | | | | 205 | | |
| Lys | Glu | Leu | Val | Val | Ala | Lys | Ala | Gly | Val | Tyr | Tyr | Val | Phe | Phe | Gln |
| | 210 | | | | | 215 | | | | | 220 | | | | |
| Leu | Glu | Leu | Arg | Arg | Val | Val | Ala | Gly | Glu | Gly | Ser | Gly | Ser | Val | Ser |
| 225 | | | | | 230 | | | | | 235 | | | | | 240 |
| Leu | Ala | Leu | His | Leu | Gln | Pro | Leu | Arg | Ser | Ala | Ala | Gly | Ala | Ala | Ala |
| | | | | 245 | | | | | 250 | | | | | 255 | |
| Leu | Ala | Leu | Thr | Val | Asp | Leu | Pro | Pro | Ala | Ser | Ser | Glu | Ala | Arg | Asn |
| | | | 260 | | | | | 265 | | | | | 270 | | |
| Ser | Ala | Phe | Gly | Phe | Gln | Gly | Arg | Leu | Leu | His | Leu | Ser | Ala | Gly | Gln |
| | | | 275 | | | | | 280 | | | | | 285 | | |
| Arg | Leu | Gly | Val | His | Leu | His | Thr | Glu | Ala | Arg | Ala | Arg | His | Ala | Trp |
| | 290 | | | | | 295 | | | | | 300 | | | | |
| Gln | Leu | Thr | Gln | Gly | Ala | Thr | Val | Leu | Gly | Leu | Phe | Arg | Val | Gly | Ser |
| 305 | | | | | 310 | | | | | 315 | | | | | 320 |
| Gly | Ser | Gly | Asn | Gly | Ser | Asp | Leu | Arg | Gln | Gly | Met | Phe | Ala | Gln | Leu |
| | | | | 325 | | | | | 330 | | | | | 335 | |
| Val | Ala | Gln | Asn | Val | Leu | Leu | Ile | Asp | Gly | Pro | Leu | Ser | Trp | Tyr | Ser |
| | | | 340 | | | | | 345 | | | | | 350 | | |
| Asp | Pro | Gly | Leu | Ala | Gly | Val | Ser | Leu | Thr | Gly | Gly | Leu | Ser | Tyr | Lys |
| | | | 355 | | | | | 360 | | | | | 365 | | |
| Glu | Asp | Thr | Lys | Glu | Leu | Val | Val | Ala | Lys | Ala | Gly | Val | Tyr | Tyr | Val |
| | 370 | | | | | 375 | | | | | 380 | | | | |

Phe Phe Gln Leu Glu Leu Arg Arg Val Val Ala Gly Glu Gly Ser Gly
385                 390                 395                 400

Ser Val Ser Leu Ala Leu His Leu Gln Pro Leu Arg Ser Ala Ala Gly
            405                 410                 415

Ala Ala Ala Leu Ala Leu Thr Val Asp Leu Pro Pro Ala Ser Ser Glu
        420                 425                 430

Ala Arg Asn Ser Ala Phe Gly Phe Gln Gly Arg Leu Leu His Leu Ser
    435                 440                 445

Ala Gly Gln Arg Leu Gly Val His Leu His Thr Glu Ala Arg Ala Arg
450                 455                 460

His Ala Trp Gln Leu Thr Gln Gly Ala Thr Val Leu Gly Leu Phe Arg
465                 470                 475                 480

Val Gly Ser Ser Ser Ser Ser Ser Gly Ser Cys Asp Lys Thr
                485                 490                 495

His Thr Cys Pro Pro Cys Pro Ala Pro Glu Leu Leu Gly Gly Pro Ser
            500                 505                 510

Val Phe Leu Phe Pro Pro Lys Pro Lys Asp Thr Leu Met Ile Ser Arg
        515                 520                 525

Thr Pro Glu Val Thr Cys Val Val Asp Val Ser His Glu Asp Pro
    530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
        595                 600                 605

Ile Ser Lys Ala Lys Gly Gln Pro Arg Glu Pro Gln Val Tyr Thr Leu
    610                 615                 620

Pro Pro Ser Arg Glu Glu Met Thr Lys Asn Gln Val Ser Leu Thr Cys
625                 630                 635                 640

Leu Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720

<210> SEQ ID NO 32
<211> LENGTH: 711
<212> TYPE: PRT
<213> ORGANISM: Artificial Sequence
<220> FEATURE:
<223> OTHER INFORMATION: example

<400> SEQUENCE: 32

Arg Gln Gly Met Phe Ala Gln Leu Val Ala Gln Asn Val Leu Leu Ile
1               5                   10                  15

Asp Gly Pro Leu Ser Trp Tyr Ser Asp Pro Gly Leu Ala Gly Val Ser
            20                  25                  30

```
Leu Thr Gly Gly Leu Ser Tyr Lys Glu Asp Thr Lys Glu Leu Val Val
             35                  40                  45

Ala Lys Ala Gly Val Tyr Tyr Val Phe Phe Gln Leu Glu Leu Arg Arg
 50                  55                  60

Val Val Ala Gly Glu Gly Ser Gly Ser Val Ser Leu Ala Leu His Leu
 65                  70                  75                  80

Gln Pro Leu Arg Ser Ala Ala Gly Ala Ala Ala Leu Ala Leu Thr Val
             85                  90                  95

Asp Leu Pro Pro Ala Ser Ser Glu Ala Arg Asn Ser Ala Phe Gly Phe
            100                 105                 110

Gln Gly Arg Leu Leu His Leu Ser Ala Gly Gln Arg Leu Gly Val His
            115                 120                 125

Leu His Thr Glu Ala Arg Ala Arg His Ala Trp Gln Leu Thr Gln Gly
        130                 135                 140

Ala Thr Val Leu Gly Leu Phe Arg Val Gly Ser Gly Ser Gly Asn Gly
145                 150                 155                 160

Ser Arg Gln Gly Met Phe Ala Gln Leu Val Ala Gln Asn Val Leu Leu
                165                 170                 175

Ile Asp Gly Pro Leu Ser Trp Tyr Ser Asp Pro Gly Leu Ala Gly Val
            180                 185                 190

Ser Leu Thr Gly Gly Leu Ser Tyr Lys Glu Asp Thr Lys Glu Leu Val
            195                 200                 205

Val Ala Lys Ala Gly Val Tyr Tyr Val Phe Phe Gln Leu Glu Leu Arg
        210                 215                 220

Arg Val Val Ala Gly Glu Gly Ser Gly Ser Val Ser Leu Ala Leu His
225                 230                 235                 240

Leu Gln Pro Leu Arg Ser Ala Ala Gly Ala Ala Ala Leu Ala Leu Thr
                245                 250                 255

Val Asp Leu Pro Pro Ala Ser Ser Glu Ala Arg Asn Ser Ala Phe Gly
            260                 265                 270

Phe Gln Gly Arg Leu Leu His Leu Ser Ala Gly Gln Arg Leu Gly Val
            275                 280                 285

His Leu His Thr Glu Ala Arg Ala Arg His Ala Trp Gln Leu Thr Gln
        290                 295                 300

Gly Ala Thr Val Leu Gly Leu Phe Arg Val Gly Ser Gly Ser Gly Asn
305                 310                 315                 320

Gly Ser Arg Gln Gly Met Phe Ala Gln Leu Val Ala Gln Asn Val Leu
                325                 330                 335

Leu Ile Asp Gly Pro Leu Ser Trp Tyr Ser Asp Pro Gly Leu Ala Gly
            340                 345                 350

Val Ser Leu Thr Gly Gly Leu Ser Tyr Lys Glu Asp Thr Lys Glu Leu
            355                 360                 365

Val Val Ala Lys Ala Gly Val Tyr Tyr Val Phe Phe Gln Leu Glu Leu
        370                 375                 380

Arg Arg Val Val Ala Gly Glu Gly Ser Gly Ser Val Ser Leu Ala Leu
385                 390                 395                 400

His Leu Gln Pro Leu Arg Ser Ala Ala Gly Ala Ala Ala Leu Ala Leu
                405                 410                 415

Thr Val Asp Leu Pro Pro Ala Ser Ser Glu Ala Arg Asn Ser Ala Phe
            420                 425                 430

Gly Phe Gln Gly Arg Leu Leu His Leu Ser Ala Gly Gln Arg Leu Gly
            435                 440                 445

Val His Leu His Thr Glu Ala Arg Ala Arg His Ala Trp Gln Leu Thr
```

-continued

```
                450                 455                 460
Gln Gly Ala Thr Val Leu Gly Leu Phe Arg Val Gly Ser Ser Ser Ser
465                 470                 475                 480

Ser Gly Ser Cys Asp Lys Thr His Thr Cys Pro Pro Cys Pro Ala Pro
                485                 490                 495

Glu Leu Leu Gly Gly Pro Ser Val Phe Leu Phe Pro Pro Lys Pro Lys
                500                 505                 510

Asp Thr Leu Met Ile Ser Arg Thr Pro Glu Val Thr Cys Val Val Val
                515                 520                 525

Asp Val Ser His Glu Asp Pro Glu Val Lys Phe Asn Trp Tyr Val Asp
                530                 535                 540

Gly Val Glu Val His Asn Ala Lys Thr Lys Pro Arg Glu Glu Gln Tyr
545                 550                 555                 560

Ser Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
                580                 585                 590

Pro Ala Pro Ile Glu Lys Thr Ile Ser Lys Ala Lys Gly Gln Pro Arg
                595                 600                 605

Glu Pro Gln Val Tyr Thr Leu Pro Pro Ser Arg Glu Glu Met Thr Lys
                610                 615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
                660                 665                 670

Lys Leu Thr Val Asp Lys Ser Arg Trp Gln Gln Gly Asn Val Phe Ser
                675                 680                 685

Cys Ser Val Met His Glu Ala Leu His Asn His Tyr Thr Gln Lys Ser
                690                 695                 700

Leu Ser Leu Ser Pro Gly Lys
705                 710

<210> SEQ ID NO 33
<211> LENGTH: 714
<212> TYPE: PRT
<213> ORGANISM: Artificial Sequence
<220> FEATURE:
<223> OTHER INFORMATION: example

<400> SEQUENCE: 33

Gln Gln Gly Met Phe Ala Gln Leu Val Ala Gln Asn Val Leu Leu Ile
1               5                   10                  15

Asp Gly Pro Leu Ser Trp Tyr Ser Asp Pro Gly Leu Ala Gly Val Ser
                20                  25                  30

Leu Thr Gly Gly Leu Ser Tyr Lys Glu Asp Thr Lys Glu Leu Val Val
            35                  40                  45

Ala Lys Ala Gly Val Tyr Tyr Val Phe Phe Gln Leu Glu Leu Arg Arg
        50                  55                  60

Val Val Ala Gly Glu Gly Ser Gly Ser Val Ser Leu Ala Leu His Leu
65                  70                  75                  80

Gln Pro Leu Arg Ser Ala Ala Gly Ala Ala Ala Leu Ala Leu Thr Val
                85                  90                  95

Asp Leu Pro Pro Ala Ser Ser Glu Ala Arg Asn Ser Ala Phe Gly Phe
```

```
                100                 105                 110
        Gln Gly Arg Leu Leu His Leu Ser Ala Gly Gln Arg Leu Gly Val His
                    115                 120                 125

Leu His Thr Glu Ala Arg Ala Arg His Ala Trp Gln Leu Thr Gln Gly
            130                 135                 140

Ala Thr Val Leu Gly Leu Phe Arg Val Gly Ser Gly Ser Gly Asn Gly
        145                 150                 155                 160

Ser Gly Gln Gly Met Phe Ala Gln Leu Val Ala Gln Asn Val Leu Leu
                        165                 170                 175

Ile Asp Gly Pro Leu Ser Trp Tyr Ser Asp Pro Gly Leu Ala Gly Val
                    180                 185                 190

Ser Leu Thr Gly Gly Leu Ser Tyr Lys Glu Asp Thr Lys Glu Leu Val
                    195                 200                 205

Val Ala Lys Ala Gly Val Tyr Tyr Val Phe Phe Gln Leu Glu Leu Arg
                    210                 215                 220

Arg Val Val Ala Gly Glu Gly Ser Gly Ser Val Ser Leu Ala Leu His
        225                 230                 235                 240

Leu Gln Pro Leu Arg Ser Ala Ala Gly Ala Ala Leu Ala Leu Thr
                        245                 250                 255

Val Asp Leu Pro Pro Ala Ser Ser Glu Ala Arg Asn Ser Ala Phe Gly
                    260                 265                 270

Phe Gln Gly Arg Leu Leu His Leu Ser Ala Gly Gln Arg Leu Gly Val
                    275                 280                 285

His Leu His Thr Glu Ala Arg Ala Arg His Ala Trp Gln Leu Thr Gln
                290                 295                 300

Gly Ala Thr Val Leu Gly Leu Phe Arg Val Gly Ser Gly Ser Gly Asn
        305                 310                 315                 320

Gly Ser Gly Gln Gly Met Phe Ala Gln Leu Val Ala Gln Asn Val Leu
                        325                 330                 335

Leu Ile Asp Gly Pro Leu Ser Trp Tyr Ser Asp Pro Gly Leu Ala Gly
                        340                 345                 350

Val Ser Leu Thr Gly Gly Leu Ser Tyr Lys Glu Asp Thr Lys Glu Leu
                    355                 360                 365

Val Val Ala Lys Ala Gly Val Tyr Tyr Val Phe Phe Gln Leu Glu Leu
                    370                 375                 380

Arg Arg Val Val Ala Gly Glu Gly Ser Gly Ser Val Ser Leu Ala Leu
        385                 390                 395                 400

His Leu Gln Pro Leu Arg Ser Ala Ala Gly Ala Ala Leu Ala Leu
                        405                 410                 415

Thr Val Asp Leu Pro Pro Ala Ser Ser Glu Ala Arg Asn Ser Ala Phe
                        420                 425                 430

Gly Phe Gln Gly Arg Leu Leu His Leu Ser Ala Gly Gln Arg Leu Gly
                    435                 440                 445

Val His Leu His Thr Glu Ala Arg Ala Arg His Ala Trp Gln Leu Thr
                    450                 455                 460

Gln Gly Ala Thr Val Leu Gly Leu Phe Arg Val Gly Ser Ser Ser Ser
        465                 470                 475                 480

Ser Ser Ser Ser Gly Ser Cys Asp Lys Thr His Thr Cys Pro Pro Cys
                        485                 490                 495

Pro Ala Pro Glu Leu Leu Gly Gly Pro Ser Val Phe Leu Phe Pro Pro
                    500                 505                 510

Lys Pro Lys Asp Thr Leu Met Ile Ser Arg Thr Pro Glu Val Thr Cys
                    515                 520                 525
```

```
Val Val Val Asp Val Ser His Glu Asp Pro Glu Val Lys Phe Asn Trp
            530                 535                 540

Tyr Val Asp Gly Val Glu Val His Asn Ala Lys Thr Lys Pro Arg Glu
545                 550                 555                 560

Glu Gln Tyr Ser Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
        595                 600                 605

Gln Pro Arg Glu Pro Gln Val Tyr Thr Leu Pro Pro Ser Arg Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
    690                 695                 700

Gln Lys Ser Leu Ser Leu Ser Pro Gly Lys
705                 710

<210> SEQ ID NO 34
<211> LENGTH: 714
<212> TYPE: PRT
<213> ORGANISM: Artificial Sequence
<220> FEATURE:
<223> OTHER INFORMATION: example

<400> SEQUENCE: 34

Ser Gln Gly Met Phe Ala Gln Leu Val Ala Gln Asn Val Leu Leu Ile
1               5                   10                  15

Asp Gly Pro Leu Ser Trp Tyr Ser Asp Pro Gly Leu Ala Gly Val Ser
                20                  25                  30

Leu Thr Gly Gly Leu Ser Tyr Lys Glu Asp Thr Lys Glu Leu Val Val
            35                  40                  45

Ala Lys Ala Gly Val Tyr Tyr Val Phe Phe Gln Leu Glu Leu Arg Arg
        50                  55                  60

Val Val Ala Gly Glu Gly Ser Gly Ser Val Ser Leu Ala Leu His Leu
65                  70                  75                  80

Gln Pro Leu Arg Ser Ala Gly Ala Ala Leu Ala Leu Thr Val
                85                  90                  95

Asp Leu Pro Pro Ala Ser Ser Glu Ala Arg Asn Ser Ala Phe Gly Phe
                100                 105                 110

Gln Gly Arg Leu Leu His Leu Ser Ala Gly Gln Arg Leu Gly Val His
            115                 120                 125

Leu His Thr Glu Ala Arg Ala Arg His Ala Trp Gln Leu Thr Gln Gly
        130                 135                 140

Ala Thr Val Leu Gly Leu Phe Arg Val Gly Ser Gly Ser Gly Asn Gly
145                 150                 155                 160

Ser Gly Gln Gly Met Phe Ala Gln Leu Val Ala Gln Asn Val Leu Leu
                165                 170                 175
```

-continued

Ile Asp Gly Pro Leu Ser Trp Tyr Ser Asp Pro Gly Leu Ala Gly Val
        180                 185                 190

Ser Leu Thr Gly Gly Leu Ser Tyr Lys Glu Asp Thr Lys Glu Leu Val
        195                 200                 205

Val Ala Lys Ala Gly Val Tyr Tyr Val Phe Gln Leu Glu Leu Arg
210                 215                 220

Arg Val Val Ala Gly Glu Gly Ser Gly Ser Val Ser Leu Ala Leu His
225                 230                 235                 240

Leu Gln Pro Leu Arg Ser Ala Ala Gly Ala Ala Leu Ala Leu Thr
                245                 250                 255

Val Asp Leu Pro Pro Ala Ser Ser Glu Ala Arg Asn Ser Ala Phe Gly
        260                 265                 270

Phe Gln Gly Arg Leu Leu His Leu Ser Ala Gly Gln Arg Leu Gly Val
        275                 280                 285

His Leu His Thr Glu Ala Arg Ala Arg His Ala Trp Gln Leu Thr Gln
        290                 295                 300

Gly Ala Thr Val Leu Gly Leu Phe Arg Val Gly Ser Gly Ser Gly Asn
305                 310                 315                 320

Gly Ser Gly Gln Gly Met Phe Ala Gln Leu Val Ala Gln Asn Val Leu
                325                 330                 335

Leu Ile Asp Gly Pro Leu Ser Trp Tyr Ser Asp Pro Gly Leu Ala Gly
                340                 345                 350

Val Ser Leu Thr Gly Gly Leu Ser Tyr Lys Glu Asp Thr Lys Glu Leu
                355                 360                 365

Val Val Ala Lys Ala Gly Val Tyr Tyr Val Phe Gln Leu Glu Leu
        370                 375                 380

Arg Arg Val Val Ala Gly Glu Gly Ser Gly Ser Val Ser Leu Ala Leu
385                 390                 395                 400

His Leu Gln Pro Leu Arg Ser Ala Ala Gly Ala Ala Leu Ala Leu
                405                 410                 415

Thr Val Asp Leu Pro Pro Ala Ser Ser Glu Ala Arg Asn Ser Ala Phe
                420                 425                 430

Gly Phe Gln Gly Arg Leu Leu His Leu Ser Ala Gly Gln Arg Leu Gly
        435                 440                 445

Val His Leu His Thr Glu Ala Arg Ala Arg His Ala Trp Gln Leu Thr
        450                 455                 460

Gln Gly Ala Thr Val Leu Gly Leu Phe Arg Val Gly Ser Ser Ser Ser
465                 470                 475                 480

Ser Ser Ser Ser Gly Ser Cys Asp Lys Thr His Thr Cys Pro Pro Cys
                485                 490                 495

Pro Ala Pro Glu Leu Leu Gly Gly Pro Ser Val Phe Leu Phe Pro Pro
                500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
        530                 535                 540

Tyr Val Asp Gly Val Glu Val His Asn Ala Lys Thr Lys Pro Arg Glu
545                 550                 555                 560

Glu Gln Tyr Ser Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
                580                 585                 590

```
Lys Ala Leu Pro Ala Pro Ile Glu Lys Thr Ile Ser Lys Ala Lys Gly
            595                 600                 605

Gln Pro Arg Glu Pro Gln Val Tyr Thr Leu Pro Ser Arg Glu Glu
610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
            645                 650                 655

Asn Tyr Lys Thr Thr Pro Pro Val Leu Asp Ser Asp Gly Ser Phe Phe
                660                 665                 670

Leu Tyr Ser Lys Leu Thr Val Asp Lys Ser Arg Trp Gln Gln Gly Asn
            675                 680                 685

Val Phe Ser Cys Ser Val Met His Glu Ala Leu His Asn His Tyr Thr
        690                 695                 700

Gln Lys Ser Leu Ser Leu Ser Pro Gly Lys
705                 710

<210> SEQ ID NO 35
<211> LENGTH: 711
<212> TYPE: PRT
<213> ORGANISM: Artificial Sequence
<220> FEATURE:
<223> OTHER INFORMATION: FAKE SEQ --> PLEASE REPLACE BY CORRECT SEQ

<400> SEQUENCE: 35

Gln Gly Met Phe Ala Gln Leu Val Ala Gln Asn Val Leu Leu Ile Asp
1               5                   10                  15

Gly Pro Leu Ser Trp Tyr Ser Asp Pro Gly Leu Ala Gly Val Ser Leu
            20                  25                  30

Thr Gly Gly Leu Ser Tyr Lys Glu Asp Thr Lys Glu Leu Val Val Ala
        35                  40                  45

Lys Ala Gly Val Tyr Tyr Val Phe Phe Gln Leu Glu Leu Arg Arg Val
    50                  55                  60

Val Ala Gly Glu Gly Ser Gly Ser Val Ser Leu Ala Leu His Leu Gln
65                  70                  75                  80

Pro Leu Arg Ser Ala Asn Gly Ser Ala Ala Leu Ala Leu Thr Val Asp
                85                  90                  95

Leu Pro Pro Ala Ser Ser Glu Ala Arg Asn Ser Ala Phe Gly Phe Gln
            100                 105                 110

Gly Arg Leu Leu His Leu Ser Ala Gly Gln Arg Leu Gly Val His Leu
        115                 120                 125

His Thr Glu Ala Arg Ala Arg His Ala Trp Gln Leu Thr Gln Gly Ala
    130                 135                 140

Thr Val Leu Gly Leu Phe Arg Val Gly Ser Gly Ser Gly Asn Gly Ser
145                 150                 155                 160

Gln Gly Met Phe Ala Gln Leu Val Ala Gln Asn Val Leu Leu Ile Asp
                165                 170                 175

Gly Pro Leu Ser Trp Tyr Ser Asp Pro Gly Leu Ala Gly Val Ser Leu
            180                 185                 190

Thr Gly Gly Leu Ser Tyr Lys Glu Asp Thr Lys Glu Leu Val Val Ala
        195                 200                 205

Lys Ala Gly Val Tyr Tyr Val Phe Phe Gln Leu Glu Leu Arg Arg Val
    210                 215                 220

Val Ala Gly Glu Gly Ser Gly Ser Val Ser Leu Ala Leu His Leu Gln
225                 230                 235                 240
```

```
Pro Leu Arg Ser Ala Asn Gly Ser Ala Ala Leu Ala Leu Thr Val Asp
                245                 250                 255

Leu Pro Pro Ala Ser Ser Glu Ala Arg Asn Ser Ala Phe Gly Phe Gln
            260                 265                 270

Gly Arg Leu Leu His Leu Ser Ala Gly Gln Arg Leu Gly Val His Leu
        275                 280                 285

His Thr Glu Ala Arg Ala Arg His Ala Trp Gln Leu Thr Gln Gly Ala
    290                 295                 300

Thr Val Leu Gly Leu Phe Arg Val Gly Ser Ser Gly Asn Gly Ser
305                 310                 315                 320

Gln Gly Met Phe Ala Gln Leu Val Ala Gln Asn Val Leu Leu Ile Asp
                325                 330                 335

Gly Pro Leu Ser Trp Tyr Ser Asp Pro Gly Leu Ala Gly Val Ser Leu
            340                 345                 350

Thr Gly Gly Leu Ser Tyr Lys Glu Asp Thr Lys Glu Leu Val Val Ala
        355                 360                 365

Lys Ala Gly Val Tyr Tyr Val Phe Phe Gln Leu Glu Leu Arg Arg Val
    370                 375                 380

Val Ala Gly Glu Gly Ser Gly Ser Val Ser Leu Ala Leu His Leu Gln
385                 390                 395                 400

Pro Leu Arg Ser Ala Asn Gly Ser Ala Ala Leu Ala Leu Thr Val Asp
                405                 410                 415

Leu Pro Pro Ala Ser Ser Glu Ala Arg Asn Ser Ala Phe Gly Phe Gln
            420                 425                 430

Gly Arg Leu Leu His Leu Ser Ala Gly Gln Arg Leu Gly Val His Leu
        435                 440                 445

His Thr Glu Ala Arg Ala Arg His Ala Trp Gln Leu Thr Gln Gly Ala
    450                 455                 460

Thr Val Leu Gly Leu Phe Arg Val Gly Ser Ser Ser Ser Ser Ser Ser
465                 470                 475                 480

Ser Gly Ser Cys Asp Lys Thr His Thr Cys Pro Pro Cys Pro Ala Pro
                485                 490                 495

Glu Leu Leu Gly Gly Pro Ser Val Phe Leu Phe Pro Pro Lys Pro Lys
            500                 505                 510

Asp Thr Leu Met Ile Ser Arg Thr Pro Glu Val Thr Cys Val Val Val
        515                 520                 525

Asp Val Ser His Glu Asp Pro Glu Val Lys Phe Asn Trp Tyr Val Asp
    530                 535                 540

Gly Val Glu Val His Asn Ala Lys Thr Lys Pro Arg Glu Glu Gln Tyr
545                 550                 555                 560

Ser Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
            580                 585                 590

Pro Ala Pro Ile Glu Lys Thr Ile Ser Lys Ala Lys Gly Gln Pro Arg
        595                 600                 605

Glu Pro Gln Val Tyr Thr Leu Pro Pro Ser Arg Glu Glu Met Thr Lys
    610                 615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
```

```
                660                665                670
Lys Leu Thr Val Asp Lys Ser Arg Trp Gln Gln Gly Asn Val Phe Ser
                    675                680                685

Cys Ser Val Met His Glu Ala Leu His Asn His Tyr Thr Gln Lys Ser
                690                695                700

Leu Ser Leu Ser Pro Gly Lys
705                710

<210> SEQ ID NO 36
<211> LENGTH: 472
<212> TYPE: PRT
<213> ORGANISM: Artificial Sequence
<220> FEATURE:
<223> OTHER INFORMATION: example of scCD137L-RBD module

<400> SEQUENCE: 36

Gln Gly Met Phe Ala Gln Leu Val Ala Gln Asn Val Leu Leu Ile Asp
1               5                   10                  15

Gly Pro Leu Ser Trp Tyr Ser Asp Pro Gly Leu Ala Gly Val Ser Leu
                20                  25                  30

Thr Gly Gly Leu Ser Tyr Lys Glu Asp Thr Lys Glu Leu Val Val Ala
            35                  40                  45

Lys Ala Gly Val Tyr Tyr Val Phe Phe Gln Leu Glu Leu Arg Arg Val
    50                  55                  60

Val Ala Gly Glu Gly Ser Gly Ser Val Ser Leu Ala Leu His Leu Gln
65                  70                  75                  80

Pro Leu Arg Ser Ala Ala Gly Ala Ala Ala Leu Ala Leu Thr Val Asp
                85                  90                  95

Leu Pro Pro Ala Ser Ser Glu Ala Arg Asn Ser Ala Phe Gly Phe Gln
                100                 105                 110

Gly Arg Leu Leu His Leu Ser Ala Gly Gln Arg Leu Gly Val His Leu
            115                 120                 125

His Thr Glu Ala Arg Ala Arg His Ala Trp Gln Leu Thr Gln Gly Ala
    130                 135                 140

Thr Val Leu Gly Leu Phe Arg Val Gly Ser Gly Ser Gly Asn Gly Ser
145                 150                 155                 160

Gln Gly Met Phe Ala Gln Leu Val Ala Gln Asn Val Leu Leu Ile Asp
                165                 170                 175

Gly Pro Leu Ser Trp Tyr Ser Asp Pro Gly Leu Ala Gly Val Ser Leu
                180                 185                 190

Thr Gly Gly Leu Ser Tyr Lys Glu Asp Thr Lys Glu Leu Val Val Ala
            195                 200                 205

Lys Ala Gly Val Tyr Tyr Val Phe Phe Gln Leu Glu Leu Arg Arg Val
    210                 215                 220

Val Ala Gly Glu Gly Ser Gly Ser Val Ser Leu Ala Leu His Leu Gln
225                 230                 235                 240

Pro Leu Arg Ser Ala Ala Gly Ala Ala Ala Leu Ala Leu Thr Val Asp
                245                 250                 255

Leu Pro Pro Ala Ser Ser Glu Ala Arg Asn Ser Ala Phe Gly Phe Gln
                260                 265                 270

Gly Arg Leu Leu His Leu Ser Ala Gly Gln Arg Leu Gly Val His Leu
            275                 280                 285

His Thr Glu Ala Arg Ala Arg His Ala Trp Gln Leu Thr Gln Gly Ala
    290                 295                 300

Thr Val Leu Gly Leu Phe Arg Val Gly Ser Gly Ser Gly Asn Gly Ser
```

```
                305                 310                 315                 320
            Gln Gly Met Phe Ala Gln Leu Val Ala Gln Asn Val Leu Leu Ile Asp
                            325                 330                 335
            Gly Pro Leu Ser Trp Tyr Ser Asp Pro Gly Leu Ala Gly Val Ser Leu
                        340                 345                 350
            Thr Gly Leu Ser Tyr Lys Glu Asp Thr Lys Glu Leu Val Val Ala
                    355                 360                 365
            Lys Ala Gly Val Tyr Tyr Val Phe Phe Gln Leu Glu Leu Arg Arg Val
                370                 375                 380
            Val Ala Gly Glu Gly Ser Gly Val Ser Leu Ala Leu His Leu Gln
            385                 390                 395                 400
            Pro Leu Arg Ser Ala Ala Gly Ala Ala Ala Leu Ala Leu Thr Val Asp
                            405                 410                 415
            Leu Pro Pro Ala Ser Ser Glu Ala Arg Asn Ser Ala Phe Gly Phe Gln
                        420                 425                 430
            Gly Arg Leu Leu His Leu Ser Ala Gly Gln Arg Leu Gly Val His Leu
                    435                 440                 445
            His Thr Glu Ala Arg Ala Arg His Ala Trp Gln Leu Thr Gln Gly Ala
                450                 455                 460
            Thr Val Leu Gly Leu Phe Arg Val
            465                 470

<210> SEQ ID NO 37
<211> LENGTH: 2240
<212> TYPE: DNA
<213> ORGANISM: Artificial Sequence
<220> FEATURE:
<223> OTHER INFORMATION: DNA sequence encoding SEQ ID NO:25

<400> SEQUENCE: 37
aagctttagg gataacaggg taatagccgc caccatggag actgacaccc tgctggtgtt        60
cgtgctgctg gtctgggtgc ctgcaggaaa tggacagggc atgttcgctc aactggtcgc       120
acagaacgtg ctgctcattg acggtcccct gtcttggtac tccgatccag ggttggcagg       180
agtgtccttg acaggagggc tgtcctataa ggaggatacc aaagagctgg tggtagcaaa       240
ggctggtgtg tattacgtgt tctttcagct ggagctgcgc agagtcgtcg caggcgaagg       300
atctggtagt gtgtcactgg cactgcactt gcagcccctt cggtccgctg ccggggcagc       360
agcactggcc ctgaccgtcg atctgccacc cgcttctagc gaggcacgaa actcagcctt       420
tgggtttcag ggtcgcctgc tgcacctgag cgccggacag aggctgggcg ttcatctgca       480
caccgaggcc agagccagac acgcttggca gttgactcag ggagctacgg tcctcggtct       540
gtttcgagta ggcagcggaa gcggcaatgg ctctcagggc atgtttgctc agctggtagc       600
ccagaacgta ctcctgatcg atggccctct ttcatggtac tcagaccccg gactggccgg       660
agttagcctt acaggtgggc ttagttataa ggaggacaca aaggaattgg ttgtggccaa       720
agctggcgtg tactatgtgt tcttccagct tgagctccgc agagtcgtgg ctggggaggg       780
ctctggcagt gtgagccttg cccttcatct gcaaccttg cggagcgcag ccggcgctgc       840
tgcactggcc cttacagtgg atttgccacc cgcaagtagt gaagctcgca attccgcatt       900
cggtttccag ggccgtctgc tccatctttc tgccggtcaa cgtctgggag ttcacctcca       960
cactgaggct agggccaggc atgcttggca gctgactcaa ggagccactg tcttgggact      1020 cttccggta ggctccgggt ctggcaacgg ctcccagggg atgtttgccc aactggtcgc      1080
ccagaatgtc ctgctcatcg atggtcctct gagctggtat tccgaccctg gactggctgg      1140
```

```
tgtgagcctg actggcggac tctcctacaa agaggacacc aaggaactgg tggtggccaa    1200
agccggggtg tactacgtgt tcttccagtt ggaactgcgg cgggttgtgg ctggcgaggg    1260
atcaggttcc gttagtctgg ccctgcacct ccagcctctg aggtctgctg ctggtgccgc    1320
cgctctggcc ttgaccgtcg acctcccacc cgcatcttcc gaagcccgaa attcagcctt    1380
cgggttccag ggcagactgc tgcatctgag tgctggacag cgccttgggg ttcatctcca    1440
caccgaagcc agggcccgac atgcctggca gctcacacaa ggcgcaaccg ttttggggct    1500
ctttcgtgtg ggatcctcga gttcatcgtc ctcatccggc tcatgtgata agacccacac    1560
ctgcccctcc tgtcctgccc ctgagctgct gggcggacct tctgtgttcc tgttcccccc    1620
caagcctaag gacaccctga tgatctccag gacccctgag gtgacctgtg tggtggtgga    1680
cgtgtctcac gaagatcccg aggtgaagtt caactggtac gtggacggcg tggaggtcca    1740
caacgccaag accaagccta gggaggagca gtacagctcc acctaccggg tggtgtctgt    1800
gctgaccgtg ctgcaccagg attggctgaa cggaaaggag tataagtgta aggtctccaa    1860
caaggccctg cctgccccca tcgagaaaac catctccaag gccaagggcc agcctcggga    1920
gcctcaggtg tacaccctgc ctcctagcag ggaggagatg accaagaacc aggtgtccct    1980
gacctgtctg gtgaagggct cctacccttc cgatatcgcc gtggagtggg agtctaatgg    2040
ccagcccgag aacaactaca agaccacccc tcctgtgctg gactctgacg gctccttctt    2100
cctgtactcc aagctgaccg tggacaagtc cagatggcag cagggcaacg tgttctcctg    2160
ctccgtgatg cacgaggccc tgcacaatca ctacacccag aagtccctgt ctctgagtcc    2220
gggcaagtaa taggcgcgcc                                                 2240
```

<210> SEQ ID NO 38
<211> LENGTH: 229
<212> TYPE: PRT
<213> ORGANISM: Artificial Sequence
<220> FEATURE:
<223> OTHER INFORMATION: homotrimeric CD137L fused to RB69 FOLDON

<400> SEQUENCE: 38

```
Met Glu Thr Asp Thr Leu Leu Val Phe Val Leu Leu Val Trp Val Pro
1               5                   10                  15

Ala Gly Asn Gly Gln Gly Met Phe Ala Gln Leu Val Ala Gln Asn Val
            20                  25                  30

Leu Leu Ile Asp Gly Pro Leu Ser Trp Tyr Ser Asp Pro Gly Leu Ala
        35                  40                  45

Gly Val Ser Leu Thr Gly Gly Leu Ser Tyr Lys Glu Asp Thr Lys Glu
    50                  55                  60

Leu Val Val Ala Lys Ala Gly Val Tyr Tyr Val Phe Phe Gln Leu Glu
65                  70                  75                  80

Leu Arg Arg Val Val Ala Gly Glu Gly Ser Gly Ser Val Ser Leu Ala
                85                  90                  95

Leu His Leu Gln Pro Leu Arg Ser Ala Ala Gly Ala Ala Ala Leu Ala
            100                 105                 110

Leu Thr Val Asp Leu Pro Pro Ala Ser Ser Glu Ala Arg Asn Ser Ala
        115                 120                 125

Phe Gly Phe Gln Gly Arg Leu Leu His Leu Ser Ala Gly Gln Arg Leu
    130                 135                 140

Gly Val His Leu His Thr Glu Ala Arg Ala Arg His Ala Trp Gln Leu
145                 150                 155                 160
```

Thr Gln Gly Ala Thr Val Leu Gly Leu Phe Arg Val Gly Ser Gly Ser
                    165                 170                 175

Ser Gly Ser Ser Gly Ser Ser Gly Tyr Ile Glu Asp Ala Pro
            180                 185                 190

Ser Asp Gly Lys Phe Tyr Val Arg Lys Asp Gly Ala Trp Val Glu Leu
            195                 200                 205

Pro Thr Ala Ser Gly Pro Ser Ser Ser Ser Ser Ala Trp Ser His
    210                 215                 220

Pro Gln Phe Glu Lys
225

<210> SEQ ID NO 39
<211> LENGTH: 481
<212> TYPE: PRT
<213> ORGANISM: Artificial Sequence
<220> FEATURE:
<223> OTHER INFORMATION: single chain CD137 lignad RBD (example)

<400> SEQUENCE: 39

Gln Leu Arg Gln Gly Met Phe Ala Gln Leu Val Ala Gln Asn Val Leu
1               5                   10                  15

Leu Ile Asp Gly Pro Leu Ser Trp Tyr Ser Asp Pro Gly Leu Ala Gly
            20                  25                  30

Val Ser Leu Thr Gly Gly Leu Ser Tyr Lys Glu Asp Thr Lys Glu Leu
            35                  40                  45

Val Val Ala Lys Ala Gly Val Tyr Tyr Val Phe Phe Gln Leu Glu Leu
        50                  55                  60

Arg Arg Val Val Ala Gly Glu Gly Ser Gly Ser Val Ser Leu Ala Leu
65                  70                  75                  80

His Leu Gln Pro Leu Arg Ser Ala Ala Gly Ala Ala Ala Leu Ala Leu
                85                  90                  95

Thr Val Asp Leu Pro Pro Ala Ser Ser Glu Ala Arg Asn Ser Ala Phe
            100                 105                 110

Gly Phe Gln Gly Arg Leu Leu His Leu Ser Ala Gly Gln Arg Leu Gly
            115                 120                 125

Val His Leu His Thr Glu Ala Arg Ala Arg His Ala Trp Gln Leu Thr
        130                 135                 140

Gln Gly Ala Thr Val Leu Gly Leu Phe Arg Val Gly Ser Gly Ser Gly
145                 150                 155                 160

Asn Gly Ser Asp Leu Arg Gln Gly Met Phe Ala Gln Leu Val Ala Gln
                165                 170                 175

Asn Val Leu Leu Ile Asp Gly Pro Leu Ser Trp Tyr Ser Asp Pro Gly
            180                 185                 190

Leu Ala Gly Val Ser Leu Thr Gly Gly Leu Ser Tyr Lys Glu Asp Thr
            195                 200                 205

Lys Glu Leu Val Val Ala Lys Ala Gly Val Tyr Tyr Val Phe Phe Gln
        210                 215                 220

Leu Glu Leu Arg Arg Val Val Ala Gly Glu Gly Ser Gly Ser Val Ser
225                 230                 235                 240

Leu Ala Leu His Leu Gln Pro Leu Arg Ser Ala Ala Gly Ala Ala Ala
                245                 250                 255

Leu Ala Leu Thr Val Asp Leu Pro Pro Ala Ser Ser Glu Ala Arg Asn
            260                 265                 270

Ser Ala Phe Gly Phe Gln Gly Arg Leu Leu His Leu Ser Ala Gly Gln
            275                 280                 285

Arg Leu Gly Val His Leu His Thr Glu Ala Arg Ala Arg His Ala Trp
    290                 295                 300
Gln Leu Thr Gln Gly Ala Thr Val Leu Gly Leu Phe Arg Val Gly Ser
305                 310                 315                 320
Gly Ser Gly Asn Gly Ser Asp Leu Arg Gln Gly Met Phe Ala Gln Leu
                325                 330                 335
Val Ala Gln Asn Val Leu Leu Ile Asp Gly Pro Leu Ser Trp Tyr Ser
            340                 345                 350
Asp Pro Gly Leu Ala Gly Val Ser Leu Thr Gly Gly Leu Ser Tyr Lys
        355                 360                 365
Glu Asp Thr Lys Glu Leu Val Val Ala Lys Ala Gly Val Tyr Tyr Val
    370                 375                 380
Phe Phe Gln Leu Glu Leu Arg Arg Val Val Ala Gly Glu Gly Ser Gly
385                 390                 395                 400
Ser Val Ser Leu Ala Leu His Leu Gln Pro Leu Arg Ser Ala Ala Gly
                405                 410                 415
Ala Ala Ala Leu Ala Leu Thr Val Asp Leu Pro Pro Ala Ser Ser Glu
            420                 425                 430
Ala Arg Asn Ser Ala Phe Gly Phe Gln Gly Arg Leu Leu His Leu Ser
        435                 440                 445
Ala Gly Gln Arg Leu Gly Val His Leu His Thr Glu Ala Arg Ala Arg
    450                 455                 460
His Ala Trp Gln Leu Thr Gln Gly Ala Thr Val Leu Gly Leu Phe Arg
465                 470                 475                 480
Val

<210> SEQ ID NO 40
<211> LENGTH: 475
<212> TYPE: PRT
<213> ORGANISM: Artificial Sequence
<220> FEATURE:
<223> OTHER INFORMATION: single chain CD137 lignad RBD (example)

<400> SEQUENCE: 40

Arg Gln Gly Met Phe Ala Gln Leu Val Ala Gln Asn Val Leu Leu Ile
1               5                   10                  15
Asp Gly Pro Leu Ser Trp Tyr Ser Asp Pro Gly Leu Ala Gly Val Ser
            20                  25                  30
Leu Thr Gly Gly Leu Ser Tyr Lys Glu Asp Thr Lys Glu Leu Val Val
        35                  40                  45
Ala Lys Ala Gly Val Tyr Tyr Val Phe Phe Gln Leu Glu Leu Arg Arg
    50                  55                  60
Val Val Ala Gly Glu Gly Ser Gly Ser Val Ser Leu Ala Leu His Leu
65                  70                  75                  80
Gln Pro Leu Arg Ser Ala Ala Gly Ala Ala Ala Leu Ala Leu Thr Val
                85                  90                  95
Asp Leu Pro Pro Ala Ser Ser Glu Ala Arg Asn Ser Ala Phe Gly Phe
            100                 105                 110
Gln Gly Arg Leu Leu His Leu Ser Ala Gly Gln Arg Leu Gly Val His
        115                 120                 125
Leu His Thr Glu Ala Arg Ala Arg His Ala Trp Gln Leu Thr Gln Gly
    130                 135                 140
Ala Thr Val Leu Gly Leu Phe Arg Val Gly Ser Gly Ser Gly Asn Gly
145                 150                 155                 160

Ser Arg Gln Gly Met Phe Ala Gln Leu Val Ala Gln Asn Val Leu Leu

```
                165                 170                 175
Ile Asp Gly Pro Leu Ser Trp Tyr Ser Asp Pro Gly Leu Ala Gly Val
            180                 185                 190
Ser Leu Thr Gly Gly Leu Ser Tyr Lys Glu Asp Thr Lys Glu Leu Val
            195                 200                 205
Val Ala Lys Ala Gly Val Tyr Tyr Val Phe Phe Gln Leu Glu Leu Arg
            210                 215                 220
Arg Val Ala Gly Glu Gly Ser Gly Ser Val Ser Leu Ala Leu His
225                 230                 235                 240
Leu Gln Pro Leu Arg Ser Ala Ala Gly Ala Ala Leu Ala Leu Thr
                245                 250                 255
Val Asp Leu Pro Pro Ala Ser Ser Glu Ala Arg Asn Ser Ala Phe Gly
            260                 265                 270
Phe Gln Gly Arg Leu Leu His Leu Ser Ala Gly Gln Arg Leu Gly Val
            275                 280                 285
His Leu His Thr Glu Ala Arg Ala Arg His Ala Trp Gln Leu Thr Gln
            290                 295                 300
Gly Ala Thr Val Leu Gly Leu Phe Arg Val Gly Ser Gly Ser Gly Asn
305                 310                 315                 320
Gly Ser Arg Gln Gly Met Phe Ala Gln Leu Val Ala Gln Asn Val Leu
                325                 330                 335
Leu Ile Asp Gly Pro Leu Ser Trp Tyr Ser Asp Pro Gly Leu Ala Gly
            340                 345                 350
Val Ser Leu Thr Gly Gly Leu Ser Tyr Lys Glu Asp Thr Lys Glu Leu
            355                 360                 365
Val Val Ala Lys Ala Gly Val Tyr Tyr Val Phe Phe Gln Leu Glu Leu
            370                 375                 380
Arg Arg Val Val Ala Gly Glu Gly Ser Gly Ser Val Ser Leu Ala Leu
385                 390                 395                 400
His Leu Gln Pro Leu Arg Ser Ala Ala Gly Ala Ala Leu Ala Leu
                405                 410                 415
Thr Val Asp Leu Pro Pro Ala Ser Ser Glu Ala Arg Asn Ser Ala Phe
            420                 425                 430
Gly Phe Gln Gly Arg Leu Leu His Leu Ser Ala Gly Gln Arg Leu Gly
            435                 440                 445
Val His Leu His Thr Glu Ala Arg Ala Arg His Ala Trp Gln Leu Thr
            450                 455                 460
Gln Gly Ala Thr Val Leu Gly Leu Phe Arg Val
465                 470                 475

<210> SEQ ID NO 41
<211> LENGTH: 475
<212> TYPE: PRT
<213> ORGANISM: Artificial Sequence
<220> FEATURE:
<223> OTHER INFORMATION: single chain CD137 lignad RBD (example)

<400> SEQUENCE: 41

Gln Gln Gly Met Phe Ala Gln Leu Val Ala Gln Asn Val Leu Leu Ile
1               5                   10                  15
Asp Gly Pro Leu Ser Trp Tyr Ser Asp Pro Gly Leu Ala Gly Val Ser
            20                  25                  30
Leu Thr Gly Gly Leu Ser Tyr Lys Glu Asp Thr Lys Glu Leu Val Val
            35                  40                  45
Ala Lys Ala Gly Val Tyr Tyr Val Phe Phe Gln Leu Glu Leu Arg Arg
```

-continued

```
                  50                  55                  60
        Val Val Ala Gly Glu Gly Ser Gly Ser Val Ser Leu Ala Leu His Leu
        65                  70                  75                  80

Gln Pro Leu Arg Ser Ala Ala Gly Ala Ala Ala Leu Ala Leu Thr Val
                            85                  90                  95

Asp Leu Pro Pro Ala Ser Ser Glu Ala Arg Asn Ser Ala Phe Gly Phe
                        100                 105                 110

Gln Gly Arg Leu Leu His Leu Ser Ala Gly Gln Arg Leu Gly Val His
                        115                 120                 125

Leu His Thr Glu Ala Arg Ala Arg His Ala Trp Gln Leu Thr Gln Gly
                    130                 135                 140

Ala Thr Val Leu Gly Leu Phe Arg Val Gly Ser Gly Ser Gly Asn Gly
        145                 150                 155                 160

Ser Gly Gln Gly Met Phe Ala Gln Leu Val Ala Gln Asn Val Leu Leu
                        165                 170                 175

Ile Asp Gly Pro Leu Ser Trp Tyr Ser Asp Pro Gly Leu Ala Gly Val
                        180                 185                 190

Ser Leu Thr Gly Gly Leu Ser Tyr Lys Glu Asp Thr Lys Glu Leu Val
                    195                 200                 205

Val Ala Lys Ala Gly Val Tyr Tyr Val Phe Phe Gln Leu Glu Leu Arg
                    210                 215                 220

Arg Val Ala Gly Glu Gly Ser Gly Ser Val Ser Leu Ala Leu His
        225                 230                 235                 240

Leu Gln Pro Leu Arg Ser Ala Ala Gly Ala Ala Ala Leu Ala Leu Thr
                        245                 250                 255

Val Asp Leu Pro Pro Ala Ser Ser Glu Ala Arg Asn Ser Ala Phe Gly
                        260                 265                 270

Phe Gln Gly Arg Leu Leu His Leu Ser Ala Gly Gln Arg Leu Gly Val
                        275                 280                 285

His Leu His Thr Glu Ala Arg Ala Arg His Ala Trp Gln Leu Thr Gln
                    290                 295                 300

Gly Ala Thr Val Leu Gly Leu Phe Arg Val Gly Ser Gly Ser Gly Asn
        305                 310                 315                 320

Gly Ser Gly Gln Gly Met Phe Ala Gln Leu Val Ala Gln Asn Val Leu
                        325                 330                 335

Leu Ile Asp Gly Pro Leu Ser Trp Tyr Ser Asp Pro Gly Leu Ala Gly
                        340                 345                 350

Val Ser Leu Thr Gly Gly Leu Ser Tyr Lys Glu Asp Thr Lys Glu Leu
                        355                 360                 365

Val Val Ala Lys Ala Gly Val Tyr Tyr Val Phe Phe Gln Leu Glu Leu
                        370                 375                 380

Arg Arg Val Val Ala Gly Glu Gly Ser Gly Ser Val Ser Leu Ala Leu
        385                 390                 395                 400

His Leu Gln Pro Leu Arg Ser Ala Ala Gly Ala Ala Ala Leu Ala Leu
                        405                 410                 415

Thr Val Asp Leu Pro Pro Ala Ser Ser Glu Ala Arg Asn Ser Ala Phe
                        420                 425                 430

Gly Phe Gln Gly Arg Leu Leu His Leu Ser Ala Gly Gln Arg Leu Gly
                        435                 440                 445

Val His Leu His Thr Glu Ala Arg Ala Arg His Ala Trp Gln Leu Thr
                        450                 455                 460

Gln Gly Ala Thr Val Leu Gly Leu Phe Arg Val
        465                 470                 475
```

<210> SEQ ID NO 42
<211> LENGTH: 475
<212> TYPE: PRT
<213> ORGANISM: Artificial Sequence
<220> FEATURE:
<223> OTHER INFORMATION: single chain CD137 lignad RBD (example)

<400> SEQUENCE: 42

```
Ser Gln Gly Met Phe Ala Gln Leu Val Ala Gln Asn Val Leu Leu Ile
1               5                   10                  15

Asp Gly Pro Leu Ser Trp Tyr Ser Asp Pro Gly Leu Ala Gly Val Ser
            20                  25                  30

Leu Thr Gly Gly Leu Ser Tyr Lys Glu Asp Thr Lys Glu Leu Val Val
        35                  40                  45

Ala Lys Ala Gly Val Tyr Tyr Val Phe Phe Gln Leu Glu Leu Arg Arg
    50                  55                  60

Val Val Ala Gly Glu Gly Ser Gly Ser Val Ser Leu Ala Leu His Leu
65                  70                  75                  80

Gln Pro Leu Arg Ser Ala Ala Gly Ala Ala Ala Leu Ala Leu Thr Val
                85                  90                  95

Asp Leu Pro Pro Ala Ser Ser Glu Ala Arg Asn Ser Ala Phe Gly Phe
            100                 105                 110

Gln Gly Arg Leu Leu His Leu Ser Ala Gly Gln Arg Leu Gly Val His
        115                 120                 125

Leu His Thr Glu Ala Arg Ala Arg His Ala Trp Gln Leu Thr Gln Gly
    130                 135                 140

Ala Thr Val Leu Gly Leu Phe Arg Val Gly Ser Gly Ser Gly Asn Gly
145                 150                 155                 160

Ser Gly Gln Gly Met Phe Ala Gln Leu Val Ala Gln Asn Val Leu Leu
                165                 170                 175

Ile Asp Gly Pro Leu Ser Trp Tyr Ser Asp Pro Gly Leu Ala Gly Val
            180                 185                 190

Ser Leu Thr Gly Gly Leu Ser Tyr Lys Glu Asp Thr Lys Glu Leu Val
        195                 200                 205

Val Ala Lys Ala Gly Val Tyr Tyr Val Phe Phe Gln Leu Glu Leu Arg
    210                 215                 220

Arg Val Val Ala Gly Glu Gly Ser Gly Ser Val Ser Leu Ala Leu His
225                 230                 235                 240

Leu Gln Pro Leu Arg Ser Ala Ala Gly Ala Ala Ala Leu Ala Leu Thr
                245                 250                 255

Val Asp Leu Pro Pro Ala Ser Ser Glu Ala Arg Asn Ser Ala Phe Gly
            260                 265                 270

Phe Gln Gly Arg Leu Leu His Leu Ser Ala Gly Gln Arg Leu Gly Val
        275                 280                 285

His Leu His Thr Glu Ala Arg Ala Arg His Ala Trp Gln Leu Thr Gln
    290                 295                 300

Gly Ala Thr Val Leu Gly Leu Phe Arg Val Gly Ser Gly Ser Gly Asn
305                 310                 315                 320

Gly Ser Gly Gln Gly Met Phe Ala Gln Leu Val Ala Gln Asn Val Leu
                325                 330                 335

Leu Ile Asp Gly Pro Leu Ser Trp Tyr Ser Asp Pro Gly Leu Ala Gly
            340                 345                 350

Val Ser Leu Thr Gly Gly Leu Ser Tyr Lys Glu Asp Thr Lys Glu Leu
        355                 360                 365
```

```
Val Val Ala Lys Ala Gly Val Tyr Tyr Val Phe Phe Gln Leu Glu Leu
    370                 375                 380

Arg Arg Val Val Ala Gly Glu Gly Ser Gly Ser Val Ser Leu Ala Leu
385                 390                 395                 400

His Leu Gln Pro Leu Arg Ser Ala Ala Gly Ala Ala Leu Ala Leu
                405                 410                 415

Thr Val Asp Leu Pro Pro Ala Ser Ser Glu Ala Arg Asn Ser Ala Phe
                420                 425                 430

Gly Phe Gln Gly Arg Leu Leu His Leu Ser Ala Gly Gln Arg Leu Gly
                435                 440                 445

Val His Leu His Thr Glu Ala Arg Ala Arg His Ala Trp Gln Leu Thr
                450                 455                 460

Gln Gly Ala Thr Val Leu Gly Leu Phe Arg Val
465                 470                 475

<210> SEQ ID NO 43
<211> LENGTH: 472
<212> TYPE: PRT
<213> ORGANISM: Artificial Sequence
<220> FEATURE:
<223> OTHER INFORMATION: single chain CD137 lignad RBD (example)

<400> SEQUENCE: 43

Gln Gly Met Phe Ala Gln Leu Val Ala Gln Asn Val Leu Leu Ile Asp
1               5                   10                  15

Gly Pro Leu Ser Trp Tyr Ser Asp Pro Gly Leu Ala Gly Val Ser Leu
                20                  25                  30

Thr Gly Gly Leu Ser Tyr Lys Glu Asp Thr Lys Glu Leu Val Val Ala
            35                  40                  45

Lys Ala Gly Val Tyr Tyr Val Phe Phe Gln Leu Glu Leu Arg Arg Val
50                  55                  60

Val Ala Gly Glu Gly Ser Gly Ser Val Ser Leu Ala Leu His Leu Gln
65                  70                  75                  80

Pro Leu Arg Ser Ala Asn Gly Ser Ala Ala Leu Ala Leu Thr Val Asp
                85                  90                  95

Leu Pro Pro Ala Ser Ser Glu Ala Arg Asn Ser Ala Phe Gly Phe Gln
                100                 105                 110

Gly Arg Leu Leu His Leu Ser Ala Gly Gln Arg Leu Gly Val His Leu
            115                 120                 125

His Thr Glu Ala Arg Ala Arg His Ala Trp Gln Leu Thr Gln Gly Ala
130                 135                 140

Thr Val Leu Gly Leu Phe Arg Val Gly Ser Gly Ser Gly Asn Gly Ser
145                 150                 155                 160

Gln Gly Met Phe Ala Gln Leu Val Ala Gln Asn Val Leu Leu Ile Asp
                165                 170                 175

Gly Pro Leu Ser Trp Tyr Ser Asp Pro Gly Leu Ala Gly Val Ser Leu
                180                 185                 190

Thr Gly Gly Leu Ser Tyr Lys Glu Asp Thr Lys Glu Leu Val Val Ala
            195                 200                 205

Lys Ala Gly Val Tyr Tyr Val Phe Phe Gln Leu Glu Leu Arg Arg Val
        210                 215                 220

Val Ala Gly Glu Gly Ser Gly Ser Val Ser Leu Ala Leu His Leu Gln
225                 230                 235                 240

Pro Leu Arg Ser Ala Asn Gly Ser Ala Ala Leu Ala Leu Thr Val Asp
                245                 250                 255
```

```
Leu Pro Pro Ala Ser Ser Glu Ala Arg Asn Ser Ala Phe Gly Phe Gln
            260             265             270

Gly Arg Leu Leu His Leu Ser Ala Gly Gln Arg Leu Gly Val His Leu
        275             280             285

His Thr Glu Ala Arg Ala Arg His Ala Trp Gln Leu Thr Gln Gly Ala
        290             295             300

Thr Val Leu Gly Leu Phe Arg Val Gly Ser Gly Ser Gly Asn Gly Ser
305             310             315             320

Gln Gly Met Phe Ala Gln Leu Val Ala Gln Asn Val Leu Leu Ile Asp
            325             330             335

Gly Pro Leu Ser Trp Tyr Ser Asp Pro Gly Leu Ala Gly Val Ser Leu
            340             345             350

Thr Gly Gly Leu Ser Tyr Lys Glu Asp Thr Lys Glu Leu Val Val Ala
            355             360             365

Lys Ala Gly Val Tyr Tyr Val Phe Phe Gln Leu Glu Leu Arg Arg Val
    370             375             380

Val Ala Gly Glu Gly Ser Gly Ser Val Ser Leu Ala Leu His Leu Gln
385             390             395             400

Pro Leu Arg Ser Ala Asn Gly Ser Ala Ala Leu Ala Leu Thr Val Asp
            405             410             415

Leu Pro Pro Ala Ser Ser Glu Ala Arg Asn Ser Ala Phe Gly Phe Gln
            420             425             430

Gly Arg Leu Leu His Leu Ser Ala Gly Gln Arg Leu Gly Val His Leu
        435             440             445

His Thr Glu Ala Arg Ala Arg His Ala Trp Gln Leu Thr Gln Gly Ala
        450             455             460

Thr Val Leu Gly Leu Phe Arg Val
465             470
```